(12) United States Patent
Murakami et al.

(10) Patent No.: US 11,008,387 B2
(45) Date of Patent: May 18, 2021

(54) ANTIBODY INHIBITING BINDING OF VEGF TO NRP1

(71) Applicants: ORDER-MADE MEDICAL RESEARCH INC., Kashiwa (JP); SANTEN PHARMACEUTICAL CO., LTD., Osaka (JP)

(72) Inventors: Yasufumi Murakami, Chiba (JP); Hiroyuki Satofuka, Chiba (JP); Shigeki Mukoubata, Chiba (JP); Hirotada Akiyama, Chiba (JP); Tatsuji Kurose, Nara (JP); Sae Akao, Nara (JP)

(73) Assignees: ORDER-MADE MEDICAL RESEARCH INC., Kashiwa (JP); SANTEN PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/067,958

(22) PCT Filed: Jan. 5, 2017

(86) PCT No.: PCT/JP2017/000100
§ 371 (c)(1),
(2) Date: Jul. 3, 2018

(87) PCT Pub. No.: WO2017/119434
PCT Pub. Date: Jul. 13, 2017

(65) Prior Publication Data
US 2019/0322732 A1   Oct. 24, 2019

(30) Foreign Application Priority Data

Jan. 6, 2016  (JP) .............................. JP2016-001275

(51) Int. Cl.
| | |
|---|---|
| *A61K 39/395* | (2006.01) |
| *C07K 16/22* | (2006.01) |
| *A61P 27/02* | (2006.01) |
| *A61P 35/00* | (2006.01) |
| *C12N 5/12* | (2006.01) |
| *C12N 15/02* | (2006.01) |

(52) U.S. Cl.
CPC .............. *C07K 16/22* (2013.01); *A61P 27/02* (2018.01); *A61P 35/00* (2018.01); *C12N 5/12* (2013.01); *C12N 15/02* (2013.01)

(58) Field of Classification Search
None
See application file for complete search history.

(56) References Cited

U.S. PATENT DOCUMENTS

| | | | |
|---|---|---|---|
| 2002/0119153 A1 | 8/2002 | Thorpe et al. | |
| 2005/0106667 A1 | 5/2005 | Fellouse et al. | |
| 2008/0213268 A1 | 9/2008 | Watts et al. | |
| 2010/0061988 A1 | 3/2010 | Hansen | |
| 2010/0111967 A1 | 5/2010 | Baehner et al. | |
| 2010/0150919 A1 | 6/2010 | Appleton et al. | |
| 2011/0097340 A1 | 4/2011 | Ramachandra et al. | |
| 2012/0014958 A1 | 1/2012 | Borras et al. | |
| 2012/0231011 A1 | 9/2012 | Li et al. | |
| 2014/0170137 A1 | 6/2014 | Gearing | |
| 2015/0315270 A1 | 11/2015 | Baldi et al. | |
| 2016/0122426 A1 | 5/2016 | Doh et al. | |
| 2017/0015742 A1 | 1/2017 | Gu et al. | |

FOREIGN PATENT DOCUMENTS

| | | |
|---|---|---|
| EP | 0419858 A1 | 4/1991 |
| EP | 3006465 A1 | 4/2016 |
| JP | 2002-543093 A | 12/2002 |
| JP | 2007-526756 A | 9/2007 |
| JP | 2010-530359 A | 9/2010 |
| JP | 2011-500086 A | 1/2011 |
| JP | 2011-525359 A | 9/2011 |
| JP | 2011-256183 A | 12/2011 |
| JP | 2012-504943 A | 3/2012 |
| JP | 2013-502445 A | 1/2013 |
| JP | 2014-516026 A | 7/2014 |
| WO | WO 2007/047626 A1 | 4/2007 |
| WO | WO 2014/193191 A1 | 12/2014 |
| WO | WO 2015/166112 A1 | 11/2015 |
| WO | WO 2016/205427 A2 | 12/2016 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Rudikoff et al. (1982). PNAS. 79:1979-1983.*
Arber et al. (2016). Blood 127:2391-2405.*
Swerdlow et al. (2016). Blood 127:2375-2390.*
Beck et al., "A Vascular niche and a VEGF-Nrp1 loop regulate the initiation and stemness of skin tumours", Nature, vol. 478, Oct. 20, 2011, pp. 399-403 (7 pages).
Carmeliet et al., "Common Mechanisms of nerve and blood vessel wiring," Nature, vol. 436, No. 14, Jul. 2005, pp. 193-200 (8 pages).
Doi et al., "S7-5 Clinical Applications of Molecular Target Inhibitors Through VEGF/VEGFR ( Focusing on Antibody Medicine", The 45th Congress of Japan Society for Cancer Therapy, vol. 42, No. 2, Sep. 20, 2007, pp. 249 with abstract.

(Continued)

*Primary Examiner* — Christine J Saoud
*Assistant Examiner* — Jon M Lockard
(74) *Attorney, Agent, or Firm* — Birch, Stewart, Kolasch & Birch, LLP

(57) ABSTRACT

An object of the present invention is to provide an antibody against VEGF that inhibits binding of a vascular endothelial growth factor (VEGF) to neuropilin-1 (NRP1). The present invention provides an antibody against VEGF that inhibits binding of VEGF to NRP1.

20 Claims, 14 Drawing Sheets

Specification includes a Sequence Listing.

(56) References Cited

OTHER PUBLICATIONS

Extended European Search Report, dated Aug. 13, 2019, for European Application No. 17735972.6.
Extended European Search Report, dated Aug. 19, 2019, for European Application No. 17735971.8.
Ferrara et al., "The Biology of Vascular Endothelial Growth Factor," Endocrine Reviews, vol. 18, No. 1, Feb. 1997, pp. 4-25 (22 pages).
Graziani et al, "Neuropilin-1 as therapeutic target for malignant melanoma", Frontiers in Oncology, vol. 5, Article 125, Jun. 2015, pp. 1-9 (9 pages).
Harper et al., "VEGF-A Splicing: the key to anti-angiogenic therapeutics", Nat Rev Cancer. Author Manuscript, vol. 8, No. 11, Nov. 2008, pp. 880-887 (17 pages).
Heskamp et al., "Bevacizumab reduces tumor targeting of antiepidermal growth factor and anti-insulin growth factor 1 receptor antibodies", Int. J. Cancer, vol. 133, 2013, pp. 307-314 (8 pages).
International Search Report, dated Apr. 11, 2017, for International Application No. PCT/JP2017/000101, with an English translation.
Jones et al., "Separating genetic and hemodynamic defects in neuropilin 1 knockout embryos", Development, vol. 135, 2008, pp. 2479-2488 (10 pages).
Keyt et al., "Identification of Vascular Endothelial Growth Factor Determinants for Binding KDR and FLT-1 Receptors", The Journal of Biological Chemistry, vol. 271, No. 10, 1996, pp. 5638-5646 (10 pages).
Khadidja-Tehami et al., "Production of polyclonal anti VEGF antibodies and establishment of sELISA system for detection of serum VEGF level in tumor patients", Journal of Chemical and Pharmaceutical Research, vol. 7, No. 6, 2015, pp. 672-679 (8 pages).
Marti et al., "Angioenesis in Ischemic Disease" Thromb Haemost, vol. 82, 1999, pp. 44-52 (9 pages).
Matsumoto et al., "VEGF Receptor Signal Transduction", Science's stke, URL: www.stke.org/cgi/content/full/OC_sigtrans;2001/112/re21, 2011, pp. 1-17 (17 pages).
Pan et al., "Blocking Neuropilin-1 Funtion Has an Additve Effect with Anti-VEGF to Inhibit Tumor Growth" Cancer Cell, vol. 11, Jan. 2007, pp. 53-67 (15 pages).
Parker et al., "Structural Basis for Selective Vascular Endothelial Growth Factor-A (VEGF-A) Binding to Neuropilin-1", The Journal of Biological Chemistry, vol. 287, No. 14, Mar. 30, 2012, pp. 11082-11089 (8 pages).
Schi Afppi et al, "Characterization of a new potent, in vivo neutralizing monoclonal antibody to human vascular endothelial growth factor", J. Cancer Res Clin Oncol, vol. 125, 1999, pp. 336-342 (7 pages).
Soker et al., "Neuropilin-1 Is Expressed by Endothelial and Tumor Cells as an Isoform-Specifc Receptor and Vascular Endothelial Growth Factor", Cell, vol. 92, Mar. 20, 1998, pp. 735-745 (11 pages).
Stewart, "Aflibercept as a Treatment for Age-Related Macular Degeneration", US Opthalimic Rev. vol. 6, 2013, pp. 58-63 (6 pages).
Sullivan et al, "r84, a Novel Therapeutic Antibody against Mouse and Human VEGF with Potent Anti-Tumor Activity and Limited Toxicity Induction" Plos One, vol. 5, Issue 8, Aug. 2010, pp. 1-13 (13 pages).
Tugues et al, "Vascular endothelial growth factors and receptors: Anti-angiogenic therapy in the treatment of cancer", Molecular Aspects of Medicine, vol. 32, 2011, pp. 88-111 (24 pages).
Yu et al, "A Humanized Anti-VEGF Rabbit Monoclonal Antibody Inhibits Angiogenesis and Blocks Tumor Growth in Xenograft Models", PloS ONE, vol. 5, Issue 2, Feb. 2010, pp. 1-12 (12 pages).
Geretti et al., "A mutated soluble neuropilin-2 B domain antagonizes VEGF bioactivity and inhibits tumor progression", Mol Cancer Res., vol. 8, No. 8, 2010, pp. 1-22.
Grünewald et al., "Structure-function analysis of VEGF receptor activation and the role of coreceptors in angiogenic signaling", Biochimica et Biophysica Acta, vol. 1804, 2010,(Available online Sep. 15, 2009), pp. 567-580.
Lal Goel et al., "VEGF targets the tumour cell", Nat Rev Cancer., vol. 13, No. 12, Dec. 2013, pp. 1-30.
MacDonald et al, "Aflibercept exhibits VEGF binding stoichiometry distinct from bevacizumab and does not support formation of immune-like complexes", Angiogenesis, vol. 19, 2016, (Published online: May 27, 2016), pp. 389-406.
Muller et al., "VEGF and the Fab fragment of a humanized neutralizing antibody: crystal structure of the complex at 2.4 A resolution and mutational analysis of the interface", Structure, vol. 6, No. 9, Sep. 15, 1998, pp. 1153-1167.
Tischer et al., "The Human Gene for Vascular Endothelial Growth Factor", The Journal of Biological Chemistry, vol. 266, No. 18, Issue of Jun. 25, 1991, pp. 11947-11954.
Wentink et al., "Targeted vaccination against the bevacizumab binding site on VEGF using 3D-Structured peptides elicits efficient antitumor actiivity", PNAS, vol. 113, No. 44, Nov. 1, 2016, pp. 12532-12537.

* cited by examiner

[Figure 1]
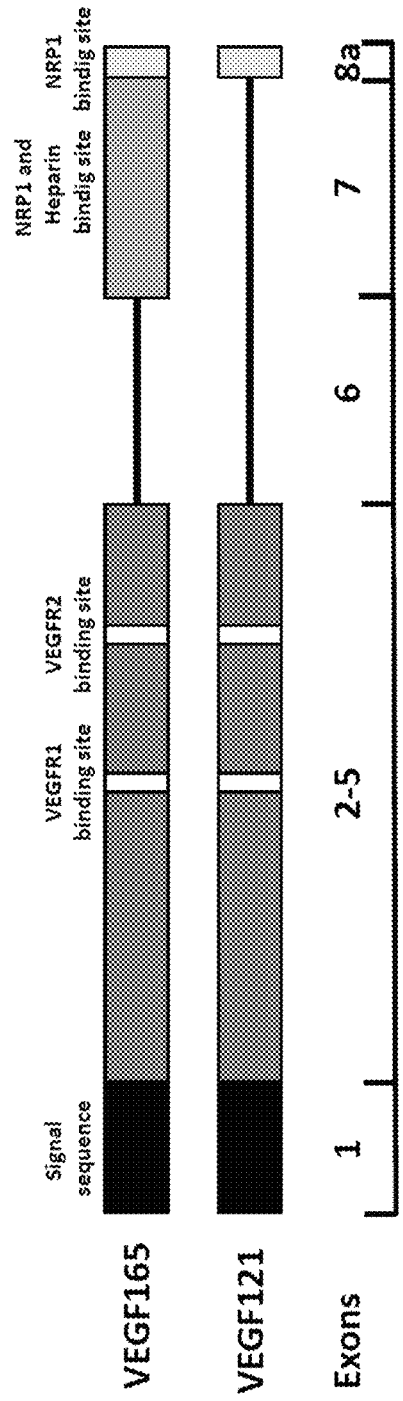

[Figure 2]
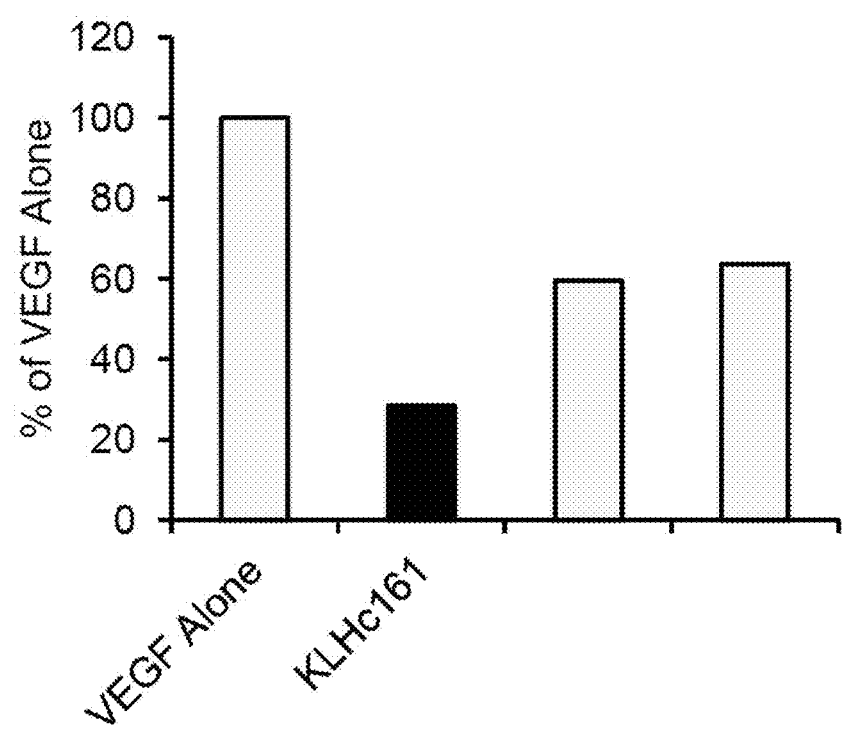

[Figure 3]
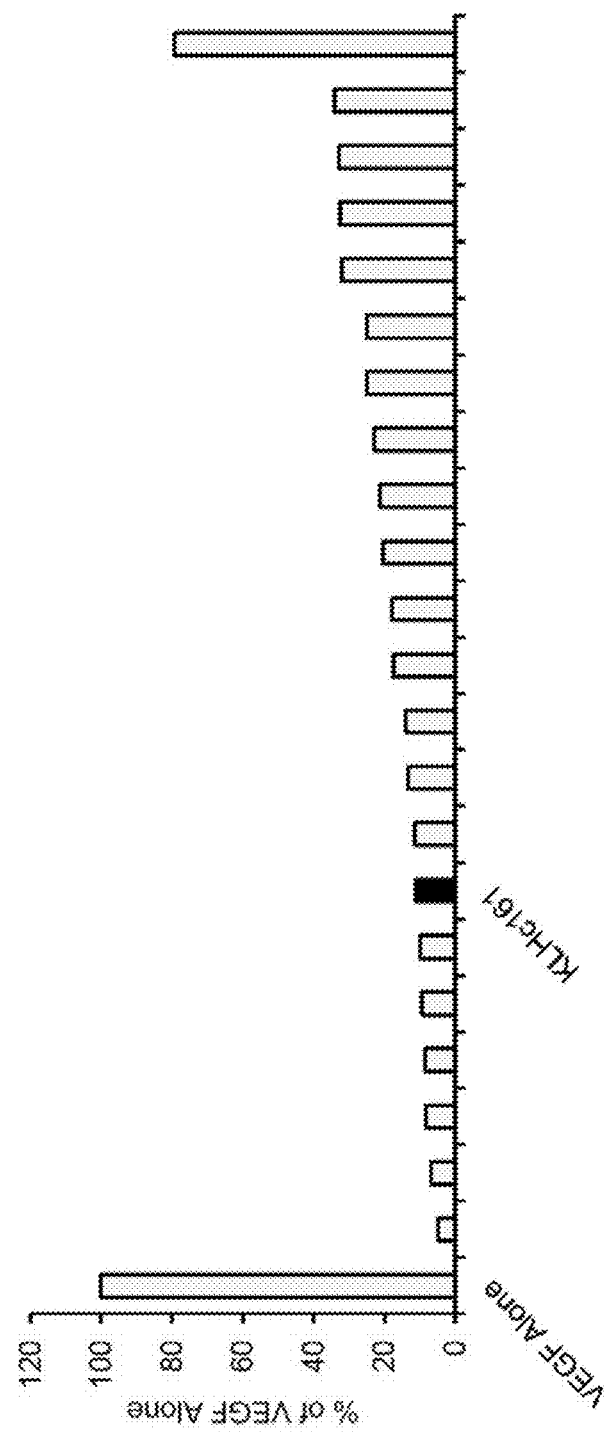

[Figure 4]
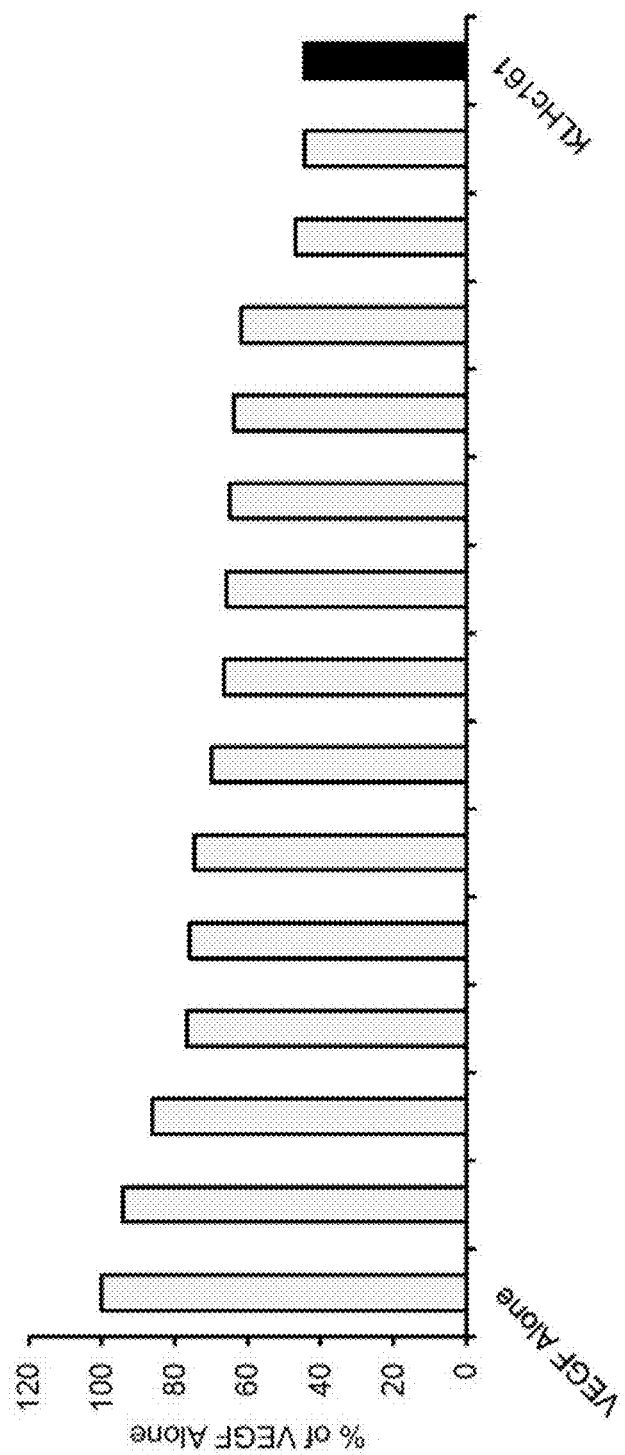

[Figure 5]
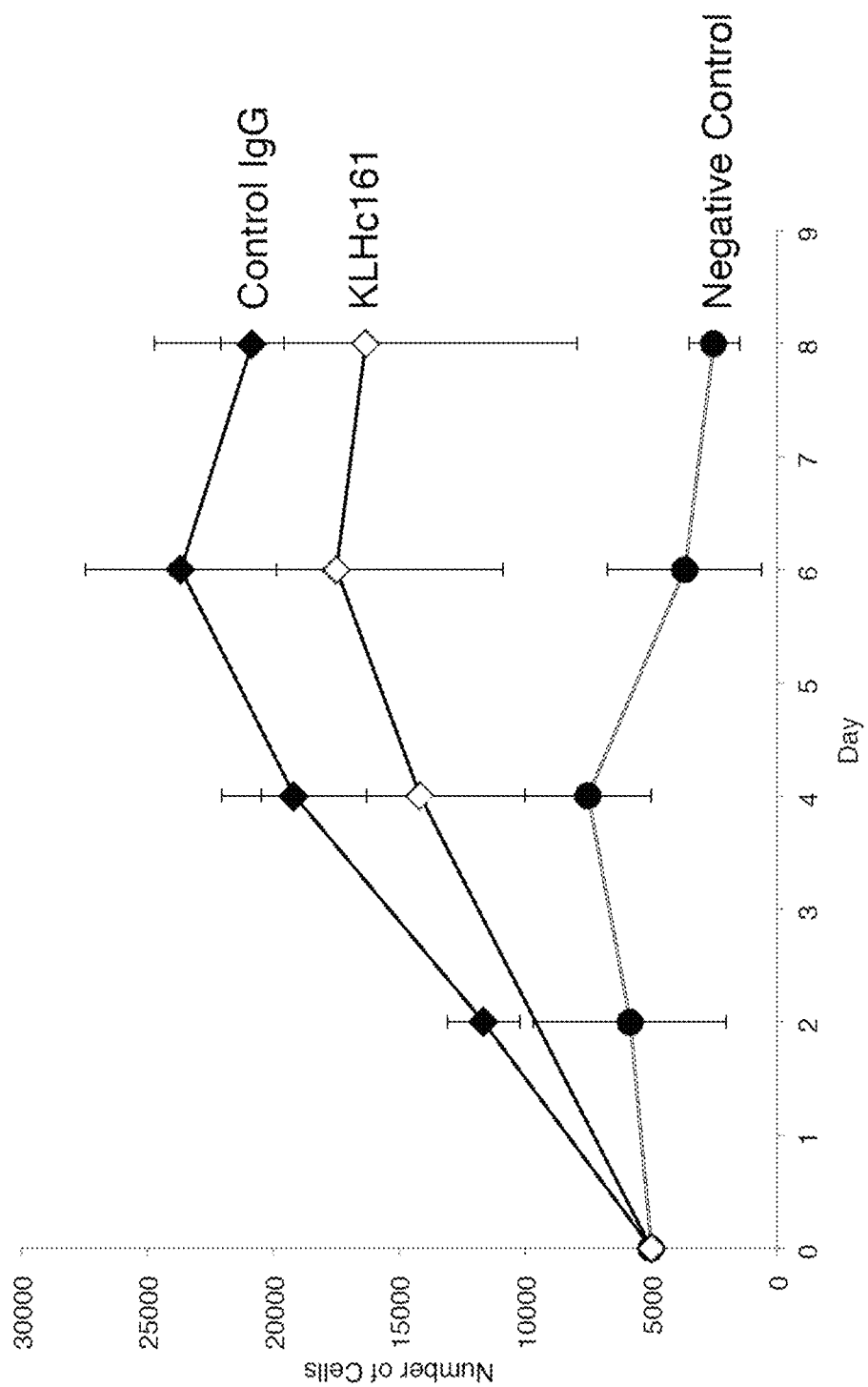

[Figure 6]
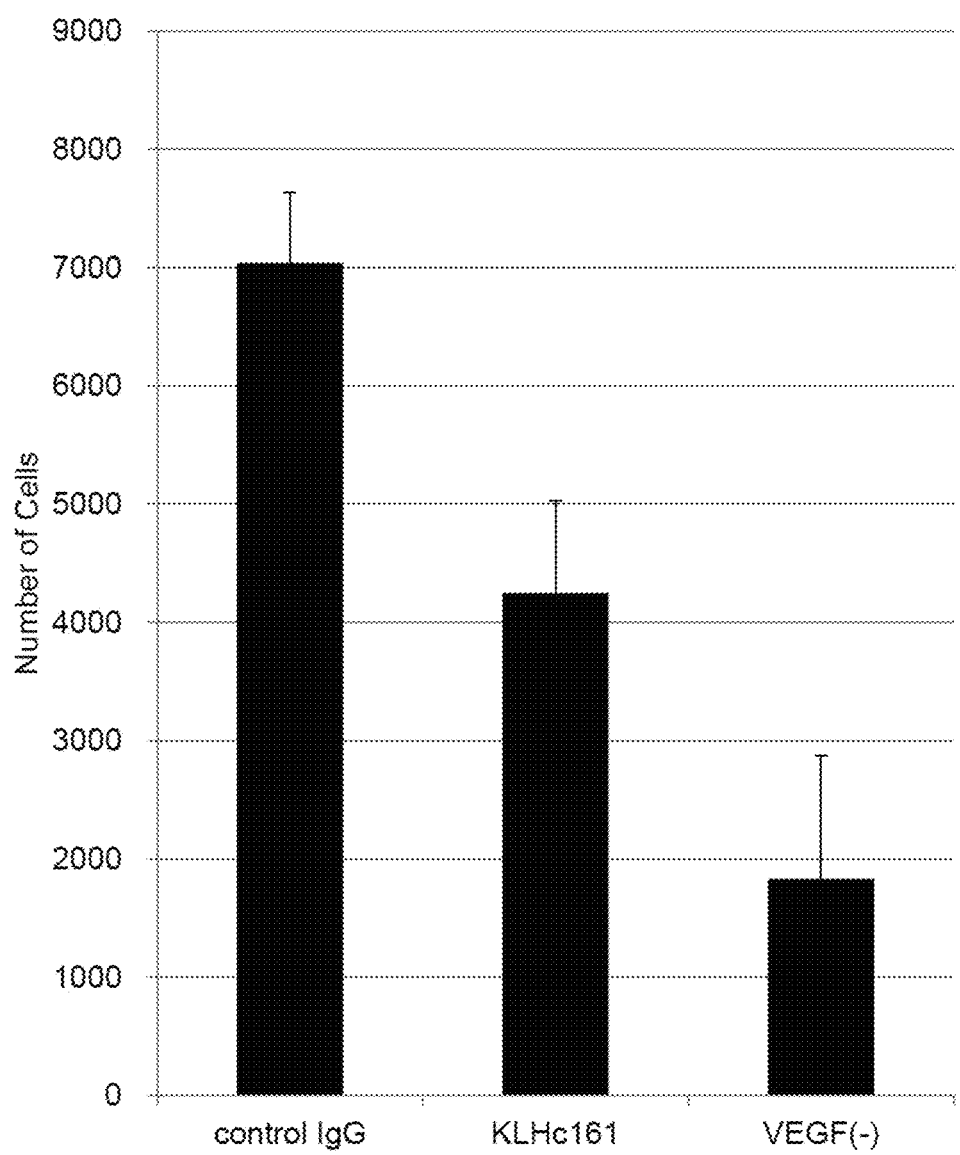

[Figure 7]
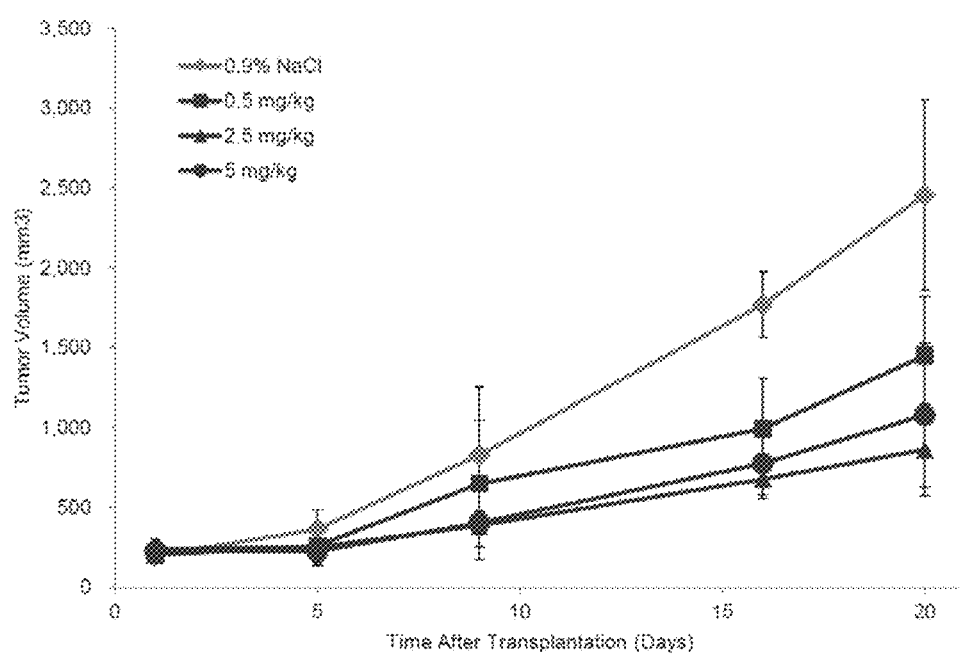

[Figure 8]
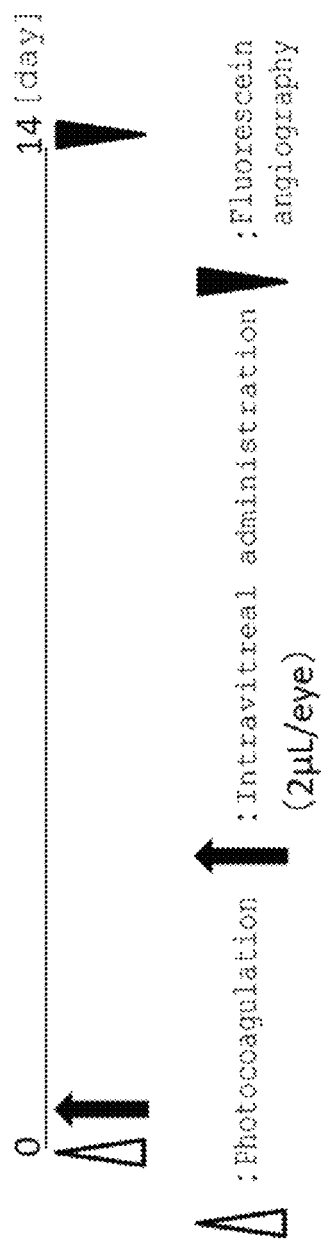

[Figure 9]
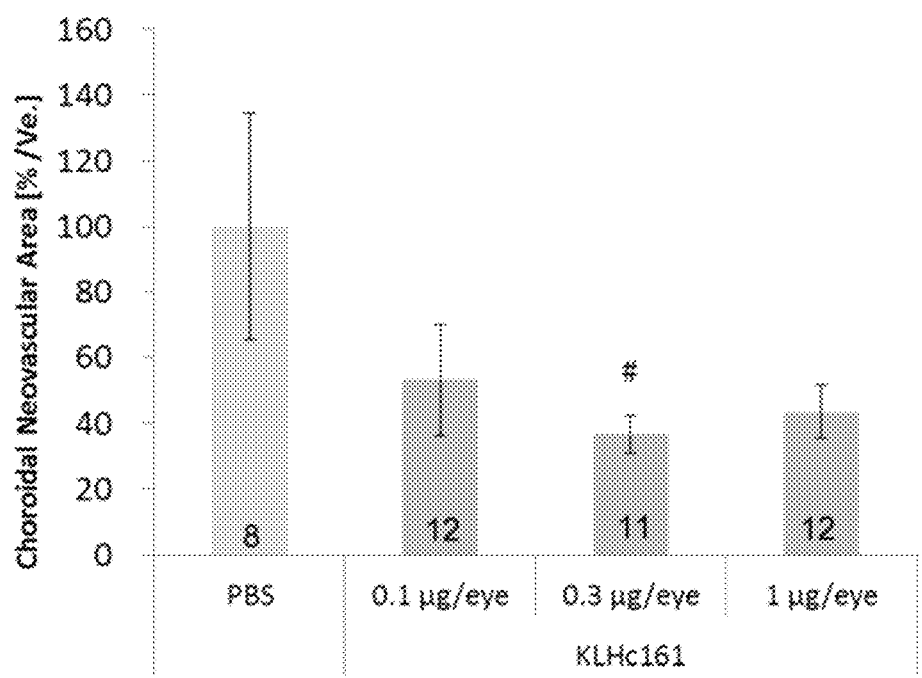

[Figure 10]
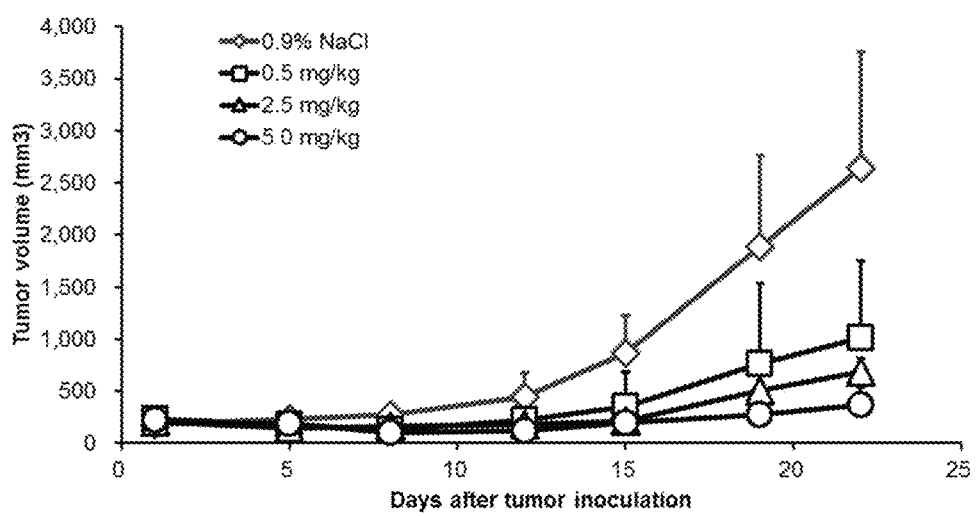

[Figure 11]
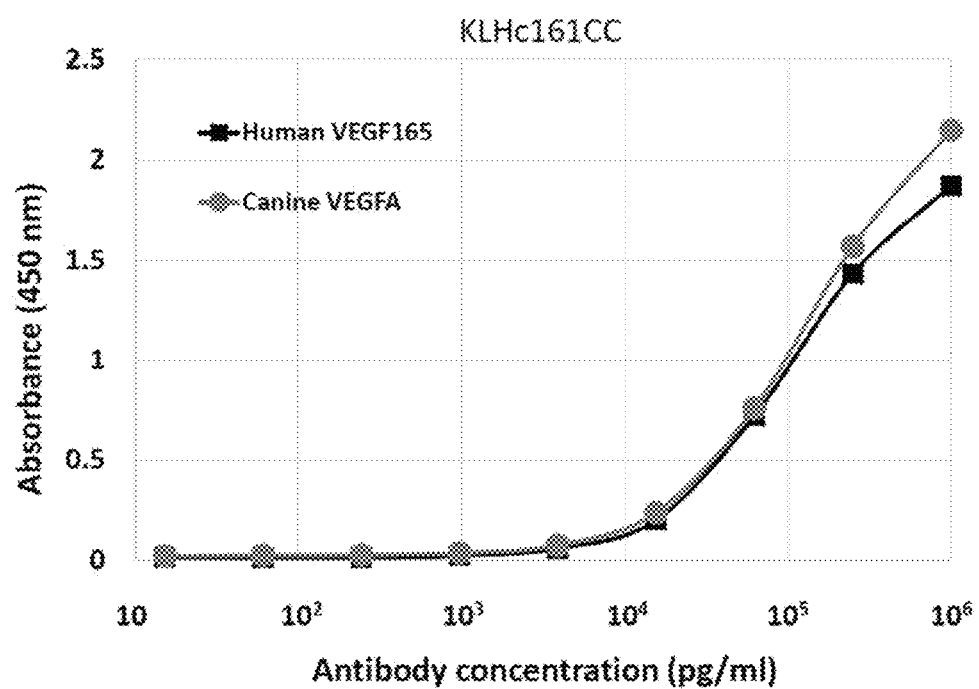

[Figure 12]
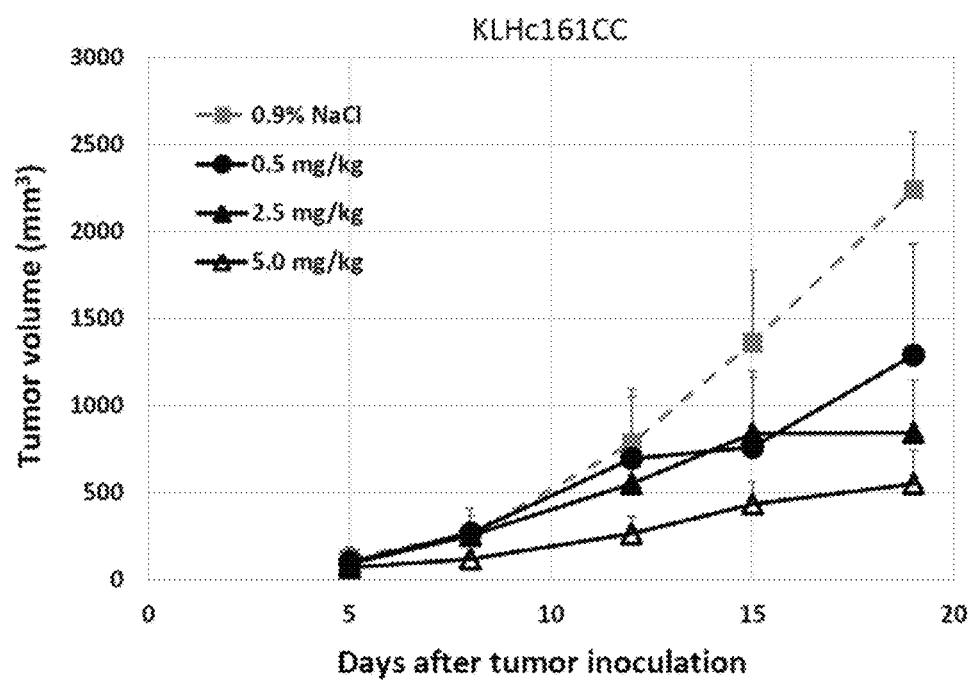

[Figure 13]
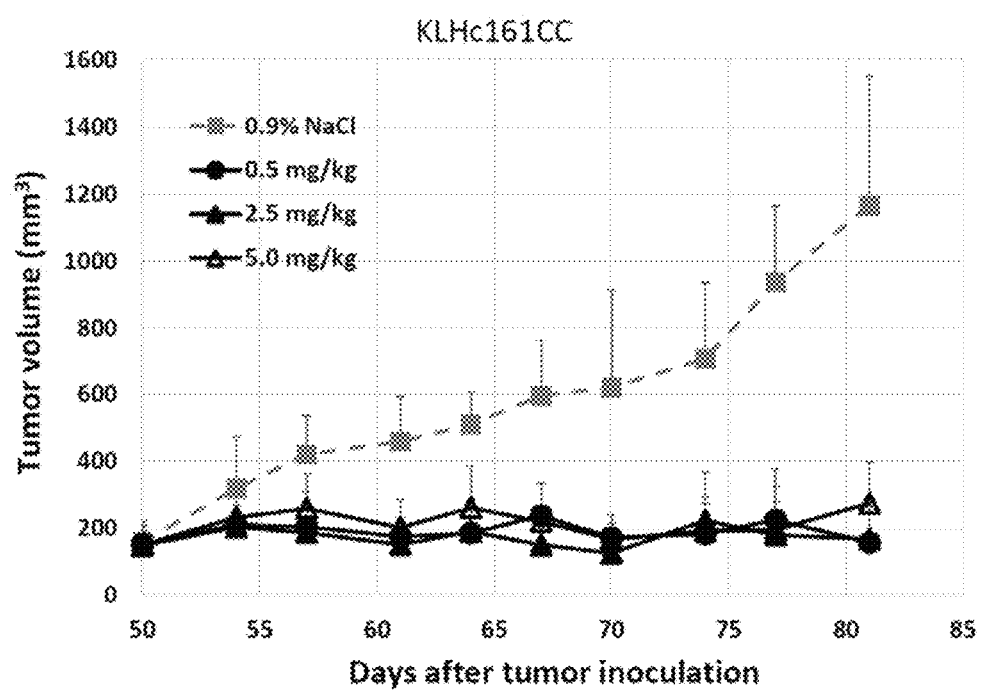

[Figure 14]
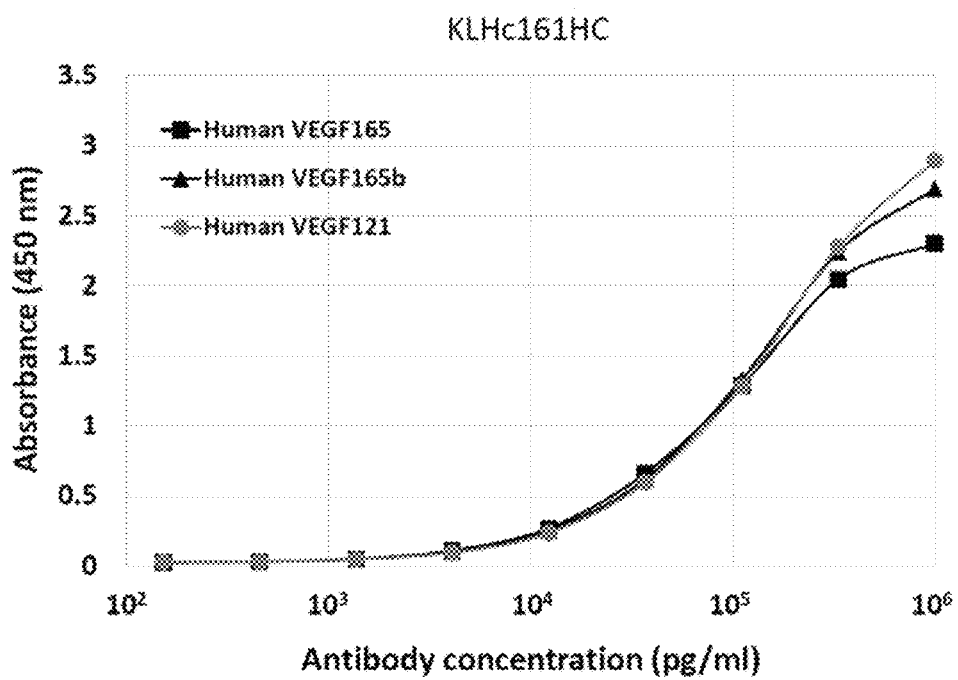

ANTIBODY INHIBITING BINDING OF VEGF TO NRP1

TECHNICAL FIELD

The present invention relates to an antibody that inhibits binding of a vascular endothelial growth factor (VEGF) to neuropilin-1 (NRP1), and a pharmaceutical composition comprising the antibody.

BACKGROUND ART

Formation of new blood vessels (angiogenesis) is an essential process for maintaining life. On the other hand, pathological angiogenesis is known to be associated with many diseases.

As factors involved in angiogenesis, vascular endothelial growth factors (VEGF) are known (Non Patent Literature 1: Ferrara N, et al, Endocr Rev., 1997, 18 (1): 4-25). VEGFs are known to involve cell division and migration, induction of differentiation, vascular hyperpermeability, activation of monocytes and macrophages, and the like through binding to their receptors to cause intracellular signal transduction.

As VEGF receptors, 3 types of VEGF receptors including vascular endothelial growth factor receptor-1 (VEGFR1 (another name: Flt-1)), vascular endothelial growth factor receptor-2 (VEGFR2 (another name: KDR)), and neuropilin-1 (NRP1) have been reported.

NRP1 is a type I transmembrane glycoprotein of about 130 kDa, has been initially reported as an axon-guidance mediator, and also has been reported to play an important role in vasculogenesis (Non Patent Literature 2: Nature, 436: 193-200, 2005). Moreover, studies using knockout mice have reported that the loss of NRP1 functions results in defective blood vessel remodeling and branching (Non Patent Literature 3: Development, 135, 2479-88, 2008). Furthermore, it has been reported that in epithelial cells, NRP1 has a function to enhance signals generated by binding of VEGF to VEGFR2 to accelerate cell migration and vasculogenesis (Non Patent Literature 4: Cell, 92, 735-745, 1998).

VEGFs form a VEGF family consisting of VEGF-A, VEGF-B, VEGF-C, VEGF-D, VEGF-E, PIGF-1, and PIGF-2. Human VEGF-A is known to have subtypes such as $VEGF_{121}$, $VEGF_{145}$, $VEGF_{165}$, $VEGF_{183}$, $VEGF_{189}$, and $VEGF_{206}$, and $VEGF_{165}$ is the most prevalent. Moreover, $VEGF_{165}$ is known to bind to all of VEGFR1, VEGFR2 and NRP1.

In the meantime, as a subtype of $VEGF_{165}$, $VEGF_{165b}$ having 6 residues on the C-terminus of $VEGF_{165}$ translated not from exon 8a, but from exon 8b has been reported. Unlike $VEGF_{165}$, $VEGF_{165b}$ has been reported to have functions opposite to those of VEGFs, such as a function of suppressing angiogenesis and a function of suppressing the growth of kidney cancer. It is considered that $VEGF_{165b}$ does not form a conformation for binding to NRP1 because $VEGF_{165b}$ has serine (Ser) substituted from the $160^{th}$ cysteine (Cys) in $VEGF_{165}$, and thus no angiogenesis takes place (Non Patent Literature 5: Nature Reviews Cancer, 8, 880-887, 2008).

Furthermore, VEGF is known to induce not only normal angiogenesis, but also pathological angiogenesis and vascular hyperpermeability. As diseases associated with pathological angiogenesis, malignant transformation of tumors, tumor metastasis, wet-type age-related macular degeneration and the like are known. As diseases associated with abnormal vascular hyperpermeability, retinal vein occlusion, diabetic macular edema, and the like are known. Antibodies neutralizing VEGF activity are used for treatment of these diseases.

Anti-VEGF neutralizing antibodies suppress the growth of various human tumor cell lines in nude mice, and inhibit intraocular neovasculogenesis in an ischemic retinal disorder model (Patent Literature 1: JP Laid-Open Publication No. 2011-525359, Patent Literature 2: JP Laid-Open Publication No. 2007-526756). As an anti-VEGF antibody, bevacizumab (bevacizumab, Avastin®) is known, and the use of the same in combination with a chemotherapy regimen for treating metastatic colorectal cancer (CRC) and non-small-cell lung cancer (NSCLC) has been approved by FDA.

Moreover, as a Fab (antigen-binding fragment) antibody of bevacizumab, Ranibizumab (Ranibizumab Lucentis®) has been developed. Ranibizumab was approved by FDA in 2006 as an age-related macular degeneration therapeutic drug.

Bevacizumab and its Fab antibody are considered to exert its efficacy with a mechanism by which the binding thereof to VEGF inhibits binding of VEGF to VEGFR1 and of VEGF to VEGFR2, thereby inhibiting angiogenesis and lowering the supply of nutrients to rapidly growing cancer cells. However, it is known that bevacizumab does not inhibit binding of VEGF to NRP1.

In the meantime, among antibodies against NRP1, monoclonal antibodies that inhibit binding of VEGF to NRP1 have been reported (Patent Literature 3: JP Laid-Open Publication No. 2010-530359). These antibodies bind to NRP1 to inhibit binding of VEGF to NRP1, and thus to suppress VEGF functions.

It has been reported that VEGF has effects involving angiogenesis and vascular permeability, while affecting cancer stem cells. It has been reported that in skin squamous cell carcinoma, VEGF involves the regulation of the sternness of cancer stem cells through its binding to NRP1 (Non Patent Literature 5: Nature, 478, 399-403, 2011).

As described above, bevacizumab is an antibody that inhibits binding of VEGF to VEGFR1 and of VEGF to VEGFR2, and is unable to inhibit binding of VEGF to NRP1. Also, no antibody among antibodies against VEGF has been reported to inhibit binding of VEGF to NRP1.

CITATION LIST

Patent Literature

Patent Literature 1: JP Laid-Open Publication No. 2011-525359
Patent Literature 2: JP Laid-Open Publication No. 2007-526756
Patent Literature 3: JP Laid-Open Publication No. 2010-530359

Non Patent Literature

Non Patent Literature 1: Endocrine Reviews, 18, 4-25, 1997
Non Patent Literature 2: Nature, 436: 193-200, 2005
Non Patent Literature 3: Development, 135, 2479-88, 2008
Non Patent Literature 4: Cell, 92, 735-745, 1998
Non Patent Literature 5: Nature Reviews Cancer, 8, 880-887, 2008
Non Patent Literature 6: Nature, 478, 399-403, 2011

SUMMARY OF INVENTION

Technical Problem

The present invention has been achieved in view of these circumstances, and a technical problem to be solved is to provide a novel antibody against VEGF that inhibits binding of a vascular endothelial growth factor (VEGF) to neuropilin-1 (NRP1).

Solution to Problem

As a result of intensive studies to solve the above technical problem, the present inventors have prepared an antibody that inhibits binding of VEGF to NRP1, discovered that the antibody inhibits the physiological action of VEGF, and thus completed the present invention.
Specifically, the present invention is as follows.
(1) An antibody against VEGF that inhibits binding of a vascular endothelial growth factor (VEGF) to neuropilin-1 (NRP1).
(2) An antibody against VEGF that inhibits binding of a vascular endothelial growth factor (VEGF) to neuropilin-1 (NRP1) and of VEGF to vascular endothelial growth factor receptor-2 (VEGFR2).
(3) An antibody against VEGF that inhibits binding of a vascular endothelial growth factor (VEGF) to neuropilin-1 (NRP1) and of VEGF to vascular endothelial growth factor receptor-1 (VEGFR1).
(4) An antibody against VEGF that inhibits binding of a vascular endothelial growth factor (VEGF) to neuropilin-1 (NRP1), of VEGF to vascular endothelial growth factor receptor-2 (VEGFR2) and of VEGF to vascular endothelial growth factor receptor-1 (VEGFR1).
(5) The antibody according to any one of (1) to (4) above, wherein the antibody is a monoclonal antibody.
(6) An antibody that binds to a site to which the antibody according to any one of (1) to (5) above binds.
(7) The antibody according to (5) or (6) above, wherein the antibody is a chimeric antibody or a humanized antibody.
(8) The antibody according to any one of (1) to (7) above, comprising CDR-H1 that comprises the amino acid sequence of SEQ ID NO: 14, CDR-H2 that comprises the amino acid sequence of SEQ ID NO: 16, and CDR-H3 that comprises the amino acid sequence of SEQ ID NO: 18.
(9) The antibody according to any one of (1) to (7) above, comprising CDR-L1 that comprises the amino acid sequence of SEQ ID NO: 20, CDR-L2 that comprises the amino acid sequence of Glu-Gly-Asn, and CDR-L3 that comprises the amino acid sequence of SEQ ID NO: 22.
(10) The antibody according to any one of (1) to (7) above, comprising: CDR-H1 that comprises the amino acid sequence of SEQ ID NO: 14, CDR-H2 that comprises the amino acid sequence of SEQ ID NO: 16, and CDR-H3 that comprises the amino acid sequence of SEQ ID NO: 18; and CDR-L1 that comprises the amino acid sequence of SEQ ID NO: 20, CDR-L2 that comprises the amino acid sequence of Glu-Gly-Asn, and CDR-L3 that comprises the amino acid sequence of SEQ ID NO: 22.
(11) The antibody according to (10) above, further comprising an amino acid sequence derived from a human IgG1 heavy chain constant region and an amino acid sequence derived from a human IgG1 light chain constant region.
(12) The antibody according to (11) above, wherein the amino acid sequence derived from a human IgG1 heavy chain constant region comprises the amino acid sequence of SEQ ID NO: 36, and the amino acid sequence derived from a human IgG1 light chain constant region comprises the amino acid sequence of SEQ ID NO: 38.
(13) The antibody according to (12) above, comprising:
a heavy chain that comprises the amino acid sequence of SEQ ID NO: 24 and the amino acid sequence of SEQ ID NO: 36; and
a light chain that comprises the amino acid sequence of SEQ ID NO: 26 and the amino acid sequence of SEQ ID NO: 38.
(14) The antibody according to (10) above, further comprising an amino acid sequence derived from a canine IgGB heavy chain constant region and an amino acid sequence derived from a canine Ig light chain (κ chain) constant region.
(15) The antibody according to (14) above, wherein the amino acid sequence derived from a canine IgGB heavy chain constant region comprises the amino acid sequence of SEQ ID NO: 40, and the amino acid sequence derived from a canine Ig light chain (κ chain) constant region comprises the amino acid sequence of SEQ ID NO: 42.
(16) The antibody according to (15) above, comprising:
a heavy chain that comprises the amino acid sequence of SEQ ID NO: 24 and the amino acid sequence of SEQ ID NO: 40; and
a light chain that comprises the amino acid sequence of SEQ ID NO: 26 and the amino acid sequence of SEQ ID NO: 42.
(17) A fragment of the antibody according to any one of (1) to (16) above.
(18) The fragment according to (17) above, wherein the fragment is an antigen-binding fragment.
(19) The fragment according to (18) above, wherein the antigen-binding fragment is a single-chain antibody or a double-chain antibody.
(20) A hybridoma that produces the monoclonal antibody according to (5) above.
(21) A pharmaceutical composition comprising the antibody or the fragment thereof according to any one of (1) to (19) above.
(22) The pharmaceutical composition according to (21) above, for use in treatment or prevention of a cancer or a VEGF-mediated eye disease.
(23) The pharmaceutical composition according to (22) above, wherein the treatment or prevention of the cancer or the VEGF-mediated eye disease is by inhibiting binding of a vascular endothelial growth factor (VEGF) to neuropilin-1 (NRP1).
(24) The pharmaceutical composition according to (22) above, wherein the treatment or prevention of the cancer or the VEGF-mediated eye disease is by inhibiting angiogenesis or vascular hyperpermeability.
(25) The pharmaceutical composition according to (24) above, wherein the angiogenesis is pathological angiogenesis.
(26) The pharmaceutical composition according to (22) above, wherein the cancer is solid cancer or hematologic neoplasm.
(27) The pharmaceutical composition according to (22) above, wherein the cancer is at least one selected from the group consisting of brain tumor, cervical cancer, esophageal cancer, cancer on the tongue, lung cancer, breast cancer, pancreatic cancer, gastric cancer, cancer of small bowel, duodenal cancer, colon cancer, bladder cancer, renal cancer, liver cancer, prostate cancer, uterine cancer, uterine cervix cancer, ovarian cancer, thyroid cancer, gallbladder cancer, pharyngeal cancer, sarcoma, melanoma, leukemia, lymphoma, and multiple myeloma.
(28) The pharmaceutical composition according to (22) above, wherein the VEGF-mediated eye disease is at least one selected from the group consisting of age-related macular degeneration, diabetic retinopathy, diabetic macular edema, neovascular glaucoma, retinal vein occlusion, retinopathy of prematurity, choroidal neovascularization associated with pathological myopia, pterygium, rubeosis, pannus, Stevens-Johnson syndrome, and an immunological rejection in a transplanted tissue of the eye.

(29) An angiogenesis inhibitor comprising the antibody or the fragment thereof according to any one of (1) to (19) above.

(30) A reagent comprising the antibody or the fragment thereof according to any one of (1) to (19) above.

(31) A kit comprising the antibody or the fragment thereof according to any one of (1) to (19) above.

(32) A method for treating or preventing a cancer or a VEGF-mediated eye disease, comprising a step of administering to a subject a therapeutically effective amount of the antibody or the fragment thereof according to any one of (1) to (19) above.

(33) The antibody or the fragment thereof according to any one of (1) to (19) above, for use in a method for treating or preventing a cancer or a VEGF-mediated eye disease.

(34) The antibody or the fragment thereof according to any one of (1) to (19) above, for use in the manufacture of a medicament for treatment or prevention of a cancer or a VEGF-mediated eye disease.

Advantageous Effects of Invention

According to the present invention, a novel antibody against VEGF that inhibits binding of a vascular endothelial growth factor (VEGF) to neuropilin-1 (NRP1) can be provided.

BRIEF DESCRIPTION OF DRAWINGS

FIG. 1 shows the receptor-binding domains of $VEGF_{165}$ and $VEGF_{121}$.

FIG. 2 shows the analysis result of the antibody of present invention for its capability of inhibiting binding of VEGF to NRP1.

FIG. 3 shows the analysis result of the antibody of present invention for its capability of inhibiting binding of VEGF to VEGFR2.

FIG. 4 shows the analysis result of the antibody of present invention for its capability of inhibiting binding of VEGF to VEGFR1.

FIG. 5 shows the results of examining the inhibiting effect of KLHc161, that is the antibody of the present invention, on cell proliferation.

FIG. 6 shows the results of examining the inhibiting effect of KLHc161, that is the antibody of the present invention, on cell proliferation.

FIG. 7 shows the results of examining the in vivo inhibiting effect of KLHc161, that is the antibody of the present invention, on tumor growth.

FIG. 8 shows the schedule of a test using a mouse laser-induced choroidal neovascularization (CNV) model.

FIG. 9 shows the results of examining the inhibiting effect of KLHc161, that is the antibody of the present invention, on angiogenesis in the CNV model.

FIG. 10 shows the results of examining the inhibiting effect of KLHc161HC, that is the humanized chimeric antibody of the present invention, on tumor growth.

FIG. 11 shows the results of examining the cross-reactivity of KLHc161CC, that is the caninized chimeric antibody of the present invention, to human and canine VEGF.

FIG. 12 shows the results of examining the in vivo inhibiting effect of KLHc161CC, that is the caninized chimeric antibody of the present invention, on tumor growth in a human cell line.

FIG. 13 shows the results of examining the in vivo inhibiting effect of KLHc161CC, that is the caninized chimeric antibody of the present invention, on tumor growth in a canine cell line.

FIG. 14 shows the results of examining KLHc161HC, that is the humanized chimeric antibody of the present invention, for the capability of binding to VEGF165, VEGF121 and VEGF165b.

DESCRIPTION OF EMBODIMENTS

The present invention will be described in detail as follows. The following embodiments are merely examples for describing the present invention, and are not intended to limit the present invention only to these embodiments. The present invention can be implemented in various modes without departing from the scope of the invention. Moreover, this description includes the contents as disclosed in the specification and drawings of Japanese Patent Application (Japanese Patent Application No. 2016-001275) filed on Jan. 6, 2016, which is priority document of the present application.

1. Summary

The present invention relates to an antibody against VEGF that inhibits binding of a vascular endothelial growth factor (VEGF) to neuropilin-1 (NRP1).

Bevacizumab known as an anti-VEGF neutralizing antibody is an antibody that inhibits binding of VEGF to VEGFR1 and of VEGF to VEGFR2, but does not inhibit binding of VEGF to NRP1. Further, as antibodies that inhibit binding of VEGF to NRP1, antibodies against NRP1 are known, but antibodies against VEGF are not known.

To solve this, the present inventors have developed antibodies against VEGF inhibiting binding of VEGF to NRP1. Furthermore, the present inventors have discovered, in addition to that the antibody inhibits binding of VEGF to NRP1, that the antibody inhibits binding of VEGF to vascular endothelial growth factor receptor-2 (VEGFR2) and binding of VEGF to vascular endothelial growth factor receptor-1 (VEGFR1). Moreover, the present inventors have focused on the fact that NRP1 plays an important role in VEGF-mediated angiogenesis and control of cancer stem cells, and thus discovered that an antibody against VEGF that inhibits binding of VEGF to NRP1 is effective for treatment or prevention of cancer, VEGF-mediated eye diseases, and other diseases due to pathological angiogenesis or vascular hyperpermeability. The present invention has been completed on the basis of these findings.

2. Vascular Endothelial Growth Factor (VEGF)

VEGFs are proteins playing an important role in angiogenesis. VEGFs involve cell division and migration, induction of differentiation, vascular hyperpermeability, activation of monocytes and macrophages, and the like through binding to their receptors to cause intracellular signal transduction.

In the present invention, examples of VEGF include VEGF-A, VEGF-B, VEGF-C, VEGF-D, VEGF-E, PlGF-1, and PlGF-2, and a preferable example thereof is VEGF-A.

VEGF in the present invention may be derived from any mammal. Examples of such a mammal include mice, rats, rabbits, goats, dogs, monkeys and humans, preferably, mice, rats, dogs and humans.

Examples of human VEGF-A include VEGF ($VEGF_{165}$) consisting of 165 amino acid residues, a subtype thereof; that is, VEGF ($VEGF_{121}$) consisting of 121 amino acid residues, VEGF ($VEGF_{145}$) consisting of 145 amino acid residues, VEGF ($VEGF_{183}$) consisting of 183 amino acid residues, VEGF (VEGF$_{189}$) consisting of 189 amino acid residues, VEGF (VEGF$_{206}$) consisting of 206 amino acid residues, VEGF (VEGF$_{165b}$) differing from the above VEGF$_{165}$ in the amino acid sequence of the C-terminal region, and naturally-occurring allelic variants thereof and processing variants thereof. In the present invention, as examples of human VEGF-A, VEGF$_{121}$ and VEGF$_{165}$ are preferred. VEGF is encoded on chromosome 6p12, and the mRNA is 16,272 bp long. VEGF is consisting of exons 1 to 5, and 6a, 6b, 7a, 7b, 8a and 8b. VEGF$_{165}$ binds to all of NRP1, VEGFR1 and VEGFR2.

Furthermore, examples of canine VEGF include, but are not limited to, VEGF (VEGF$_{164}$) consisting of 164 amino acid residues, VEGF (VEGF$_{120}$) consisting of 120 amino acid residues, VEGF (VEGF$_{144}$) consisting of 144 amino acid residues, VEGF (VEGF$_{147}$) consisting of 147 amino acid residues, VEGF (VEGF$_{162}$) consisting of 162 amino acid residues, VEGF (VEGF$_{182}$) consisting of 182 amino acid residues, VEGF (VEGF$_{188}$) consisting of 188 amino acid residues, VEGF (VEGF$_{205}$) consisting of 205 amino acid residues, VEGF (VEGF$_{164b}$) differing from the above VEGF$_{164}$ in the amino acid sequence of the C-terminal region, and naturally occurring allelic variants thereof and processing variants thereof.

In the present invention, the amino acid sequences of mouse, rat, canine and human VEGFs, and VEGF$_{121}$ and VEGF$_{165}$ are represented by SEQ ID NOS: 2, 4, 6, 8, 10, and 12, respectively. Moreover, the base (nucleotide) sequences of DNA encoding mouse, rat, canine and human VEGFs, and VEGF$_{121}$ and VEGF$_{165}$ are represented by SEQ ID NOS: 1, 3, 5, 7, 9 and 11, respectively. These amino acid sequences and nucleotide sequences are each registered in the GenBank database under given Accession Nos.

Mouse VEGF amino acid sequence: NP_001020421.2 (SEQ ID NO: 2) Rat VEGF amino acid sequence: NP_114024.2 (SEQ ID NO: 4) Canine VEGF amino acid sequence: NP_001003175 (SEQ ID NO: 6) Human VEGF-A amino acid sequence: NP_001020537.2 (SEQ ID NO: 8) VEGF$_{121}$ amino acid sequence: ABO26344.1 (SEQ ID NO: 10) VEGF$_{165}$ amino acid sequence: AAM03108.1 (SEQ ID NO: 12) Mouse VEGF-encoding DNA nucleotide sequence: NM_001025250.3 (SEQ ID NO: 1) Rat VEGF-encoding DNA nucleotide sequence: NM_031836.2 (SEQ ID NO: 3) Canine VEGF-encoding DNA nucleotide sequence: NM_001003175.2 (SEQ ID NO: 5) Human VEGF-A-encoding DNA nucleotide sequence: NM_001025366.2 (SEQ ID NO: 7) VEGF$_{121}$-encoding DNA nucleotide sequence: EF424789.1 (SEQ ID NO: 9) VEGF$_{165}$-encoding DNA nucleotide sequence: AF486837.1 (SEQ ID NO: 11)

VEGFs to be used in the present invention include the following proteins (a) to (c):
(a) a protein comprising the amino acid sequence represented by SEQ ID NO: 2, 4, 6, 8, 10 or 12;
(b) a protein comprising an amino acid sequence on which one or several amino acids are deleted, substituted or added with respect to the amino acid sequence represented by SEQ ID NO: 2, 4, 6, 8, 10 or 12, and having binding activity to a VEGF receptor; and
(c) a protein comprising an amino acid sequence that has 80% or higher homology (identity) with the amino acid sequence represented by SEQ ID NO: 2, 4, 6, 8, 10 or 12, and having binding activity to a VEGF receptor.

In the present invention, examples of "a protein comprising the amino acid sequence represented by SEQ ID NO: 2, 4, 6, 8, 10 or 12" include a protein consisting of the amino acid sequence represented by SEQ ID NO: 2, 4, 6, 8, 10 or 12.

Furthermore, examples of "an amino acid sequence on which one or several amino acids are deleted, substituted or added with respect to the amino acid sequence represented by SEQ ID NO: 2, 4, 6, 8, 10 or 12" include:
(i) an amino acid sequence on which 1 to 10 (for example, 1 to 5, preferably 1 to 3, more preferably 1 to 2, and further preferably 1) amino acids are deleted with respect to the amino acid sequence represented by SEQ ID NO: 2, 4, 6, 8, 10 or 12;
(ii) an amino acid sequence on which 1 to 10 (for example, 1 to 5, preferably 1 to 3, more preferably 1 to 2, and further preferably 1) amino acids are substituted with other amino acids with respect to the amino acid sequence represented by SEQ ID NO: 2, 4, 6, 8, 10 or 12;
(iii) an amino acid sequence on which 1 to 10 (for example, 1 to 5, preferably 1 to 3, more preferably 1 to 2, and further preferably 1) amino acids are added with respect to the amino acid sequence represented by SEQ ID NO: 2, 4, 6, 8, 10 or 12; and (iv) an amino acid sequence mutated as a combination of (i) to (iii) above.

In the present invention, the term "VEGF receptor" refers to neuropilin-1 (NRP1), vascular endothelial growth factor receptor-1 (VEGFR1 (another name: Flt-1)) or vascular endothelial growth factor receptor-2 (VEGFR2 (another name: KDR)). Moreover, the term "binding activity to a VEGF receptor" means activity of specifically binding to a VEGF receptor. The presence or the absence of the binding activity can be determined using a known method, such as immunological techniques including immunoprecipitation, Western blotting, EIA (enzyme immunoassay), ELISA (enzyme-linked immunosorbent assay) and the like or pull-down assay. Furthermore, the term "binding activity to a VEGF receptor" means having at least 10% or more, 20% or more, 30% or more, 40% or more, 50% or more, 60% or more, 70% or more, 80% or more, and preferably 90% or more activity, when compared to the activity of the protein consisting of the amino acid sequence represented by SEQ ID NO: 2, 4, 6, 8, 10 or 12, which is set to 100%.

Furthermore, examples of VEGF in the present invention include, in addition to a protein having the amino acid sequence represented by SEQ ID NO: 2, 4, 6, 8, 10 or 12, a protein having an amino acid sequence that has 80% or more homology (identity) with the amino acid sequence represented by SEQ ID NO: 2, 4, 6, 8, 10 or 12, and having binding activity to a VEGF receptor. Examples of such a protein also include a protein having an amino acid sequence that has about 80% or more, 85% or more, 90% or more, 95% or more, 96% or more, 97% or more, 98% or more, or 99% or more homology with the amino acid sequence represented by SEQ ID NO: 2, 4, 6, 8, 10 or 12, and having binding activity to a VEGF receptor (an amino acid sequence substantially equivalent to the amino acid sequence represented by SEQ ID NO: 2, 4, 6, 8, 10 or 12). Homology can be determined using a homology search site on the Internet, for example, by performing a homology search program such as FASTA, BLAST, PSI-BLAST or the like on the DNA Data Bank of Japan (DDBJ). Homology search can also be performed using BLAST on the National Center for Biotechnology Information (NCBI).

Mutagenesis of DNA encoding the relevant protein in order to prepare a protein having the above mutation can be performed using a kit for mutagenesis using site-directed mutagenesis such as Kunkel method, Gapped duplex method or the like, such as QuikChange™ Site-Directed Mutagenesis Kit (Stratagene), GeneTailor™ Site-Directed Mutagenesis System (Invitrogen), TaKaRa Site-Directed Mutagenesis System (Mutan-K, Mutan-Super Express Km and the like: Takara Bio) or the like. Moreover, a method such as a site-directed mutagenesis method described in "Molecular Cloning, A Laboratory Manual (4th edition)" (Cold Spring Harbor Laboratory Press (2012)) can be used.

3. Antibody Against VEGF

In the present invention, the term "antibody against VEGF" (hereafter, also referred to as "anti-VEGF antibody".) refers to an antibody that specifically binds to the above VEGF. The anti-VEGF antibody of the present invention inhibits binding of VEGF to NRP1. Furthermore, the anti-VEGF antibody of the present invention inhibits binding of VEGF to NRP1 and of VEGF to VEGFR2, and binding of VEGF to NRP1 and of VEGF to VEGFR1. Furthermore, the anti-VEGF antibody of the present invention inhibits binding of VEGF to NRP1, of VEGF to VEGFR2 and of VEGF to VEGFR1.

As an additional remark, bevacizumab (Avastin®) that is well known as an anti-VEGF antibody inhibits binding of VEGF to VEGFR1 and of VEGF to VEGFR2, but does not inhibit binding of VEGF to NRP1.

In the present invention, the term "inhibit binding of VEGF to NRP1 and of VEGF to VEGFR2" means that the antibody of the present invention binds to VEGF, resulting in the inhibition of binding of VEGF to NRP1 and of VEGF to VEGFR2. The same applies to the terms "inhibit binding of VEGF to NRP1 and of VEGF to VEGFR1" and "inhibit binding of VEGF to NRP1, of VEGF to VEGFR2 and of VEGF to VEGFR1".

In the present invention, the term "inhibit binding" does not always means 100% inhibition of the binding of VEGF to the VEGF receptor (NRP1, VEGFR2 or VEGFR1). The antibody of the present invention inhibits binding of VEGF to the VEGF receptor, for example, 50% or more, preferably 60% or more, 70% or more, 80% or more, 90% or more, 95% or more, 96% or more, 97% or more, 98% or more, and 99% or more thereof.

An inhibiting effect on the binding can be evaluated using a known method for a binding inhibition test, such as a method used in Example 2 of the Description.

The antibody of the present invention may be a polyclonal antibody or a monoclonal antibody, and is preferably a monoclonal antibody.

The antibody of the present invention is a neutralizing antibody that neutralizes VEGF activity through its specific binding to VEGF. In the present invention, the term "specifically bind to" means binding to (reacting with) a target molecule, but substantially not binding (not reacting with) molecules other than the target molecule. Furthermore, in the present invention, the term "neutralize" at least means to inhibit (suppress) the activity of VEGF to bind to NRP1, VEGFR2 and/or VEGFR1. Whether or not binding is specific can be confirmed by immunological techniques, such as ELISA, Western blot method or immunohistological staining.

Hereafter, a method for preparing an anti-VEGF antibody is described.

(1) Preparation of Antigen

VEGF is used as an immunogen for preparing the antibody of the present invention.

When VEGF is used as an immunogen, a peptide comprising an amino acid sequence that is a portion of the full length sequence of VEGF can also be used. VEGF to be used as an antigen or an immunogen and methods for introducing mutations are as described in the above "2. VEGF".

VEGF may be natural VEGF purified from a mouse, rat, dog, or human tissues or cells, for example, or VEGF produced via genetic engineering techniques. For example, a biological sample confirmed to contain VEGF is fractionated into a soluble fraction and an insoluble fraction using various surfactants, such as Triton-X or Sarkosyl. The insoluble fraction is further dissolved in urea, guanidine hydrochloride or the like, and allow to bind to various columns, such as a heparin column or a binding resin, so that VEGF can be obtained. Moreover, VEGF to be used as an antigen can also be synthesized by specifying the amino acid sequence and then using a known protein synthesis method such as a solid phase method or a commercially available protein synthesizer. A synthesized peptide is bound to a carrier protein such as Keyhole Limpet Hemocyanin (KLH) or thyroglobulin and thus the resultant can be used as an immunogen.

(2) Preparation of Polyclonal Antibody

The above-prepared VEGF or a partial peptide alone is administered or the same is administered together with a carrier, a diluent or the like to a non-human mammal, such as a rabbit, a dog, a guinea pig, a mouse, a rat, or a goat for immunization. The dosage of the antigen per animal ranges from 0.1 mg to 10 mg when an adjuvant is used. Examples of the adjuvant include Freund's complete adjuvant (FCA), Freund's incomplete adjuvant (FIA), and an aluminum hydroxide adjuvant. Immunization is performed by mainly intravenous, subcutaneous, intraperitoneal injection, or the like. Furthermore, the immunization interval is not particularly limited, and immunization is performed at intervals of several days to several weeks, and preferably at intervals of 1 to 2 weeks for 2 to 10 times and preferably 3 to 5 times. The immunization interval can be determined by persons skilled in the art considering the resulting antibody titer. Preferably, blood is sampled when subcutaneous immunization is performed 3 to 4 times and then the antibody titer is measured. Antibody titer in serum can be measured by ELISA (enzyme-linked immunosorbent assay), EIA (enzyme immunoassay), radioimmunoassay (RIA) or the like. After confirmation of a sufficient increase in antibody titer, whole blood is collected, and then an antibody can be separated and purified by a generally employed method. Regarding separation and purification, a known method such as an ammonium sulfate salting-out method, ion exchange chromatography, gel filtration chromatography, and affinity chromatography is adequately selected or combined, and then purification can be performed. As a specific example, a serum containing a target antibody is applied to a column to which proteins other than VEGF have been bound, a flow-through fraction is collected, and then a polyclonal antibody having improved specificity to VEGF can be obtained.

(3) Preparation of Monoclonal Antibody (i) Collection of Antibody-Producing Cells In a manner similar to that for preparation of a polyclonal antibody, VEGF or a partial peptide alone or the same together with a carrier or a diluent is administered to a non-human mammal for immunization. The dosage of an antigen per animal, the type of an adjuvant to be used, an immunization method, and immunization intervals are similar to those for preparation of a polyclonal antibody. One to 30 days, and preferably 2 to 5 days after the final immunization date, individuals confirmed to have antibody titers are selected, and then antibody-producing cells are collected. Examples of antibody-producing cells include spleen cells, lymph node cells, and peripheral blood cells, and among them spleen cells or lymph node cells are preferred.

(ii) Cell Fusion

To obtain hybridomas, cell fusion of antibody-producing cells and myeloma cells is performed. Cell fusion procedures can be implemented according to a known method such as the method of Kohler et al. As myeloma cells to be fused to antibody-producing cells, generally available established cell lines of an animal such as a mouse can be used. Cell lines that can be preferably used herein have drug selectivity and have a property of being unable to survive in HAT selective medium (containing hypoxanthine, aminopterin, and thymidine) when the cells are in an unfused state, but able to survive only in a state fused to antibody-producing cells. Examples of myeloma cells include mouse myeloma cell lines such as P3-x63-Ag8U.1, SP2/O—Ag14, PAI, P3U1, NSI/1-Ag4-1, and NSW, and rat myeloma cell lines such as YB2/0.

The cell fusion of myeloma cells and antibody-producing cells described above is performed by mixing $1 \times 10^8$ to $5 \times 10^8$ antibody-producing cells and $2 \times 10^7$ to $10 \times 10^7$ myeloma cells in animal cell culture medium such as serum-free DMEM and RPMI-1640 medium (the cell ratio of antibody-producing cells to myeloma cells ranges from 10:1 to 1:1), and then performing fusion reaction in the presence of a cell fusion accelerator. As a cell fusion accelerator, polyethylene glycol having an average molecular weight of 1000-6000 daltons or Sendai virus can be used, for example. In addition, antibody-producing cells and myeloma cells can be fused using a commercially available cell fusion device utilizing electrical stimulation (for example, electroporation).

(iii) Hybridoma Selection and Cloning

A target hybridoma is selected from cells after cell fusion treatment. Such a method is performed by appropriately diluting a cell suspension with 10% to 20% fetal calf serum-containing RPMI-1640 medium or the like, placing the resultant on a microtiter plate at about 0.3 cells/well as calculated by a limiting dilution method, adding selective medium such as HAT medium to each well, and then culturing while appropriately exchanging selective media. As a result, cells that grow around 10 days after the start of culture in selective media can be obtained as hybridomas.

Next, hybridomas that have grown are further screened. Hybridoma screening may be performed according to a general method and is not particularly limited. For example, a portion of a culture supernatant contained in wells in which hybridomas have been cultured is collected and then can be screened by enzyme immunoassay, radioimmunoassay or the like. As a specific example, an antigen is adsorbed to a 96-well plate, followed by blocking with calf serum. The culture supernatant of hybridoma cells is reacted with an immobilized antigen at 37° C. for 1 hour, and then reacted with peroxidase-labeled anti-mouse IgG at 37° C. for 1 hour, for color development using orthophenylenediamine as a substrate. The reaction is stopped with acid, and then absorbance at a wavelength of 490 nm is measured, so that screening can be performed. Hybridomas producing a monoclonal antibody found positive as a result of the above measurement method is cloned by a limiting dilution method or the like. Finally, hybridomas that are cells producing the monoclonal antibody that specifically binds to VEGF are established.

(iv) Collection of Monoclonal Antibody

As a method for collecting a monoclonal antibody from the thus established hybridomas, a general cell culture method, an ascites formation method, or the like can be employed. According to a cell culture method, the hybridomas are cultured in animal cell culture medium such as 10% fetal calf serum-containing RPMI-1640 medium, MEM, or serum free medium under general culture conditions (for example, 37° C., 5% $CO_2$ concentration) for 7 to 14 days, and then an antibody is obtained from the culture supernatant. According to an ascites formation method, about $5 \times 10^6$ to $2 \times 10^7$ hybridomas are administered intraperitoneally to an animal of the same species as that of a mammal from which myeloma cells are derived, such as mouse (BALB/c), so that hybridomas are grown in large amounts. One to 2 weeks later, ascites is collected. When the above method for collecting an antibody requires purification of the antibody, purification can be performed by appropriately selecting a known method such as an ammonium sulfate salting-out method, ion exchange chromatography, gel filtration, and affinity chromatography, or using these methods in combination.

Examples of the antibody of the present invention include, but are not limited to, an antibody wherein:

a heavy chain variable region (VH) comprises a heavy chain complementarity determining region (CDR)1 (CDR-H1) comprising or consisting of the amino acid sequence represented by SEQ ID NO: 14, heavy chain CDR2 (CDR-H2) comprising or consisting of the amino acid sequence represented by SEQ ID NO: 16, and/or heavy chain CDR3 (CDR-H3) comprising or consisting of the amino acid sequence represented by SEQ ID NO: 18; and/or a light chain variable region (VL) comprises light chain CDR1 (CDR-L1) comprising or consisting of the amino acid sequence represented by SEQ ID NO: 20, light chain CDR2 (CDR-L2) comprising or consisting of the amino acid sequence that consists of glutamic acid (E)-glycine (G)-asparagine (N) (may also be referred to as "amino acid sequence EGN" or "amino acid sequence Glu-Gly-Asn"), and/or light chain CDR3 (CDR-L3) comprising or consisting of the amino acid sequence represented by SEQ ID NO: 22. Moreover, in another aspect, examples of the antibody of the present invention include, but are not limited to, an antibody wherein the amino acid sequence of a heavy chain variable region comprises or consists of the amino acid sequence represented by SEQ ID NO: 24, and/or the amino acid sequence of a light chain variable region comprises or consists of the amino acid sequence represented by SEQ ID NO: 26.

(4) Preparation of Recombinant Antibody

A preferred aspect of the antibody of the present invention is a recombinant antibody. Examples of the recombinant antibody include, but are not limited to, a chimeric antibody, a humanized antibody, and a caninized antibody.

A chimeric antibody refers to an antibody prepared by linking immunoglobulin gene fragments of animals of different species. In the present invention, examples of a chimeric antibody include a humanized chimeric antibody, and a caninized chimeric antibody, but the types of animals, from which chimeric antibody variable and constant regions are derived, are not limited. A humanized chimeric antibody is an antibody prepared by linking (joining) a mouse-derived antibody variable region to a human-derived constant region, for example (see Proc. Natl. Acad. Sci. U.S.A. 81, 6851-6855, (1984), for example). A caninized chimeric antibody is an antibody prepared by linking a mouse-derived antibody variable region to a dog-derived constant region, for example. When a chimera is prepared, this can be easily constructed by gene recombination techniques so that an antibody prepared through such ligation can be obtained.

Here, examples of a mouse-derived antibody variable region include, but are not limited to, a heavy chain variable region comprising or consisting of the amino acid sequence represented by SEQ ID NO: 24, and a light chain variable region comprising or consisting of the amino acid sequence represented by SEQ ID NO: 26.

When a humanized antibody is prepared, a technique referred to as, namely, CDR grafting, can be employed. CDR grafting is a method for preparing a reconstructed variable region, whereby a complementarity determining region (CDR) is grafted from a mouse antibody variable region to a human variable region, so that the framework region (FR) is human-derived and CDR is mouse-derived. Next, such humanized reconstructed human variable region is ligated to a human constant region. Such a method for preparing a humanized antibody is known in the art (see e.g., Nature, 321, 522-525 (1986); J. Mol. Biol., 196, 901-917 (1987); Queen C et al., Proc. Natl. Acad. Sci. USA, 86: 10029-10033 (1989); and Japanese Patent No. 2828340). Here, examples of the amino acid sequence of mouse-derived CDR, which can be used for the humanized antibody of the present invention include, but are not limited to, CDR1-3 of a heavy chain variable region (CDR-H1, CDR-H2 and CDR-H3), comprising or consisting of the amino acid sequences represented by SEQ ID NO: 14, 16 and 18, respectively, CDR1-3 of a light chain variable region (CDR-L1, CDR-L2 and CDR-L3) comprising or consisting of the amino acid sequence represented by SEQ ID NO: 20, the amino acid sequence that consists of glutamic acid (E)-glycine (G)-asparagine (N) (amino acid sequence Glu-Gly-Asn), and the amino acid sequence represented by SEQ ID NO: 22, respectively.

A caninized antibody can also be prepared by a technique similar to the above method for preparing a humanized antibody.

In the present invention, examples of a human heavy chain constant region that can be used for a chimeric antibody and a humanized antibody include, but are not limited to, a human heavy chain constant region comprising an amino acid sequence derived from a human IgG1 heavy chain constant region, and for example, a human heavy chain constant region comprising or consisting of the amino acid sequence represented by SEQ ID NO: 36. Moreover, examples of a human light chain constant region that can be used for a chimeric antibody and a humanized antibody include, but are not limited to, a human light chain constant region comprising an amino acid sequence derived from a human IgG1 light chain constant region, and for example, a human light chain constant region comprising or consisting of the amino acid sequence represented by SEQ ID NO: 38. Furthermore, examples of DNA encoding a human heavy chain constant region include, but are not limited to, DNA comprising or consisting of the nucleotide sequence represented by SEQ ID NO: 35. Examples of DNA encoding a human light chain constant region include, but are not limited to, DNA comprising or consisting of the nucleotide sequence represented by SEQ ID NO: 37.

Furthermore, in the present invention, examples of a canine heavy chain constant region that can be used for a chimeric antibody and a caninized antibody include, but are not limited to, a canine heavy chain constant region comprising an amino acid sequence derived from the canine IgGB heavy chain constant region, and for example, a canine heavy chain constant region comprising or consisting of the amino acid sequence represented by SEQ ID NO: 40. Moreover, examples of a canine light chain constant region that can be used for a chimeric antibody and a caninized antibody include, but are not limited to, a canine light chain constant region comprising an amino acid sequence derived from a canine Ig light chain (κ chain) constant region, and for example, a canine light chain constant region comprising or consisting of the amino acid sequence represented by SEQ ID NO: 42. Moreover, examples of DNA encoding a canine heavy chain constant region include, but are not limited to, DNA comprising or consisting of the nucleotide sequence represented by SEQ ID NO: 39. Examples of DNA encoding a canine light chain constant region include, but are not limited to, DNA comprising or consisting of the nucleotide sequence represented by SEQ ID NO: 41.

In the present invention, a chimeric antibody, a humanized antibody, and a caninized antibody can be prepared according to the above-mentioned known method using a hybridoma or DNA, RNA or the like extracted from the hybridoma as a raw material.

Furthermore, the antibody of the present invention in the form of a fusion protein can be prepared according to a known gene recombination technique using antibody variable regions and another protein. The fusion protein can also be prepared by cross-linking a monoclonal antibody and another protein using a cross-linker.

(5) Preparation of Antibody Fragment

A fragment of the antibody against VEGF to be used in the present invention specifically binds to VEGF.

An antibody fragment refers to a polypeptide containing a partial region of the antibody of the present invention. As an antibody fragment, an antigen-binding fragment is preferred. Examples of the antigen-binding fragment include, but are not limited to, single-chain antibodies (scFv (single chain Fv), sc (Fv)$_2$), double-chain antibodies (Fab, Fab', diabody (diabody (dibodies), dsFv), and F(ab')$_2$. The above antibody fragment can be obtained by cleaving the antibody of the present invention with various proteases depending on purposes.

For example, Fab can be obtained by treating an antibody molecule with papain, and F(ab')$_2$ can be obtained by treating an antibody molecule with pepsin. Moreover, Fab' can be obtained by cleaving the disulfide bond of the above F(ab')$_2$ hinge region.

In the case of scFv, cDNA encoding antibody H chain V region and L chain V region is obtained and then DNA encoding scFv is constructed. The DNA is inserted into an expression vector, and then the expression vector is introduced into a host organism for expression, so that scFv can be produced.

In the case of a diabody, cDNA encoding antibody H chain V region and L chain V region is obtained, and then DNA encoding scFv is constructed so that a peptide linker has an amino acid sequence with a length of 8 or less residues. The DNA is inserted into an expression vector, and then the expression vector is introduced into a host organism for expression, so that a diabody can be produced.

In the case of dsFv, cDNA encoding antibody H chain V region and L chain V region is obtained, and then DNA encoding dsFv is constructed. The DNA is inserted into an expression vector, and then the expression vector is introduced into a host organism for expression, so that dsFv can be produced.

In the present invention, examples of the nucleotide sequence of DNA encoding a heavy chain variable region include, but are not limited to, DNA comprising or consisting of the nucleotide sequence represented by SEQ ID NO: 23, and examples of the nucleotide sequence of DNA encoding a light chain variable region include, but are not limited to, DNA comprising or consisting of the nucleotide sequence represented by SEQ ID NO: 25.

Furthermore, specific examples of the antibody fragment of the present invention include, for example, an antibody fragment comprising:
a heavy chain variable region (VH) comprises heavy chain CDR1 (CDR-H1) comprising or consisting of the amino acid sequence represented by SEQ ID NO: 14, heavy chain CDR2 (CDR-H2) comprising or consisting of the amino acid sequence represented by SEQ ID NO: 16, and/or heavy chain CDR3 (CDR-H3) comprising or consisting of the amino acid sequence represented by SEQ ID NO: 18; and/or a light chain variable region (VL) comprises light chain CDR1 (CDR-L1) comprising or consisting of the amino acid sequence represented by SEQ ID NO: 20, light chain CDR2 (CDR-L2) comprising or consisting of the amino acid sequence that consists of glutamic acid (E)-glycine (G)-asparagine (N) (amino acid sequence Glu-Gly-Asn), and/or light chain CDR3 (CDR-L3) comprising or consisting of the amino acid sequence represented by SEQ ID NO: 22. Another example of the antibody fragment includes, but are not limited to, an antibody fragment in which VH comprises or consists of the amino acid sequence represented by SEQ ID NO: 24 and/or VL comprises or consists of the amino acid sequence represented by SEQ ID NO: 26.

An antibody fragment (peptide) comprising CDR is composed of at least one region of VH or VL CDRs (CDR1-3). An antibody fragment comprising a plurality of CDRs can be bound directly or via an appropriate peptide linker. An antibody fragment comprising CDR can be produced by constructing DNA encoding antibody VH and VL CDRs, inserting the DNA into a prokaryotic expression vector or a eukaryotic expression vector, and then introducing the expression vector into prokaryotes or eukaryotes for expression. Furthermore, a peptide comprising CDR can also be produced by a chemical synthesis method such as a Fmoc method (fluorenylmethyloxycarbonyl method) and a tBoc method (t-butyloxycarbonyl method).

Examples of DNA encoding VH CDR1-3 include, but are not limited to, DNA comprising or consisting of the nucleotide sequence represented by SEQ ID NO: 13, DNA comprising or consisting of the nucleotide sequence represented by SEQ ID NO: 15 and DNA comprising or consisting of the nucleotide sequence represented by SEQ ID NO: 17, respectively. Examples of DNA encoding VL CDR1-3 include, but are not limited to, DNA comprising or consisting of the nucleotide sequence represented by SEQ ID NO: 19, DNA comprising or consisting of the nucleotide sequence that consists of guanine (G)-adenine (A)-adenine (A)-guanine (G)-guanine (G)-cytosine (C)-adenine (A)-adenine (A)-thymine (T) (also referred to as "nucleotide sequence GAAGGCAAT"), and DNA comprising or consisting of the nucleotide sequence represented by SEQ ID NO: 21, respectively.

(6) Binding Affinity

Binding affinity can be determined by the binding constant (KA) and dissociation constant (KD). Affinity equilibrium constant (K) is expressed by the ratio of the KA/KD. Its binding affinity can be detected as follows.

Binding constant (KA) and dissociation constant (KD) can be measured using surface plasmon resonance (SPR), and known devices and methods for detecting binding rates in real time and monitoring can be employed (e.g. Biacore®-3000 (GE Healthcare), ProteON XPR36 (Bio-Rad), etc.).

The present invention provides an antibody that binds to a site to which the antibody against VEGF of the present invention binds. In detail, the antibody against VEGF of the present invention includes an antibody that binds to a site to which any one of the following antibodies binds: (i) an antibody against VEGF that inhibits binding of VEGF to NRP1; (ii) an antibody against VEGF that inhibits binding of VEGF to NRP1 and of VEGF to VEGFR2; and (iii) an antibody against VEGF that inhibits binding of VEGF to NRP1, of VEGF to VEGFR2 and of VEGF to VEGFR1.

A site to which the anti-VEGF antibody of the present invention binds is not limited, as long as it is at least a partial region of VEGF that is an antigen. Examples of a site to which the anti-VEGF antibody of the present invention binds include, at least one region selected from the group consisting of exon 1, 2, 3, 4, 5, 6a, 6b, 7a, 7b, and 8a, and exon 1 to 5 regions are preferred. Persons skilled in the art can specify exon 1 to 5 regions of various VEGFs based on known information such as Genbank. For example, the amino acid sequences of mouse, rat, canine, human VEGF exon 1 to 5 are represented by SEQ ID NO: 43, 44, 45 and 46, respectively.

Persons skilled in the art can specify sites (e.g., regions and epitopes) or polypeptides containing them, to which the anti-VEGF antibody of the present invention binds, based on the Description and known techniques such as epitope mapping or X-ray structural analysis.

Furthermore, an antibody that binds to a site, to which any one of the above antibodies (i) to (iii) binds, may be a polyclonal antibody or a monoclonal antibody. When such an antibody is a monoclonal antibody, the antibody may be a recombinant antibody, such as a chimeric antibody, a humanized antibody, or a caninized antibody.

An antibody that binds to a site, to which the antibody against VEGF of the present invention binds, competes with the antibody against VEGF of the present invention for binding with VEGF. Persons skilled in the art can understand that an antibody competing with the antibody against VEGF of the present invention for binding with VEGF has specificity and/or activity equivalent to that of the antibody of the present invention (specifically, the above antibodies (i) to (iii)).

A competition test using an antibody is a technique established in the technical field of antibodies as a technique for examining if a set of antibodies bind to the same (or redundant) site (see e.g., Ju-Won Kwak et al., Journal of Immunological Methods 191 (1996) 49-54). In the competition test, when the binding of the antibody against VEGF of the present invention is competitively inhibited by an anti-VEGF antibody to be tested, the test subject anti-VEGF antibody can be identified to be an antibody that binds to a site, to which the antibody against VEGF of the present invention binds. Furthermore, the test method does not require information about the structure of the relevant site for examining if a set of antibodies bind to the same (or redundant) site.

Namely, persons skilled in the art can obtain an antibody binding to a site, to which the antibody against VEGF of the present invention binds, by conducting a competition test using the antibody against VEGF of the present invention without excessive experimentation.

4. Pharmaceutical Composition

The pharmaceutical composition of the present invention comprises the antibody or a fragment thereof described in the above "3. Antibody against VEGF" as an active ingredient, and is used for a target disease. The pharmaceutical composition of the present invention is used for prevention or treatment of target diseases and is effective for the prevention or the treatment.

Diseases targeted by the pharmaceutical composition of the present invention are not limited, as long as they are VEGF-associated diseases (including symptoms (conditions)), and examples of such diseases include solid tumors, cancers including particularly problematic metastatic tumors, and VEGF-mediated eye diseases, and other immune diseases.

Tumor vascular structures are known to supply blood, and also function as a vascular niche environment supporting cancer stem cells. For example, it has been demonstrated that deletion of an NRP1 gene, Nrp1, inhibits VEGF's capability to accelerate tumorigenesis (Nature, 478, p. 399-403, 2011). The vascular niche environment refers to an environment involving maintenance, proliferation and differentiation of hematopoietic stem cells that are sources of blood and blood vessels, and is considered to be important for cancer stem cell proliferation.

Unlike normal cells, cancer cells are characterized by high proliferative ability, unlimited number of cell divisions, and ability to cause invasion and metastasis to peripheral tissues. In recent years, it has become considered that not all cancer cells in a cancer tissue have such properties, and limited partial cells have such properties. Specifically, these partial cancer cells are cells having properties observed in common among stem cells such as embryonic stem cells and somatic stem cells, including self-replicating ability, by which the cells can create cells completely identical thereto, and pluripotency, by which the cells are capable of differentiating into many cell types. The partial cancer cells are considered to be cancer stem cells that function as a source for creating the majority of peripheral cancer cells via differentiation while maintaining cells identical to themselves in the cancer tissue through self-replication.

Cancer stem cells are considered to be a major cause of cancer recurrence and cancer metastasis, and thus importance of targeting cancer stem cells in cancer treatment has been indicated. If inhibition with superiority of cancer stem cell proliferation within tumor tissue becomes possible, a novel treatment capable of killing entire cancer cells effectively can be developed. It has been suggested that binding of VEGF to NRP1 may regulate the sternness of cancer stem cells in skin squamous cell carcinoma. Accordingly, such an antibody that inhibits binding to NRP1 among antibodies binding to VEGF may exert a therapeutic effect more significant than that of conventional anti-VEGF antibodies represented by bevacizumab.

The term "cancer sternness" in the present invention refers to a property of a cell population exerting the properties of cancer stem cells. Specifically, cancer sternness refers to properties of having self-replication and pluripotency peculiar to stem cells, and a property of cells functioning as a source of cancer.

In the present invention, examples of cancer include brain tumor, cervical cancer, esophageal cancer, cancer on the tongue, lung cancer, breast cancer, pancreatic cancer, gastric cancer, cancer of small bowel, duodenal cancer, colon cancer, bladder cancer, renal cancer, liver cancer, prostate cancer, uterine cancer, uterine cervix cancer, ovarian cancer, thyroid cancer, gallbladder cancer, pharyngeal cancer, sarcoma, melanoma, leukemia, lymphoma, and multiple myeloma.

In the present invention, VEGF-mediated eye disease is VEGF-associated disease that is caused by pathological angiogenesis or vascular hyperpermeability in the eye. That is, the VEGF-mediated eye disease can be treated or prevented by inhibiting binding of VEGF to a VEGF receptor using the anti-VEGF antibody. Examples of such disease include age-related macular degeneration (including special types such as polypoidal choroidal vasculopathy and retinal angiomatous proliferation), diabetic retinopathy, diabetic macular edema, neovascular glaucoma, retinal vein occlusion, retinopathy of prematurity, choroidal neovascularization associated with pathological myopia, pterygium, rubeosis, pannus, Stevens-Johnson syndrome, and immunological rejection of transplanted tissue (e.g., corneal tissue) of the eye.

In the present invention, the term "pathological angiogenesis" refers to angiogenesis that takes place, in morbidity or a state inducing morbidity, when new blood vessels grow excessively, insufficiently, or inappropriately (for example, the position or timing, is undesirable from a medical viewpoint of vasculogenesis, or in development) compared with normal physiological angiogenesis (vasculogenesis).

In the present invention, the term "treatment", "treat", or "treating" refers to contacting (for example, administrating) the antibody or a fragment thereof or the pharmaceutical composition of the present invention (hereafter, may also be referred to as "the pharmaceutical composition of the present invention or the like") with a subject after the onset of the disease, thereby alleviating the symptoms of the disease, compared to when the subject is not contacted with the pharmaceutical composition of the present invention or the like. The treatment as used herein does not always refer to completely suppressing the symptoms of a disease. The term "onset of a disease" refers to the appearance of the symptoms of the disease in the body.

In the present invention, the term "prevention", "prevent", or "preventing" refers to contacting (for example, administrating) the pharmaceutical composition of the present invention or the like with a subject before the onset of a disease, thereby alleviating symptoms of the disease after the onset of the disease, compared to when the subject is not contacted with the pharmaceutical composition of the present invention or the like. The term "prevention" does not always refer to completely suppressing the onset of the disease.

The pharmaceutical composition of the present invention can comprise, in addition to the antibody against VEGF of the present invention, a pharmaceutically acceptable carrier. The term "pharmaceutically acceptable carrier" refers to any carrier (e.g., liposome, lipid microcapsule, and micelle), diluent, excipient, wetting agent, buffering agent, suspending agent, lubricant, adjuvant, emulsifier, disintegrator, absorbent, preservative, surfactant, colorant, flavoring, or sweetener appropriate for the pharmaceutical composition for immune diseases.

The pharmaceutical composition of the present invention or the like can be formulated into preparations for injection, freeze-dried products, tablets, hard capsules, soft capsules, granules, powders, pills, syrups, suppositories, cataplasm, ointments, cream pharmaceuticals, eye drops, and the like. Liquid preparations such as preparations for injection may be in the form of powder to be prepared before use (for example, freeze-dried powder), which is dissolved in saline or the like before use.

The pharmaceutical composition of the present invention or the like can be administered topically or systemically through any means known by persons skilled in the art. The route of administration of the pharmaceutical composition of the present invention can be oral administration and parenteral administration. In the case of parenteral administration, intratissue administration (e.g., subcutaneous administration, intraperitoneal administration, intramuscular administration, and intravenous administration), intradermal administration, local administration (e.g., transdermal administration) or transrectal administration can be performed. The pharmaceutical composition of the present invention can be administered in dosage forms appropriate for these routes of administration.

The dosage of the pharmaceutical composition of the present invention or the like can be varied depending on factors such as a subject's age, body weight, health status, gender, and symptoms, and the animal species of a subject, the route of administration, the frequency of administration, and a dosage form, and specific procedures for administration can be determined by persons skilled in the art. The dosage of the antibody of the present invention for treatment of cancer ranges from, for example, 0.1 mg to 100 mg/day, preferably 1 mg to 15 mg/day, and more preferably 2 mg to 12 mg/day per kg body weight of a subject, but the examples are not limited thereto. Regarding the frequency of administration, the pharmaceutical composition can be administered once to 5 times a day. The dosage of the antibody of the present invention for treatment of VEGF-mediated eye disease ranges from, for example, 0.01 mg to 100 mg/eye, and more preferably, 0.1 mg to 10 mg/eye. Regarding the frequency of administration, the antibody can be administered once a day to once every two months, but the examples are not limited thereto.

The timing of administration can be appropriately determined depending on symptoms, and several dosages can be administered simultaneously or separately at intervals. Furthermore, the pharmaceutical composition of the present invention may be administered to a subject before the onset of a disease or after the onset of the disease.

The pharmaceutical composition of the present invention can be administered to a mammal as a subject. Examples of mammals include mice, rats, hamsters, guinea pigs, rabbits, cats, dogs, goats, pigs, sheep, cattle, horses, monkeys, and humans.

5. Method for Treating or Preventing a Cancer or a VEGF-Mediated Eye Disease

According to the present invention, a cancer or a VEGF-mediated eye disease can be treated or prevented by administrating to a subject the antibody against VEGF or a fragment thereof or the pharmaceutical composition comprising the same. That is, the present invention provides a method for treating or preventing a cancer or a VEGF-mediated eye disease, comprising a step of administering to a subject a therapeutically effective amount of the antibody of the present invention or a fragment thereof or the pharmaceutical composition comprising the same. The therapeutically effective amount of the antibody of the present invention or a fragment thereof or the pharmaceutical composition comprising the same is varied depending on factors such as a subject's age, body weight, health status, gender, and symptoms, the route of administration, the frequency of administration, and a dosage form. Persons skilled in the art can easily determine the therapeutically effective amount required for treatment or prevention of a cancer or a VEGF-mediated eye disease. In the present invention, "subject" includes subjects in need of treatment or prevention of a cancer or a VEGF-mediated eye disease. In addition, mammals to be subjected to treatment or prevention as "subject" are as described above.

In the method for treating or preventing a cancer or a VEGF-mediated eye disease of the present invention, "cancer", "VEGF-mediated eye disease", "treatment" and "prevention" are as described above. Moreover, the dosage form, the route of administration, the dosage, the timing of administration and the like of the antibody of the present invention or a fragment thereof or the pharmaceutical composition comprising the same are also as described above.

6. Angiogenesis Inhibitor

The antibody of the present invention inhibits binding of VEGF to a VEGF receptor, and thus can inhibit angiogenesis resulting from the binding. That is, the present invention provides an angiogenesis inhibitor comprising the antibody or a fragment thereof described in the above "3. Antibody against VEGF" as an active ingredient.

The angiogenesis inhibitor of the present invention can be used as a reagent or used for treatment of a mammal, and its dosage form, additives, route of administration, administration target, dosage and the like can be appropriately selected according to the description of the above "4. Pharmaceutical composition". However, the angiogenesis inhibitor of the present invention may be an inhibitor comprising the antibody of the present invention or a fragment thereof alone.

7. Use of Antibody

The antibody of the present invention or a fragment thereof can be used in a method for treating or preventing a cancer or a VEGF-mediated eye disease, or the manufacture of a medicament for treatment or prevention of a cancer or a VEGF-mediated eye disease. That is, the present invention provides the anti-VEGF antibody of the present invention or a fragment thereof for use in the method for treating or preventing a cancer or a VEGF-mediated eye disease. Moreover, the present invention provides the anti-VEGF antibody of the present invention or a fragment thereof for use in the manufacture of a medicament for treatment or prevention of a cancer or a VEGF-mediated eye disease. Furthermore, the present invention provides the anti-VEGF antibody or a fragment thereof for use in the manufacture of an angiogenesis inhibitor.

In these aspects, "cancer", "VEGF-mediated eye disease", "treatment" and "prevention" are as described above.

8. Combination Therapy

The pharmaceutical composition of the present invention can be used for administration in combination with at least one of other anticancer agents. Examples of anticancer agents to be used in the present invention include sorafenib (Nexavar®), sunitinib (Sutent®), bevacizumab (Avastin®), cisplatin (cDDP), carboplatin (Paraplatin®), paclitaxel (Taxol®), docetaxel (Taxotere®), gemcitabine hydrochloride (Gemzar®), gefitinib (Iressa®), erlotinib (Tarceva®), irinotecan hydrochloride (CPT-11), and 5-fluorouracil (5-FU).

It can be expected that combined administration of the pharmaceutical composition of the present invention and at least one of anticancer agents exert more advantageous effects than an independent use thereof. Such advantageous effects include an effect alleviating adverse effects more than conventional therapies while maintaining the therapeutic effects.

The term "used in combination" in the present invention refers to simultaneous administration of or separate administration of the pharmaceutical composition of the present invention and at least one of the above anticancer agents. The term "simultaneously" means that administration is performed at the same timing in a single administration schedule, but the times; that is, hours and minutes of administration are not required to be completely the same. The term "separately" means that administration is performed at different timings in a single administration schedule.

The dosage form, the route of administration, and the administration target of the pharmaceutical composition or the like and an anticancer agent to be used for combination therapy in the present invention are not particularly limited, and can be appropriately selected according to the description of the above "4. Pharmaceutical composition". Moreover, the dosage forms or dosages of agents to be used in combination may differ from each other, and can be appropriately adjusted depending on a combination employed.

When the pharmaceutical composition of the present invention is used in combination with another anticancer agent, the dosage can be decreased as appropriate. Therefore, when the pharmaceutical composition of the present invention is combined with another anticancer agent, the following combinations of
(i) an effective dose of the pharmaceutical composition of the present invention and an effective dose of another anticancer agent,
(ii) an effective dose of the pharmaceutical composition of the present invention and a subeffective dose of another anticancer agent,
(iii) a subeffective dose of the pharmaceutical composition of the present invention and an effective dose of another anticancer agent, and
(iv) a subeffective dose of the pharmaceutical composition of the present invention and a subeffective dose of another anticancer agent can be employed.

Even in an aspect in which one of or both the pharmaceutical composition and an anticancer agent are used in subeffective doses, the two can be administered in combination in such an aspect, when the combination can exert pharmacological effects.

9. Reagent, Kit

The antibody of the present invention or a fragment thereof can be included in a reagent for detection of VEGF or a kit. That is, the present invention provides a reagent and a kit comprising the antibody of the present invention or a fragment thereof. The reagent and the kit of the present invention can be used as a reagent for detecting VEGF or a kit, for example.

In the reagent and the kit of the present invention, the antibody of the present invention or a fragment thereof may be treated by a method such as freezing for easy handling, and then directly or mixed with a known pharmaceutically acceptable carrier, such as an excipient, an extending agent, a binder, and a lubricant, and a known additive (including a buffering agent, a tonicity agent, a chelating agent, a colorant, a preservative, an aroma chemical, a flavoring agent, a sweetening agent and the like), for example.

The kit of the present invention can comprise, in addition to the antibody of the present invention or a fragment thereof, a buffer, an enzyme solution, a secondary antibody, a solution for dilution, instructions, and the like.

Hereafter, the present invention is described in detail by Examples, but the present invention is not limited to the Examples.

Example 1

Preparation of Monoclonal Antibody
(1) Preparation of Antigen

Human recombinant $VEGF_{165}$ (hereafter, may also be referred to as "VEGF", "$rhVEGF_{165}$" or "rhVEGF") expressed by CHO cells (PROSPEC) was used as an antigen. For the purpose of suppressing the effect of VEGF on mice, an antigen bound to KLH (Keyhole Limpet Hemocyanin) was prepared. In this case, VEGF and KLH were mixed so that the molar ratio of VEGF to KLH was 4:1 in PBS (−) (0.01 M sodium-phosphate buffer, 0.138 M NaCl, 0.0027 M KCl, pH 7.4), and then 1% glutaraldehyde was added, and then the mixture was allowed to react at room temperature for 1 hour, thereby cross-linking KLH and $rhVEGF_{165}$. The thus prepared protein may also be referred to as "KLH-VEGF" in the followings.

(2) Immunization rhVEGF or KLH-VEGF and Freund's complete adjuvant were mixed in equal amounts, and then the mixture was administered intraperitoneally to BALB/c mice in an amount of 100 µl (about 40 µg/mouse). After about 3 weeks, rhVEGF and Freund's incomplete adjuvant were similarly mixed in equal amounts and then the mixture was administered intraperitoneally. This procedure was repeated 7 to 12 times, and then increases in antibody titer were confirmed. Mice confirmed to exert increased titers were subjected to final immunization through intravenous administration of about 40 µg of rhVEGF or KLH-VEGF, and then 3 days later, the spleens were extracted.

(3) Cell Fusion

Isolated splenocytes and a mouse myeloma cell line, P3-x63-Ag8U. 1 (DS PHARMA BIOMEDICAL), were mixed at 5:1 in terms of the number of cells, and then cell fusion was performed using 50% polyethylene glycol 3350 (Sigma). Cells were suspended in HAT medium (RPMI1640 medium supplemented with ½×HT (MP), ½×HAT (MP), 10% FBS, 50 ng/L mouse IL-6, and 500 mg/mL D-Glucose), dispensed in a 96-well microculture plate and then cultured.

(4) ELISA

Culture supernatants of wells in which hybridomas had grown were collected, and then hybridomas producing monoclonal antibodies reactive to $rhVEGF_{165}$ were selected. $rhVEGF_{165}$ was diluted with PBS (−), dispensed into a 96-well ELISA plate (Nunc) at 1 µg/well, allowed to stand overnight at 4° C., and thus bound onto the plate surface. Next, after 3 times of washing with 350 µL of 0.05% Tween 20-containing PBS (−) (hereafter, denoted as "PBS-T"), 300 µL of 1% skim milk-containing PBS-T was dispensed into each well, followed by blocking at room temperature for 1 hour. After washing with PBS-T, the culture supernatant of the hybridomas was dispensed into an ELISA plate on which $rhVEGF_{165}$ had been immobilized, and then allowed to react for 1 hour at room temperature. After washing with PBS-T, 100 µL of peroxidase (hereafter, denoted as "POD")-labeled anti-mouse immunoglobulin antibody (BETHYL) diluted 10000-fold was dispensed into each well, and then allowed to react for 1 hour at room temperature. After similar washing was performed, a POD substrate that had been prepared to a concentration of 1 mg/mL POD was added, and then the resultant was allowed to develop color at room temperature for 5 minutes. The reaction was stopped with 1.5 N sulfuric acid, and then absorbance at 490 nm was measured using a plate reader (Molecular Devices).

(5) Establishment of Anti-VEGF Monoclonal Antibody

Based on the absorbance of a plate to which no $rhVEGF_{165}$ had been immobilized, wells each found to have an absorbance three or more times the baseline value were determined to be positive, and then cloning was performed by a limiting dilution method. Cell supernatants of wells containing single colonies were examined for antibody activity by the method of the above (4), isolated, and then cultured, thereby establishing a hybridoma cell line producing a monoclonal antibody reactive to $rhVEGF_{165}$.

Example 2

Evaluation of Monoclonal Antibody
(1) Selection of Monoclonal Antibody Reactive to $rhVEGF_{121}$ With the use of rhVEGF (hereafter, may also be referred to as "$rhVEGF_{121}$") (HUMANZYME) expressed by human 293 cells, monoclonal antibodies produced by the thus obtained hybridoma cells were evaluated by the method described in Example 1 (4). The binding domain of VEGF165 to NRP1 is known to be a Heparin binding domain corresponding to exon 7 and the C-terminal region corresponding to exon 8a. VEGF121 lacks the Heparin binding domain that is an NRP1 binding domain. A schematic diagram produced on the basis of the primary sequence is shown in FIG. 1. VEGF121 has VEGFR1 and VEGFR2 binding domains but lacks the Heparin binding domain that is an NRP1 binding domain and thus an antibody that binds to VEGF121 binds to exon 1, 2, 3, 4, 5 or 8a of VEGF165. In order to obtain an antibody that binds to a region that is not a NRP1 binding domain, but inhibits binding of NRP1 and VEGF, clones strongly reacting to rhVEGF121 were selected from among monoclonal antibodies produced by the thus obtained hybridoma cells.

(2) Purification of Monoclonal Antibody

To analyze if the above-selected monoclonal antibodies produced by hybridoma cells inhibit binding of VEGF to VEGFR1, of VEGF to VEGFR2 and of VEGF to NRP1, the monoclonal antibodies produced by hybridoma cells were purified. Hybridoma cells were cultured to 90% confluence per 10-cm dish, and then cultured for 10 days in medium prepared by mixing HT medium (Invitrogen) and EX CELL Sp2/0 (Nichirei Biosciences) at 1:1. The culture supernatant was collected, and then purified using a Protein G column. 0.1 mL of the Protein G column (GE Healthcare) was used for 20 mL of the culture supernatant. The culture solution was allowed to pass through the Protein G column equilibrated with PBS at a flow rate of 1 ml/min to 3 ml/min, and then washed with 2 mL of washing buffer (25 mM Tris-HCl (pH 7.4), 140 mM NaCl, 10 mM KCl). Next, 0.5 mL of elution buffer (0.1 M Glycine (pH 2.5)) was used for elution of the antibody protein, and then the resultant was neutralized using 3 M Tris-HCl (pH 7.4) so that the pH ranged from 7.0 to 7.4. Amicon Ultra 30 (Millipore) was used to concentrate the antibody and the buffer was substituted with PBS.

(3) HRP Labeling of Anti-Mouse Polyclonal Antibody

Antisera were collected from mice immunized in the above Example 1 (2), and then a fraction containing the anti-VEGF polyclonal antibody was prepared. Immunized mice were anesthetized using diethyl ether, and then blood was collected from the heart. Collected blood was centrifuged at 12000 rpm for 10 minutes at 4° C., supernatants containing no blood cell were collected as antisera. From the antisera, a mouse IgG antibody was purified by a method similar to that of (2) above, and then HRP labeling was performed using an HRP Labeling Kit (DOJINDO) (hereafter, the HRP-labeled polyclonal antibody may also be referred to as "anti-VEGF polyclonal antibody-HRP label").

(4) Binding Inhibition Test on Binding of VEGF to NRP1

Monoclonal antibodies produced by hybridoma cells obtained in Example 1 were analyzed for their inhibition of binding of VEGF to NRP1. Recombinant Human Neuropilin-1 (R&D Systems) (hereafter, may also be referred to as "NRP1") was diluted with PBS (−), added to a 96-well ELISA plate at 0.5 µg per well, allowed to stand at room temperature for 2 hours, and thus immobilized onto the plate surface. Next, after washing using 0.1% Tween 20-containing TBS (50 mM Tris-HCl, pH 7.4, 500 mM NaCl) (hereafter, may also be referred to as "TBS-T"), 2% Bovine Serum Albumin (hereafter, may also be referred to as "BSA")-containing TBS-T was added at 300 µL per well, and then the resultant was allowed to stand at room temperature for 1 hour for blocking. Separately, 100 µL of Recombinant Human Vascular Endothelial Growth Factor, CHO (Prospec) (hereafter, may also be referred to as "rhVEGF") diluted with PBS (−) to a concentration of 10 µg/mL and 100 µL of the monoclonal antibody (monoclonal antibody produced by hybridoma cells obtained in Example 1) diluted with PBS (−) to a concentration of 34.1 µg/mL were mixed, followed by reaction at 37° C. for 1 hour. The solution was added to a plate to which NRP1-Fc had been immobilized, allowed to react at room temperature for 1 hour, and then washed with TBS-T. Another monoclonal antibody (clone No. KLHa1527) was diluted with 1% BSA-containing TBS-T to a concentration of 5 µg/mL, and then added at 100 µL per well, followed by reaction at room temperature for 1 hour. After washing with TBS-T, peroxidase-labeled anti-mouse IgG antibody (Bethyl) diluted 5000-fold with 1% BSA-containing TBS-T was added at 100 µL per well, and then allowed to react at room temperature for 30 minutes. After washing with TBS-T, signals were detected using TMB ELISA Substrates (Invitrogen). The absorbance measured using a mouse IgG isotype control (BD) was regarded as 100%, and the inhibiting effect resulting from addition of the monoclonal antibody was evaluated. As an additional remark, the above clone No. KLHa1527 was not thought to inhibit binding of VEGF to a receptor, and thus was used for quantitating VEGF bound to a receptor.

As a result, a plurality of anti-VEGF antibodies that inhibit binding of VEGF to NRP1 were obtained (FIG. 2). Of these antibodies, particularly clone No. KLHc161 monoclonal antibody significantly inhibited binding of VEGF to NRP1.

That is, in this Example, the anti-VEGF antibody that inhibits binding of VEGF to NRP1 was obtained.

Furthermore, binding of VEGF to NRP1 is considered to regulate the sternness of cancer stem cells (Nature, 478, 399-403, 2011), and NRP1 is considered to involve cancer cell proliferation. Hence, the antibody of the present invention that inhibits binding of VEGF to NRP1 is useful in treatment or prevention of cancer.

(5) Binding Inhibition Test on Binding of VEGF to VEGFR2

The monoclonal antibodies produced by hybridoma cells obtained in Example 1 were analyzed for their inhibition of binding of VEGF to VEGFR2. Recombinant Human VEGF R2/KDR/Flk-1 Fc Chimera (R&D Systems) (hereafter, may also be referred to as "VEGFR2-Fc") was diluted with PBS (−), added to a 96-well ELISA plate at 0.5 µg per well, allowed to stand at room temperature for 2 hours, and thus immobilized onto the plate surface. Next, after washing with 0.1% Tween 20-containing TBS (50 mM Tris-HCl, pH 7.4, 500 mM NaCl) (hereafter, may also be referred to as "TBS-T"), 1% Bovine Serum Albumin (hereafter, may also be referred to as "BSA")-containing TBS-T was added at 300 µL per well, and then the resultant was allowed to stand at room temperature for 1 hour for blocking. Separately, 100 µL of Recombinant Human Vascular Endothelial Growth Factor, CHO (Prospec) (hereafter, may also be referred to as "rhVEGF") diluted with PBS (−) to a concentration of 5 µg/mL, and 100 µL of the monoclonal antibody (the monoclonal antibody produced by hybridoma cells obtained in Example 1) diluted with PBS (−) to a concentration of 80 µg/mL were mixed, followed by reaction at 37° C. for 1 hour. The solution was added to a plate to which VEGFR2-Fc had been immobilized, allowed to react at room temperature for 1 hour, and then washed with TBS-T. Anti-VEGF antibody (HRP) (Abcam) was diluted 200-fold with 1% BSA-containing TBS-T, added at 100 µL per well, and then allowed to react at room temperature for 1 hour. After washing with TBS-T, signals were detected using TMB ELISA Substrates (Invitrogen). The absorbance found using a mouse IgG isotype control (BD) was regarded as 100%, and the inhibiting effect resulting from the addition of the monoclonal antibody was evaluated.

As a result, a plurality of anti-VEGF antibodies that inhibit binding of VEGF to VEGFR2 were obtained (FIG. 3). Furthermore, since these anti-VEGF antibodies also include an antibody that inhibits binding of VEGF to NRP1 (for example, clone No. KLHc161), the result demonstrates that antibodies that inhibit binding of VEGF to NRP1 as well as inhibit binding of VEGF to VEGFR2 were obtained.

That is, in this Example, the anti-VEGF antibodies that inhibit binding of VEGF to NRP1 and of VEGF to VEGFR2 were obtained.

(6) Binding Inhibition Test on Binding of VEGF to VEGFR1

The monoclonal antibodies produced by hybridoma cells obtained in Example 1 were analyzed for the inhibition of binding of VEGF to VEGFR1. Recombinant Human VEGF R1/Flt-1 Fc Chimera (R&D Systems) (hereafter, may also be referred to as "VEGFR1-Fc") was diluted with PBS (−), added to a 96-well ELISA plate at 0.3 µg/well, allowed to stand at room temperature for 3 hours, and thus immobilized onto the plate surface. Next, after washing with 0.1% Tween 20-containing TBS (50 mM Tris-HCl, pH 7.4, 500 mM NaCl) (hereafter, may also be referred to as "TBS-T"), 1% Bovine Serum Albumin (hereafter, may also be referred to as "BSA")-containing TBS-T was added at 300 µL per well, and then allowed to stand at room temperature for 1 hour for blocking. Separately, 100 µL of Recombinant Human Vascular Endothelial Growth Factor, CHO (Prospec) (hereafter, may also be referred to as "rhVEGF") diluted with PBS (−) to a concentration of 1 µg/mL and 100 µL of the monoclonal antibody (the monoclonal antibody produced by hybridoma cells obtained in Example 1) diluted with PBS (−) to a concentration of 5 µg/mL were mixed, followed by reaction at 37° C. for 1 hour. The solution was added to a plate to which VEGFR1-Fc had been immobilized, allowed to react at room temperature for 1 hour, and then washed with TBS-T. Anti-VEGF antibody (HRP) (Abcam) was diluted 200-fold with 1% BSA-containing TBS-T, added at 100 µL per well, and then allowed to react at room temperature for 1 hour. After washing with TBS-T, signals were detected using TMB ELISA Substrates (Invitrogen). The absorbance found using a mouse IgG isotype control (BD) was regarded as 100%, and the inhibiting effect resulting from the addition of the monoclonal antibody was evaluated.

As a result, a plurality of anti-VEGF antibodies that inhibit binding of VEGF to VEGFR1 were obtained (FIG. 4). Furthermore, since these anti-VEGF antibodies include an antibody that inhibit binding of VEGF to NRP1 and of VEGF to VEGFR2 (for example, clone No. KLHc161), the result demonstrates that antibodies that inhibit binding of VEGF to NRP1, binding of VEGF to VEGFR2, and binding of VEGF to VEGFR1 were obtained.

That is, in this Example, the anti-VEGF antibody that inhibits binding of VEGF to NRP1 and of VEGF to VEGFR1, as well as the anti-VEGF antibody that inhibits binding of VEGF to NRP1, of VEGF to VEGFR2 and of VEGF to VEGFR1 were obtained.

Example 3

Inhibiting Effect of Monoclonal Antibody on Cell Proliferation

Clone No. KLHc161 monoclonal antibody was selected from the obtained anti-VEGF antibodies, and then the antibody was analyzed if it inhibited the action of VEGF on normal human umbilical vein-derived endothelial cells (hereafter, may also be referred to as "HUVEC"). HUVEC (BD) was thawed and cultured using attached growth medium to prepare HUVEC in logarithmic growth phase. HUVEC was used in the test to such an extent that the number of passages did not exceed 8. Medium 200 (Invitrogen) containing 1% Fetal Bovine Serum and 1% penicillin-streptomycin (Invitrogen) was used, 5000 cells each were seeded on a 12-well plate, and Recombinant Human Vascular Endothelial Growth Factor, CHO (Prospec) (hereafter, may also be referred to as "rhVEGF") was added at a concentration of 50 ng/mL, thereby continuing culture. Upon evaluation, simultaneously with the initiation of culture, a cell group to which rhVEGF had been added at a concentration of 50 ng/mL, or a cell group containing rhVEGF at a concentration of 50 ng/mL and the antibody added at a concentration of 2500 ng/mL was subjected to determination of the number of cells on days 2, 4, 6, and 8 after addition of rhVEGF using a hemocytometer.

The results are shown in FIG. 5. The number of cells was low in the cell group to which the antibody had been added at a concentration of 2500 ng/mL, compared with a positive control to which rhVEGF and mouse IgG isotype control (BD) had been added. Thus, the inhibiting (suppressing) effect of the antibody on cell proliferation was confirmed.

Furthermore, HUVEC in logarithmic growth phase was prepared in the same manner as described above, Medium 200 (Invitrogen) containing 1% Fetal Bovine Serum and 1% penicillin-streptomycin (Invitrogen) was used and 10000 cells each were seeded on a 96-well plate. Recombinant Human Vascular Endothelial Growth Factor, CHO (Prospec) (hereafter, may also be referred to as "rhVEGF") was added at a concentration of 50 ng/mL for continuing culture. The number of cells 24 hours after addition of rhVEGF was determined using a hemocytometer.

The results are shown in FIG. 6. The number of cells was low in the cell group to which the antibody of the present invention had been added at a concentration of 2500 ng/mL, compared with a positive control to which rhVEGF and mouse IgG isotype control (BD) had been added. Thus, the inhibiting effect of the antibody on cell proliferation was confirmed.

It was demonstrated by these results that the antibody of the present invention has the inhibiting effect on cell proliferation.

Example 4

In Vivo Inhibiting Effect of Monoclonal Antibody on Tumor Growth

Human colon cancer cell line LS174T cells were subcutaneously injected at a rate of $2\times10^6$ cells per mouse into the right flanks of 20 immunodeficient mice. On the next day of injection, 0.9% NaCl (control group A) or the anti-VEGF antibody (clone No. KLHc161; control group B) was intraperitoneally administered. The anti-VEGF antibody was administered twice a week to the mice of control group B at 0.5 mg/Kg, 2.5 mg/Kg, or 5 mg/Kg. Furthermore, similarly to the antibody, 0.9% NaCl was administered twice a week to the mice of control group A. After inoculation of cells, tumors were measured on days 1, 5, 9, 16 and 20, and then tumor volumes were calculated using the formula: V ($mm^3$)=$d^2 \times D/2$.

The results are shown in FIG. 7. In FIG. 7, group A (0.9% NaCl control) is denoted with (◇), group B (mice inoculated with the anti-VEGF antibody) is denoted with (□: 0.5 mg/Kg), (Δ: 2.5 mg/Kg), or (○: 5.0 mg/Kg). As shown in FIG. 7, decreases in tumor volume were observed in mice injected with the anti-VEGF antibody.

These results demonstrated that the anti-VEGF antibody of the present invention inhibited (suppressed) the tumor growth even in vivo. Furthermore, this indicated that a pharmaceutical composition comprising the antibody of the present invention is significantly effective in treatment or prevention of cancer.

Example 5

Examination of the Effect on Mouse Laser-Induced Choroidal Neovascularization Model In this Example, to examine the effect of the antibody of the present invention on VEGF-mediated eye disease in vivo, a test was conducted using a mouse laser-induced choroidal neovascularization (CNV) model that is an experimental model of wet-type age-related macular degeneration (wAMD). The mouse laser-induced choroidal neovascularization (CNV) model can be prepared by subjecting choroid to laser-beam coagulation to induce inflammation, and thus to induce angiogenesis from the choroid.

1. Materials and Methods
(1) Antibody

In this Example, an anti-VEGF antibody prepared in Example 1 was used. Specifically, KLHc161 was used as an antibody that inhibits binding of VEGF to NRP1 and of VEGF to VEGFR2.

(2) Preparation of Wet-Type Age-Related Macular Degeneration (wAMD) Model

A mouse laser-induced choroidal neovascularization (CNV) model that is an experimental model of wet-type age-related macular degeneration (wAMD) was prepared by performing photocoagulation at 4 spots (spot size: 50 μm, output: 60 mW, and coagulation time: 0.1 seconds) of the posterior pole of the fundus of each eye of 8-week-old male C57BL/6J mice as a scattered manner, while avoiding thick retinal blood vessels.

(3) Group Configuration

The group configuration is as shown in the following table. In the table below, PBS denotes a negative control.

TABLE 1

| Group No. | Test substance | Route of administration | Number of samples (eyes) |
|---|---|---|---|
| 1 | PBS | Intravitreal administration | 12 eyes of 6 mice |
| 2 | 0.1 μg/eye antibody | Intravitreal administration | 12 eyes of 6 mice |
| 3 | 0.3 μg/eye antibody | Intravitreal administration | 12 eyes of 6 mice |
| 4 | 1 μg/eye antibody | Intravitreal administration | 12 eyes of 6 mice |

(4) Administration of Drug (Intravitreal Administration)

The dosage of an antibody-containing composition in intravitreal administration was 5 μl/eye, and the frequency (number) of administration is one.

(5) Test Schedule

The test schedule is as shown in FIG. 8.

(6) Evaluation Method

Fundus fluorescein angiography was performed for both eyes on day 14 after photocoagulation, and then the fluorescent dye leakage area of a photocoagulation site was measured, thereby finding the choroidal neovascularization (CNV) area.

2. Results

As a result of administration of KLHc161 to the above CNV model, the CNV area was significantly suppressed in the 0.3 μg/eye administration group (FIG. 9). In FIG. 9, #: $p<0.05$ with respect to PBS administration group (Dunnett's multiple comparison test).

The results demonstrate that the antibody of the present invention is also effective in vivo, as an angiogenesis inhibitor, as well as effective against VEGF-mediated eye disease such as age-related macular degeneration.

Example 6

Examination of Monoclonal Antibody Variable Region

The amino acid sequences of the variable regions of the antibody of the present invention and the nucleotide sequences encoding the same were analyzed.

Specifically, the genome sequence of the heavy chain variable region of the hybridoma that produces the anti-VEGF antibody (clone No. KLHc161) was analyzed by sequencing with each of the following primers.

```
                                          (SEQ ID NO: 27)
5'-CTAATACGACTCACTATAGGGCAAGCAGTGGTATCAACGCAGA

GT-3' (sense primer)

(SEQ ID NO: 28)
5'-CCAGGGGCCAGTGGATAGACCGATGGGGCTGTTG-3'

(antisense primer)

and (SEQ ID NO: 29)
5'-CTAATACGACTCACTATAGGGC-3' (sense primer)

(SEQ ID NO: 30)
5'-CCAGGGGCCAGTGGATAGACCGATGGGGCTGTTG-3'

(antisense primer)
```

Furthermore, the genome sequence of the light chain variable region of the hybridoma that produces the antibody was analyzed by sequencing with each of the following primers.

```
                                          (SEQ ID NO: 31)
5'-CTAATACGACTCACTATAGGGCAAGCAGTGGTATCAACGCAGAG

T-3' (sense primer)

(SEQ ID NO: 32)
5'-GCACCTCCAGATGTTAACTGCTCACT-3' (antisense primer)

and (SEQ ID NO: 33)
5'-CTAATACGACTCACTATAGGGC-3' (sense primer)

(SEQ ID NO: 34)
5'-GCACCTCCAGATGTTAACTGCTCACT-3' (antisense primer)
```

Furthermore, the amino acid sequences of CDR1, CDR2 and CDR3 of the antibody variable region were determined using IMGT/V-QUEST software, version 3.3.0, on the immunoglobulin database "the international ImMunoGeneTics information System®" (IMGT/GENE-DB).

The results are shown in the following table.

TABLE 2

| Heavy chain (V-D-J region) | |
|---|---|
| Nucleotide sequence | gaggtccagctgcagcagtctggacctgagctggcaaagcctggggcttcagt gaagatgtcctgcaaggcttctggatacacattcactagctatgttatgcact gggtgaagcagaagcctgggcagggccttgagtggattggatatattaatcct tacaatgatggtgctaagtacaatgagaagttcaaaggcaaggccacactgac ttcagacaaatcctccagcacagcctacatggagctcagcagcctgacctctg aggactctgcggtctattactgtgcaaccttttacttcggtagtagcgacaga gctatggactactgggtcaaggaacctcagtcaccgtctcctcag (SEQ ID NO: 23) |
| Peptide sequence | EVQLQQSGPELAKPGASVKMSCKASGYTFTSYVMHWVKQKPGQGLEWIGYINP YNDGAKYNEKFKGKATLTSDKSSSTAYMELSSLTSEDSAVYYCA (SEQ ID NO: 24) |
| Light chain (V-J region) | |
| Nucleotide sequence | gaaacaactgtgacccagtctccagcatccctgtccatggctataggagaaaa agtcaccatcagatgcataattagcactgatattgatgatgatatgaactggt accagcagaagccaggggaacctcctaagctccttatttcagaaggcaatact cttcgtcctggagtcccatcccgattctccagcagtggctatggtacagattt tgttttacaattgaaaacatgctctcagaagatgttgcagattactactgtt tgcaaagtgataacttgccgtacacgttcggaggggggaccaagctggaaata aaac (SEQ ID NO: 25) |
| Peptide sequence | ETTVTQSPASLSMAIGEKVTIRCIISTDIDDDMNWYQQKPGEPPKLLISEGNT LRPGVPSRFSSSGYGTDFVFTIENMLSEDVADYYCLQSDNLPYTFGGGTKLEI K (SEQ ID NO: 26) |
| Sequence Heavy chain | |
| VH-CDR1 | GYTFTSYV (SEQ ID NO: 14) |
| VH-CDR2 | INPYNDGA (SEQ ID NO: 16) |
| VH-CDR3 | ATFYFGSSDRAMDY (SEQ ID NO: 18) |
| Light chain | |
| VL-CDR1 | TDIDDD (SEQ ID NO: 20) |
| VL-CDR2 | EGN |
| VL-CDR3 | LQSDNLPYT (SEQ ID NO: 22) |

Example 7

Preparation of Human-IgG1 Chimeric KLHc161 Antibody (KLHc161HC)

From the hybridoma that produces the KLHc161 antibody, the KLHc161 antibody heavy chain variable region gene (nucleotide sequence: SEQ ID NO: 23, amino acid sequence: SEQ ID NO: 24) and light chain variable region gene (nucleotide sequence: SEQ ID NO: 25, amino acid sequence: SEQ ID NO: 26) were cloned. Next, these genes were each ligated in-frame to the nucleotide sequence of the human IgG1 heavy chain constant region gene or light chain (κ chain) constant region gene. PCR was carried out using a primer having the 5'-terminal nucleotide sequence of the heavy chain variable region and a restriction enzyme Mlu I sequence and an antisense primer having a complementary sequence of the 3'-terminal nucleotide sequence and a restriction enzyme Nhe I sequence. Next, PCR was carried out using a primer having the 5'-terminal nucleotide sequence of the light chain variable region gene, Kozak sequence, and a restriction enzyme BamH I sequence and an antisense primer having a complementary sequence of the 3'-terminal nucleotide sequence and a restriction enzyme BsiW I sequence. The thus obtained amplification product was treated with restriction enzymes Mlu I and Nhe I or BamH I and BsiW I, and then the resultant was incorporated into the Mlu I-Nhe I site of the human IgG1 heavy chain constant region expression plasmid (pEF6/G1) or the BamH I-BsiW I site of the human IgG1 light chain constant region expression plasmid (pEF1/G1k). In pEF6/G1, the human IgG1 heavy chain constant region gene (nucleotide sequence: SEQ ID NO: 35, amino acid sequence: SEQ ID NO: 36) was cloned into the plasmid pEF6/myc-His (Invitrogen). In pEF1/G1-k, the human IgG1 light chain constant region gene (nucleotide sequence: SEQ ID NO: 37, amino acid sequence: SEQ ID NO: 38) was cloned into the plasmid pEF1/myc-His (Invitrogen). The mouse heavy chain variable region and the human heavy chain constant region were linked by a restriction enzyme Nhe I, and the mouse light chain variable region and the human light chain constant region were linked by a restriction enzyme BsiW I sequence.

The plasmids pEF6/G1-KLHc161 and pEF1/G1-K-KLHc161 were introduced into 293F cells using a FreeStyle™ 293 Expression System (Thermo Fisher Scientific K.K.), and thus the human IgG1 chimeric KLHc161 antibody (hereafter, may also be referred to as "KLHc161HC antibody") was transiently expressed. Next, the KLHc161HC antibody was purified from a culture supernatant of 293F cells, into which the chimeric gene had been introduced, using Protein G Sepharose 4 Fast Flow (GE Healthcare Japan). A solvent was substituted with D-PBS (−) using an Amicon Ultra-15 centrifugal filter unit (Merck millipore). The concentration of the purified KLHc161HC antibody was determined using Nano drop 1000 (Thermo Fisher Scientific K.K.). Binding of the KLHc161HC antibody to VEGF was evaluated by the method described in the above "Purification of monoclonal antibody (4) ELISA". As a result, specific binding of the KLHc161HC antibody to VEGF was confirmed.

That is, in this Example, the chimeric antibody of the anti-VEGF antibody of the present invention was obtained.

Example 8

In Vivo Inhibiting Effect of Human IgG1 Chimeric KLHc161 Antibody (KLHc161HC Antibody) on Tumor Growth Human colon cancer cell line LS174T cells were subcutaneously injected at a rate of $2 \times 10^6$ cells per mouse into the right flanks of the 20 immunodeficient mice. On the next day of injection, 0.9% NaCl (control group A) or KLHc161HC antibody (control group B) was intraperitoneally administered. The KLHc161HC antibody was administered to the mice of control group B twice a week at 0.5 mg/Kg, 2.5 mg/Kg, or 5 mg/Kg. Furthermore, similarly to the antibody, 0.9% NaCl was administered twice a week to the mice of control group A. On days 1, 5, 8, 12, 15, 19 and 22 after inoculation of cells, tumor sizes were measured, and then tumor volumes were calculated using the formula: $V (mm^3) = (d: minor\ axis)^2 \times (D: major\ axis)/2$. The results are shown in FIG. 10. In FIG. 10, group A (0.9% NaCl control) is indicated with (◇), group B (mice injected with the KLHc161HC antibody) is indicated with (□: 0.5 mg/Kg), (△: 2.5 mg/Kg), or (○: 5.0 mg/Kg). As shown in FIG. 10, significant decreases in tumor volume were observed in mice injected with the KLHc161HC antibody. These results demonstrated that the KLHc161HC antibody; that is, a chimeric antibody of the present invention inhibited (suppressed) the tumor growth even in vivo.

This demonstrated that a pharmaceutical composition comprising the human IgG1 chimeric anti-VEGF antibody of the present invention is significantly effective for treatment or prevention of cancer.

Example 9

Preparation of Canine-IgGB Chimeric KLHc161 Antibody (KLHc161CC Antibody)

From the hybridoma that produces the KLHc161 antibody, the KLHc161 antibody heavy chain variable region gene (nucleotide sequence: SEQ ID NO: 23, amino acid sequencer SEQ ID NO: 24) and light chain variable region gene (nucleotide sequence: SEQ ID NO: 25, amino acid sequence: SEQ ID NO: 26) were cloned. Next, these genes were each ligated in-frame to the nucleotide sequence of the canine IgGB heavy chain constant region gene or light chain (κ chain) constant region gene. PCR was carried out using a primer having the 5'-terminal nucleotide sequence of the heavy chain variable region, Kozak sequence, and a restriction enzyme EcoR V sequence, and an antisense primer having a complementary sequence of the 3'-terminal nucleotide sequence and a restriction enzyme Nhe I sequence. Next, PCR was carried out using a primer having the 5'-terminal nucleotide sequence of the light chain variable region gene and a restriction enzyme EcoR I sequence, and an antisense primer having a complementary sequence of the 3'-terminal nucleotide sequence and a restriction enzyme Xho I sequence. The thus obtained amplification product was treated with restriction enzymes Eco V and Nhe I, or EcoR I and Xho I, and then the resultant was incorporated into the EcoR V-Nhe I site of a canine IgGB heavy chain constant region expression plasmid (pFUSE2ss-CHIg-dGB), or the EcoR I-Xho I site of a canine Ig light chain constant region expression plasmid (pFUSE2ss-CHIg-dK). In pFUSE2ss-CHIg-dGB, the canine IgGB heavy chain constant region gene (nucleotide sequence: SEQ ID NO: 39, amino acid sequence: SEQ ID NO: 40) was cloned into plasmid pFUSE2ss-CLIg-h12 (InvivoGen). In pFUSE2ss-CHIg-dK, the canine Ig light chain (κ chain) constant region gene (nucleotide sequence: SEQ ID NO: 41, amino acid sequence: SEQ ID NO: 42) was cloned into plasmid pFUSE2ss-CLIg-h12. The mouse heavy chain variable region and the canine heavy chain constant region were linked by the restriction enzyme Nhe I sequence, and the mouse light chain variable region and the canine light chain constant region were linked by the restriction enzyme Xho I sequence.

Example 10

Cross-Reactivity of Canine-IgGB Chimeric KLHc161 Antibody (KLHc161CC Antibody) to Human VEGF165 and Canine VEGFA Whether or not the thus prepared canine-IgGB chimeric antibody had capability of binding to human VEGF165 and canine VEGFA (VEGF164) was confirmed by ELISA. Human VEGF165 or canine VEGFA were diluted with TBS, dispensed to a 96-well ELISA plate (Nunc) at 20 ng per well, and then incubated at 37° C. for 1 hour for binding to the plate surface. Next, after 3 times of washing with 300 µL of 0.02% Tween 20-containing PBS (−) (hereafter, denoted as "PBS-T"), 300 µL of 3% skim milk-containing PBS (−) was dispensed into each well, followed by blocking at 37° C. for 1 hour. After washing with PBS-T, the canine-IgGB chimeric KLHc161 antibody (KLHc161CC antibody) serially diluted from the concentration of 1 µg/ml was dispensed to an ELISA plate to which VEGF had been immobilized, and then allowed to react at 37° C. for 1 hour. After washing with PBS-T, a peroxidase-labeled anti-canine immunoglobulin antibody (BETHYL) prepared to have a concentration of 100 ng/ml was dispensed at 100 µL per well, and then allowed to react at 37° C. for 1 hour. After washing similarly, TMB Single Solution was added for color development at room temperature. After the reaction was stopped with 1 N sulfuric acid, absorbance at 450 nm was measured using a plate reader (Molecular Devices). The results are shown in FIG. 11. It was demonstrated that the KLHc161CC antibody binds to canine VEGFA with the same degree of affinity as that to human VEGF165.

These results demonstrated that a pharmaceutical composition comprising the canine IgGB chimeric anti-VEGF antibody of the present invention can be used for treatment or prevention of diseases of dogs.

Example 11

In Vivo Inhibiting Effect of Canine IgGB Chimeric KLHc161 Antibody (KLHc161CC Antibody) on Tumor Growth in Human Cancer Cell Line Human colon cancer cell line LS174T cells were subcutaneously injected at a rate of 2×10$^6$ cells per mouse to the right flanks of 20 immunodeficient mice. On the next day of injection, 0.9% NaCl (control group A) or the KLHc161CC antibody (control group B) was administered intraperitoneally. The KLHc161CC antibody was administered twice a week to the mice of control group B at 0.5 mg/Kg, 2.5 mg/Kg, or 5 mg/Kg. Furthermore, similarly to the antibody, 0.9% NaCl was administered twice a week to the mice of control group A. On days 5, 8, 12, 15, 19 and 22 after inoculation of cells, tumor sizes were measured and tumor volumes were calculated using the formula: V (mm$^3$)=(d: minor axis)$^2$×(D: major axis)/2. The results are shown in FIG. 12. In FIG. 12, group A (0.9% NaCl control) is indicated with (■), group B (mice inoculated with the anti-VEGF antibody) is indicated with (●: 0.5 mg/Kg), (▲: 2.5 mg/Kg), or (Δ: 5.0 mg/Kg). As shown in FIG. 12, significant decreases in tumor volume were observed in mice injected with the KLHc161CC antibody.

These results demonstrated that the KLHc161CC antibody of the present invention also inhibits (suppresses) in vivo the growth of human tumors. These results also demonstrated that a pharmaceutical composition comprising the canine IgGB chimeric anti-VEGF antibody of the present invention is significantly effective for treatment or prevention of cancer.

Example 12

In Vivo Inhibiting Effect of Canine IgGB Chimeric KLHc161 Antibody (KLHc161CC Antibody) on Tumor Growth in Canine Cancer Cell Line Canine bone sarcoma cell line D-17 cells were subcutaneously injected at a rate of 1×10$^7$ cells per mouse to the right flanks of 20 immunodeficient mice. After the mean tumor volume reached 150 mm$^3$, 0.9% NaCl (control group A) or the KLHc161CC antibody (control group B) was intraperitoneally administered. The KLHc161CC antibody was administered twice a week to the mice of control group B at 0.5 mg/Kg, 2.5 mg/Kg, or 5 mg/Kg. Similarly to the antibody, 0.9% NaCl was administered twice a week to the mice of control group A. On days 50, 54, 57, 61, 64, 67, 70, 74, 77 and 81 after inoculation of cells, tumor sizes were measured, and the tumor volumes were calculated using the formula: V (mm$^3$)=(d: minor axis)$^2$×(D: major axis)/2. The results are shown in FIG. 13. In FIG. 13, group A (0.9% NaCl control) is indicated with (■), and group B (mice injected with the anti-VEGF antibody) is indicated with (●: 0.5 mg/Kg), (▲: 2.5 mg/Kg), or (Δ: 5.0 mg/Kg). As shown in FIG. 13, significant decreases in tumor volume were observed in mice injected with the KLHc161CC antibody. These results demonstrated that the KLHc161CC antibody of the present invention inhibits (suppresses) the growth of tumors of dogs even in vivo. These results also demonstrated that a pharmaceutical composition comprising the canine IgGB chimeric anti-VEGF antibody of the present invention is significantly effective for treatment or prevention of cancer of dogs.

Example 13

Examination of the Antigen Binding Site of the Antibody of the Present Invention To examine the binding site of the antibody of the present invention in VEGF, a binding experiment based on the ELISA method was conducted as follows.

In this Example, as anti-VEGF antibodies, three anti-VEGF antibodies including KLHc161HC that is an anti-VEGF antibody that inhibits binding of VEGF to NRP1 were selected from human-IgG1 chimeric antibodies obtained in Example 7.

Furthermore, as VEGF, three types of VEGF, (i) VEGF165 containing one of two regions for binding with NRP1 (exon 8a that is the C-terminal region of VEGF), (ii) VEGF121 lacking one of two regions for binding with NRP1 (heparin binding region), and (iii) VEGF165b having an amino acid sequence (exon 8b) differing from the region for binding with NRP1 in VEGF165 were used.

The binding experiment was specifically conducted as follows.

Human VEGF165 (consisting of exon 1, 2, 3, 4, 5, 7 and 8a), human VEGF165b (consisting of exon 1, 2, 3, 4, 5, 7 and 8b) or human VEGF121 (consisting of exon 1, 2, 3, 4, 5 and 8a) was diluted with TBS, dispensed to a 96-well ELISA plate (Nunc) at 20 ng per well, and then incubated at 37° C. for 1 hour, for binding onto the plate surface. Next, after 3 times of washing with 300 μL of 0.02% Tween 20-containing PBS (−) (hereafter, denoted as "PBS-T"), 300 μL of 3% skim milk-containing PBS (−) was dispensed to each well, followed by blocking at 37° C. for 1 hour. After washing with PBS-T, the KLHc161HC antibody serially diluted from the concentration of 1 μg/ml was dispensed to an ELISA plate to which VEGF had been immobilized, and then allowed to react at 37° C. for 1 hour. After washing with PBS-T, a peroxidase-labeled anti-human immunoglobulin antibody (BETHYL) prepared to have a concentration of 100 ng/ml was dispensed at 100 μL per well, and then allowed to react at 37° C. for 1 hour. After washing similarly, TMB Single Solution was added for color development at room temperature. After the reaction was stopped with 1 N sulfuric acid, absorbance at 450 nm was measured using a plate reader (Molecular Devices).

As a result, all of the three anti-VEGF antibodies including KLHc161HC that is the anti-VEGF antibody of the present invention that inhibits binding of VEGF to NRP1 were found to bind to all of VEGF165, VEGF121 and VEGF165b above (FIG. 14).

The result demonstrates that the antibody of the present invention binds to exon 1 to 5 regions on the N-terminal side of VEGF, which are completely different from two regions on the C-terminal side of VEGF known as regions for binding with NRP1.

Moreover, the result surprisingly demonstrates that the antibody of the present invention inhibits binding of VEGF to NRP1, although it binds to exon 1 to 5 regions that are unknown regions for binding of VEGF to NRP1.

INDUSTRIAL APPLICABILITY

According to the present invention, the anti-VEGF antibody that inhibits binding of VEGF to NRP1 is provided. The antibody of the present invention suppresses abnormal angiogenesis, vascular hyperpermeability or cell proliferation due to VEGF, and thus the antibody can be used for treating or preventing cancer, VEGF-mediated eye disease, other diseases associated with of abnormal angiogenesis or vascular hyperpermeability, and the like.

SEQUENCE LISTING FREE TEXT

SEQ ID NO: 13: synthetic DNA
SEQ ID NO: 14: synthetic peptide
SEQ ID NO: 15: synthetic DNA
SEQ ID NO: 16: synthetic peptide
SEQ ID NO: 17: synthetic DNA
SEQ ID NO: 18: synthetic peptide
SEQ ID NO: 19: synthetic DNA
SEQ ID NO: 20: synthetic peptide
SEQ ID NO: 21: synthetic DNA
SEQ ID NO: 22: synthetic peptide
SEQ ID NO: 23: synthetic DNA
SEQ ID NO: 24: synthetic peptide
SEQ ID NO: 25: synthetic DNA
SEQ ID NO: 26: synthetic peptide
SEQ ID NO: 27-34: synthetic DNA
SEQ ID NO: 35: synthetic DNA
SEQ ID NO: 36: synthetic peptide
SEQ ID NO: 37: synthetic DNA
SEQ ID NO: 38: synthetic peptide
SEQ ID NO: 39: synthetic DNA
SEQ ID NO: 40: synthetic peptide
SEQ ID NO: 41: synthetic DNA
SEQ ID NO: 42: synthetic peptide
SEQ ID NO: 43-46: synthetic peptide

The invention claimed is:

1. An antigen binding fragment against VEGF that inhibits binding of a vascular endothelial growth factor (VEGF) to neuropilin-1 (NRP1), wherein the antibody comprises:
   CDR-H1 that comprises the amino acid sequence of SEQ ID NO: 14, CDR-H2 that comprises the amino acid sequence of SEQ ID NO: 16, and CDR-H3 that comprises the amino acid sequence of SEQ ID NO: 18; and
   CDR-L1 that comprises the amino acid sequence of SEQ ID NO: 20, CDR-L2 that comprises the amino acid sequence of Glu-Gly-Asn, and CDR-L3 that comprises the amino acid sequence of SEQ ID NO: 22,
   wherein the antigen-binding fragment is a single-chain antibody or a double-chain antibody.

2. An antibody, or an antigen binding fragment thereof, against VEGF that inhibits binding of a vascular endothelial growth factor (VEGF) to neuropilin-1 (NRP1), wherein the antibody comprises:
   CDR-H1 that comprises the amino acid sequence of SEQ ID NO: 14, CDR-H2 that comprises the amino acid sequence of SEQ ID NO: 16, and CDR-H3 that comprises the amino acid sequence of SEQ ID NO: 18; and
   CDR-L1 that comprises the amino acid sequence of SEQ ID NO: 20, CDR-L2 that comprises the amino acid sequence of Glu-Gly-Asn, and CDR-L3 that comprises the amino acid sequence of SEQ ID NO: 22.

3. The antibody according to claim 2, wherein the antibody inhibits binding of VEGF to vascular endothelial growth factor receptor-2 (VEGFR2).

4. The antibody according to claim 2, wherein the antibody inhibits binding of VEGF to vascular endothelial growth factor receptor-1 (VEGFR1).

5. The antibody according to claim 2, wherein the antibody inhibits binding of VEGF to vascular endothelial growth factor receptor-2 (VEGFR2) and of VEGF to vascular endothelial growth factor receptor-1 (VEGFR1).

6. The antibody according to claim 2, further comprising an amino acid sequence derived from a human IgG1 heavy chain constant region and an amino acid sequence derived from a human IgG1 light chain constant region.

7. The antibody according to claim 6, wherein the amino acid sequence derived from a human IgG1 heavy chain constant region comprises the amino acid sequence of SEQ ID NO: 36, and the amino acid sequence derived from a human IgG1 light chain constant region comprises the amino acid sequence of SEQ ID NO: 38.

8. The antibody according to claim 7, comprising:
   a heavy chain that comprises the amino acid sequence of SEQ ID NO: 24 and the amino acid sequence of SEQ ID NO: 36; and
   a light chain that comprises the amino acid sequence of SEQ ID NO: 26 and the amino acid sequence of SEQ ID NO: 38.

9. The antibody according to claim 2, further comprising an amino acid sequence derived from a canine IgGB heavy chain constant region and an amino acid sequence derived from a canine Ig light chain (κ chain) constant region.

10. The antibody according to claim 9, wherein the amino acid sequence derived from a canine IgGB heavy chain constant region comprises the amino acid sequence of SEQ ID NO: 40, and the amino acid sequence derived from a canine Ig light chain (κ chain) constant region comprises the amino acid sequence of SEQ ID NO: 42.

11. The antibody according to claim 10, comprising:
    a heavy chain that comprises the amino acid sequence of SEQ ID NO: 24 and the amino acid sequence of SEQ ID NO: 40; and
    a light chain that comprises the amino acid sequence of SEQ ID NO: 26 and the amino acid sequence of SEQ ID NO: 42.

12. A pharmaceutical composition comprising the antibody or the fragment thereof according to claim 2, and a pharmaceutically acceptable carrier.

13. A kit comprising the antibody or the fragment thereof according to claim 2, and instructions for using the antibody or the fragment thereof.

14. The antibody according to claim 2, wherein the antibody is a monoclonal antibody.

15. The antibody according to claim 14, wherein the antibody is a chimeric antibody, a humanized antibody, or a caninized antibody.

16. A hybridoma that produces the monoclonal antibody according to claim 14.

17. A method for treating cancer or a VEGF-mediated eye disease, comprising a step of
    administering to a subject a therapeutically effective amount of the antibody or the fragment thereof according to claim 2, wherein the cancer is a solid tumor.

18. The method according to claim 17, wherein the VEGF-mediated eye disease is characterized by aberrant angiogenesis.

19. The method according to claim 18, wherein the VEGF-mediated eye disease characterized by aberrant angiogenesis is at least one selected from the group consisting of age-related macular degeneration, diabetic retinopathy, diabetic macular edema, neovascular glaucoma, retinal vein occlusion, retinopathy of prematurity, choroidal neovascularization associated with pathological myopia, pterygium, rubeosis, pannus, Stevens-Johnson syndrome, and an immunological rejection in a transplanted tissue of the eye.

20. The method according to claim 17, wherein the solid tumor is at least one selected from the group consisting of brain tumor, cervical cancer, esophageal cancer, cancer on the tongue, lung cancer, breast cancer, pancreatic cancer, gastric cancer, cancer of small bowel, duodenal cancer, colon cancer, bladder cancer, renal cancer, liver cancer, prostate cancer, uterine cancer, uterine cervix cancer, ovarian cancer, thyroid cancer, gallbladder cancer, pharyngeal cancer, sarcoma, and melanoma.

\* \* \* \* \*

```
                        SEQUENCE LISTING

<160> NUMBER OF SEQ ID NOS: 46

<210> SEQ ID NO 1
<211> LENGTH: 3487
<212> TYPE: DNA
<213> ORGANISM: Mus musculus

<400> SEQUENCE: 1
cggcggcagc ggagctctgt cgcgagacgc agcgacaagg cagactattc agcggactca      60
ccagcccggg agtctgtgct ctgggatttg atattcaaac ctcttaattt ttttttctta     120
aactgtattg ttttacgctt taatttattt ttgcttccta ttccctctt aaatcgtgcc      180 aacggtttga ggaggttggt tcttcactcc ctcaaatcac ttcggattgt ggaaatcagc     240
agacgaaaga ggtatcaaga gctccagaga gaagtcaagg aagagagaga gagaccggtc     300
agagagagcg cgctggcgag cgaacagaga gagggacagg ggcaaagtga ctgacctgct     360 tttggggtg accgccagag cgcggcgtga gccctccccc ttgggatctt gcatcggacc      420
agtcgcgctg acggacagac agacagacac cgcccccagc cccagcgccc acctcctcgc     480
cggcgggctg ccgacggtgg acgcggcggc gagccgcgag gaaccgaagc ccgcgcccgg     540
aggcggggtg gaggggtcg gggctcgcgg gattgcacgg aaactttcg tccaacttct       600 gggctcttct cgctccgtag tagccgtggt ctgcgccgca ggagacaaac cgatcggagc     660
tgggagaagt gctagctcgg gcctggagaa gccgggcc gagaagagag gggaggaaga       720
gaaggaagag gagaggggc cgcagtgggc gctcggctct caggagccga gctcatggac      780
gggtgaggcg gccgtgtgcg cagacagtgc tccagccgcg cgcgcgcccc aggccccggc     840
ccgggcctcg gttccagaag ggagaggagc ccgccaaggc gcgcaagaga gcgggctgcc     900
tcgcagtccg agccggagag ggagcgcgag ccgcgccggc cccggacggg cctccgaaac     960
catgaacttt ctgctctctt gggtgcactg gaccctggct ttactgctgt acctccacca    1020
tgccaagtgg tccaggctg cacccacgac agaaggagag cagaagtccc atgaagtgat     1080
caagttcatg gatgtctacc agcgaagcta ctgccgtccg attgagaccc tggtggacat    1140
cttccaggag taccccgacg agatagagta catcttcaag ccgtcctgtg tgccgctgat   1200
gcgctgtgca ggctgctgta acgatgaagc cctggagtgc gtgcccacgt cagagagcaa    1260
catcaccatg cagatcatgc ggatcaaacc tcaccaaagc cagcacatag agagatgag     1320 cttcctacag cacagcagat gtgaatgcag accaaagaaa gacagaacaa agccagaaaa    1380
aaaatcagtt cgaggaaagg gaaagggtca aaaacgaaag cgcaagaaat cccggtttaa    1440
atcctggagc gttcactgtg agccttgttc agagcggaga aagcatttgt ttgtccaaga    1500
```

```
tccgcagacg tgtaaatgtt cctgcaaaaa cacagactcg cgttgcaagg cgaggcagct    1560
tgagttaaac gaacgtactt gcagatgtga caagccaagg cggtgagcca ggctgcagga    1620
aggagcctcc ctcagggttt cgggaaccag acctctcacc ggaaagaccg attaaccatg    1680
tcaccaccac gccatcatcg tcaccgttga cagaacagtc cttaatccag aaagcctgac    1740
atgaaggaag aggagactct tcgaggagca ctttgggtcc ggagggcgag actccggcag    1800
acgcattccc gggcaggtga ccaagcacgg tccctcgtgg gactggattc gccattttct    1860
tatatctgct gctaaatcgc caagcccgga agattagggt tgtttctggg attcctgtag    1920
acacacccac ccacatacac acatatatat atattatata tataaataaa tatatatgtt    1980
ttatatataa aatatatata tattcttttt tttaaattaa ctctgctaat gttattggtg    2040
tcttcactgg atatgtttga ctgctgtgga cttgtgttgg gaggaggatg tcctcactcg    2100
gatgccgaca cgggagacaa tgggatgaaa ggcttcagtg tggtctgaga gaggccgaag    2160
tccttttgcc tgccggggag caagcaaggc cagggcacgg gggcacattg gctcacttcc    2220
agaaacacga caaacccatt cctggccctg agtcaagagg acagagagac agatgatgac    2280
agagaaagag ataaagatgc cggttccaac cagaagtttg gggagcctca ggacatggca    2340
tgctttgtgg atccccatga tagtctacaa aagcaccccg cccctctggg cactgcctgg    2400
aagaatcggg agcctggcca gccttcagct cgctcctcca cttctgaggg gcctaggagg    2460
cctcccacag gtgtcccggc aagagaagac acggtggtgg aagaagaggc ctggtaatgg    2520
cccctcctcc tgggacccct tcgtcctctc cttaccccac ctcctgggta cagcccagga    2580
ggaccttgtg tgatcagacc attgaaacca ctaattctgt ccccaggaga cttggctgtg    2640
tgtgtgagtg gcttacccct cctcatcttc ccttcccaag gcacagagca atggggcagg    2700
acccgcaagc ccctcacgga ggcagagaaa agagaaagtg ttttatatac ggtacttatt    2760
taatagccct ttttaattag aaattaaaac agttaattta attaaagagt agggttttt     2820 tcagtattct tggttaatat ttaatttcaa ctatttatga gatgtatctc tcgctctctc    2880
ttatttgtac ttgtgtgtgt gtgtgtgtgt gtgtgtgtgt gtgtgtgtgt gtgtgtatga    2940
aatctgtgtt tccaatctct ctctcccaga tcggtgacag tcactagctt gtcctgagaa    3000
gatatttaat tttgctaaca ctcagctctg ccctcccttg tccccaccac acattccttt    3060
gaaataaggt tcaatatac  atttacatac tatatatata tttggcaact tgtgtttgta    3120
tataaatata tatatatata tatatgttta tgtatatatg tgattctgat aaaatagaca    3180
ttgctattct gttttttata tgtaaaaaca aacaagaaa  aatagagaat tctacatact    3240
aaatctctct ccttttttaa ttttaatatt tgttatcatt tatttattgg tgctactgtt    3300
tatccgtaat aattgtgggg gaaaagata  ttaacatcac gtctttgtct ctagagcagt    3360
tttccgagat attccgtagt acatatttat ttttaaacag caacaaagaa atacagatat    3420
atcttaaaaa aaaagcatt  ttgtattaaa gaattgaatt ctgatctcaa aaaaaaaaa    3480 aaaaaaa                                                              3487

<210> SEQ ID NO 2
<211> LENGTH: 392
<212> TYPE: PRT
<213> ORGANISM: Mus musculus

<400> SEQUENCE: 2

Met Thr Asp Arg Gln Thr Asp Thr Ala Pro Ser Pro Ser Ala His Leu
1               5                   10                  15
```

```
Leu Ala Gly Gly Leu Pro Thr Val Asp Ala Ala Ser Arg Glu Glu
            20                  25                  30
Pro Lys Pro Ala Pro Gly Gly Gly Val Glu Gly Val Gly Ala Arg Gly
         35                  40                  45
Ile Ala Arg Lys Leu Phe Val Gln Leu Leu Gly Ser Ser Arg Ser Val
 50                  55                  60
Val Ala Val Val Cys Ala Ala Gly Asp Lys Pro Ile Gly Ala Gly Arg
 65                  70                  75                  80
Ser Ala Ser Ser Gly Leu Glu Lys Pro Gly Pro Glu Lys Arg Gly Glu
                 85                  90                  95
Glu Glu Lys Glu Glu Glu Arg Gly Pro Gln Trp Ala Leu Gly Ser Gln
             100                 105                 110
Glu Pro Ser Ser Trp Thr Gly Glu Ala Ala Val Cys Ala Asp Ser Ala
         115                 120                 125
Pro Ala Ala Arg Ala Pro Gln Ala Pro Ala Arg Ala Ser Val Pro Glu
130                 135                 140
Gly Arg Gly Ala Arg Gln Gly Ala Gln Glu Ser Gly Leu Pro Arg Ser
145                 150                 155                 160
Pro Ser Arg Arg Gly Ser Ala Ser Arg Ala Gly Pro Gly Arg Ala Ser
                165                 170                 175
Glu Thr Met Asn Phe Leu Leu Ser Trp Val His Trp Thr Leu Ala Leu
            180                 185                 190
Leu Leu Tyr Leu His His Ala Lys Trp Ser Gln Ala Ala Pro Thr Thr
        195                 200                 205
Glu Gly Glu Gln Lys Ser His Glu Val Ile Lys Phe Met Asp Val Tyr
    210                 215                 220
Gln Arg Ser Tyr Cys Arg Pro Ile Glu Thr Leu Val Asp Ile Phe Gln
225                 230                 235                 240
Glu Tyr Pro Asp Glu Ile Glu Tyr Ile Phe Lys Pro Ser Cys Val Pro
                245                 250                 255
Leu Met Arg Cys Ala Gly Cys Cys Asn Asp Glu Ala Leu Glu Cys Val
            260                 265                 270
Pro Thr Ser Glu Ser Asn Ile Thr Met Gln Ile Met Arg Ile Lys Pro
        275                 280                 285
His Gln Ser Gln His Ile Gly Glu Met Ser Phe Leu Gln His Ser Arg
    290                 295                 300
Cys Glu Cys Arg Pro Lys Lys Asp Arg Thr Lys Pro Glu Lys Lys Ser
305                 310                 315                 320
Val Arg Gly Lys Gly Lys Gly Gln Lys Arg Lys Arg Lys Lys Ser Arg
                325                 330                 335
Phe Lys Ser Trp Ser Val His Cys Glu Pro Cys Ser Glu Arg Arg Lys
            340                 345                 350
His Leu Phe Val Gln Asp Pro Gln Thr Cys Lys Cys Ser Cys Lys Asn
        355                 360                 365
Thr Asp Ser Arg Cys Lys Ala Arg Gln Leu Glu Leu Asn Glu Arg Thr
    370                 375                 380
Cys Arg Cys Asp Lys Pro Arg Arg
385                 390

<210> SEQ ID NO 3
<211> LENGTH: 3561
<212> TYPE: DNA
<213> ORGANISM: Rattus norvegicus

<400> SEQUENCE: 3
```

-continued

```
ttggggcagc cgagctgcag cgaggccgcg gcgctggggg cgagctgagc ggcggcagcg      60
gagctctgtc gcgagacgca gcgacaaggc agactattca acggactcat cagccaggga     120
gtctgtgctc tgggatttga tattcaaacc tcttttttt ttcttaaact gtattgtttt     180
acgctttaat ttattttgc ttcctattcc cctcttaaat cgtgccaacg gtttggagag     240
gttgctcctt cactccctca aattacttcg gattttggaa atcagcagag gaaagaggta     300
gcaggagctc cagagagaag tcaaggaaga gagagagaga gagagaccgg tcagagagcg     360
cgctggcgag cgaacagaga gagggacagg ggcaaagtga ctgacctgct tttggggtg      420
accgccagag cgcggcgtga gccctccccc ttgggatctt tcatcggacc agtcgcgctg     480
acggacagac agacagacac cgcccccagc cccagcgccc acctcctcgc cggcgggcag     540
ccgacggtgg acgcggcggc gagccgcgag caggagccga agcccgcgcc cggaggcggg     600
gtggagggg tcgggctcg cgggattgca cggaaacttt tcgtccaact tctgggctct      660
tctctctccg gagtagccgt ggtctgcgcc gcaggaggca aaccgatcgg agctgggaga     720
agtgctagct cgggcctgga gaagccgggg cccgagaaga gagggagaa agagaaggaa      780
gaggagaggg ggccgcagtg ggcgctcggc tctcggagc cgggctcatg gacgggtgag     840
gcggcggtgt gcgcagacag tgctccagcc gcgcgcgcgc cccaggcccc ggcccgggcc     900
tcggttccag aagggagagg agcccgccaa ggcgcgcaag agagcgggct gcctcgcagt     960
ccgagccgga gagggagcgc gagccgcgcc ggccccggac gggcctctga aaccatgaac    1020
tttctgctct cttgggtgca ctggaccctg gctttactgc tgtacctcca ccatgccaag    1080
tggtcccagg ctgcacccac gacagaaggg gagcagaaag cccatgaagt ggtgaagttc    1140
atggacgtct accagcgcag ctattgccgt ccaattgaga ccctggtgga catcttccag    1200
gagtaccccg atgagataga gtatatcttc aagccgtcct gtgtgcccct aatgcggtgt    1260
gcgggctgct gcaatgatga agccctggag tgcgtgccca cgtcggagag caacgtcact    1320
atgcagatca tgcggatcaa acctcaccaa agccagcaca taggagagat gagcttcctg    1380
cagcatagca gatgtgaatg cagaccaaag aaagatagaa caaagccaga aaaaaaatca    1440
gttcgaggaa agggaaaggg tcaaaaacga agcgcaagaa atcccggtt taaatcctgg    1500
agcgttcact gtgagccttg ttcagagcgg agaaagcatt tgtttgtcca agatccgcag    1560
acgtgtaaat gttcctgcaa aaacacagac tcgcgttgca aggcgaggca gcttgagtta    1620
aacgaacgta cttgcagatg tgacaagcca aggcggtgag ccaggctgca ggaaggagcc    1680
tccctcaggg tttcgggaac tagacctctc accggaaaga ccgattaacc atgtcaccac    1740
cacaccacca tcgtcaccgt cgacagaaca gtccttaatc cagaaagcct gacatgaagg    1800
gagaggagac tcttcgagga gcactttggg tccgagggc gagactccgg cagacgcatt    1860
cccgggcagg tgaccaagca cggtggtccc tcgtggaact ggattcgcca tttctttata    1920
tttgctgcta aatcgccaag cccggaagat tagggagttt tgtttctggg attcctgtag    1980
acacacccac ccacatacac acacatatat atatatatat tatatatata aataaatata    2040
tatgttttat atataaaata tatatatatt cttttttttt ttaaattaac tctgctaatg    2100
ttattggtgt cttcactgga tatgtttgac tgctgtggac ttgagttggg aggagatgt     2160
cctcacttgg atcccgacag ggaagacaat gggatgaaag actccggtgt ggtctttcgt    2220
ccttcttaga gaggccgaag tctgtttgcc tgccagggag cacgcaaggc cagggcacgg    2280
gggcacgttg gctcacttcc agaaacacga caaacccatc cctggccctg agtcaagagg    2340
```

```
acagagagac agatgacaga taaagagata aagattctgg ttccgaccag acgtttttgg   2400
ggagcctcag gacatggcac tattgtggat ccccactaga ttctgcaaga gcaccctgcc   2460
cctctgggca ctgcctggaa gaatcaggag cctggccatc aagctctctc ctccacttct   2520
gaggagccta ggaggcctcc cacagggtc ctggcaaaga gaagcacag tggtggaaga    2580 agaggcctgg taatggctcc tcctcctcct cctgggaacc cctcgtcctc tccctacccc   2640
acttcctggg tatagctcag gaggaccttg tgtgatcaga ccattgaaac cactaattct   2700
gtccccagga gacttggctg tgtgtgtgag tggcttaccc ttccccattt tcccttccca   2760
aggtacagag caatggggca ggacccgcaa gcccctcatg gaggcagaga aaagagaaag   2820
tgttttatat acggtactta tttaatagcc ctttttaatt agaaattaaa acagttaatt   2880
taattaaaga gtagggtttt tttcagtatt cttggttaat atttaatttc aactatttat   2940
gaggatgcat ctcttgctct ttcttatttg tactgttttt ttttgttttg tttttctgtg   3000
tgtgtgtgtg tatgaaatct gtgtttccaa tctctctctc ccagatcggt gacagtcact   3060
agcttgtcct gagaagatat ttaattttgc taacactcag ctctgccctc ccctgtcccc   3120
accacacatt cctttgaaat aaggtttcaa tatacattta catactatat atatatttgg   3180
caacttgtgt ttgtatataa atatatatat atatatatgt ttatgtatat atgtgattct   3240
gataaaatag acattgctat tctgttttt atatgtaaaa acaaaacgag aaaaaataga   3300
gaattctaca tactaaatct ctctcctttt ttaattttaa tatttgttat catttattta   3360
ttggtgctac tgtttatccg taataattgt gggggaaaag atattaacat cacgtctttg   3420
tctctagagc agttttccga gatattccgt agtacatatt tattttttaaa cagcaacaaa   3480 gaaatacaga tatatcttaa gaaaaaaaaa gcattttgta ttaaagaatt gaattctgat   3540
ctcaaaaaaa aaaaaaaaaa a                                            3561
```

<210> SEQ ID NO 4
<211> LENGTH: 393
<212> TYPE: PRT
<213> ORGANISM: Rattus norvegicus

<400> SEQUENCE: 4

```
Met Thr Asp Arg Gln Thr Asp Thr Ala Pro Ser Pro Ser Ala His Leu
1               5                   10                  15

Leu Ala Gly Gly Gln Pro Thr Val Asp Ala Ala Ser Arg Glu Gln
            20                  25                  30

Glu Pro Lys Pro Ala Pro Gly Gly Gly Val Glu Gly Val Gly Ala Arg
        35                  40                  45

Gly Ile Ala Arg Lys Leu Phe Val Gln Leu Leu Gly Ser Ser Leu Ser
    50                  55                  60

Gly Val Ala Val Val Cys Ala Ala Gly Lys Pro Ile Gly Ala Gly
65                  70                  75                  80

Arg Ser Ala Ser Ser Gly Leu Glu Lys Pro Gly Pro Glu Lys Arg Gly
                85                  90                  95

Glu Lys Glu Lys Glu Glu Arg Gly Pro Gln Trp Ala Leu Gly Ser
            100                 105                 110

Arg Glu Pro Gly Ser Trp Thr Gly Glu Ala Ala Val Cys Ala Asp Ser
        115                 120                 125

Ala Pro Ala Ala Arg Ala Pro Gln Ala Pro Ala Arg Ala Ser Val Pro
    130                 135                 140

Glu Gly Arg Gly Ala Arg Gln Gly Ala Gln Glu Ser Gly Leu Pro Arg
145                 150                 155                 160
```

```
Ser Pro Ser Arg Arg Gly Ser Ala Ser Arg Ala Gly Pro Gly Arg Ala
                165                 170                 175

Ser Glu Thr Met Asn Phe Leu Leu Ser Trp Val His Trp Thr Leu Ala
            180                 185                 190

Leu Leu Leu Tyr Leu His His Ala Lys Trp Ser Gln Ala Ala Pro Thr
        195                 200                 205

Thr Glu Gly Glu Gln Lys Ala His Glu Val Val Lys Phe Met Asp Val
    210                 215                 220

Tyr Gln Arg Ser Tyr Cys Arg Pro Ile Glu Thr Leu Val Asp Ile Phe
225                 230                 235                 240

Gln Glu Tyr Pro Asp Glu Ile Glu Tyr Ile Phe Lys Pro Ser Cys Val
                245                 250                 255

Pro Leu Met Arg Cys Ala Gly Cys Cys Asn Asp Glu Ala Leu Glu Cys
            260                 265                 270

Val Pro Thr Ser Glu Ser Asn Val Thr Met Gln Ile Met Arg Ile Lys
        275                 280                 285

Pro His Gln Ser Gln His Ile Gly Glu Met Ser Phe Leu Gln His Ser
    290                 295                 300

Arg Cys Glu Cys Arg Pro Lys Lys Asp Arg Thr Lys Pro Glu Lys Lys
305                 310                 315                 320

Ser Val Arg Gly Lys Gly Lys Gly Gln Lys Arg Lys Arg Lys Lys Ser
                325                 330                 335

Arg Phe Lys Ser Trp Ser Val His Cys Glu Pro Cys Ser Glu Arg Arg
            340                 345                 350

Lys His Leu Phe Val Gln Asp Pro Gln Thr Cys Lys Cys Ser Cys Lys
        355                 360                 365

Asn Thr Asp Ser Arg Cys Lys Ala Arg Gln Leu Glu Leu Asn Glu Arg
    370                 375                 380

Thr Cys Arg Cys Asp Lys Pro Arg Arg
385                 390

<210> SEQ ID NO 5
<211> LENGTH: 2828
<212> TYPE: DNA
<213> ORGANISM: Canis lupus familiaris
<220> FEATURE:
<221> NAME/KEY: CDS
<222> LOCATION: (278)..(922)

<400> SEQUENCE: 5
ggaggagggg gaggaggaag aagagaagga agaggagagg gggccgcggt ggcgactcgg      60
cgttcgggag ccgggctcat ggacgggtga ggcggctgtg tgcgcagaca gagctccagc     120
cgcgcgcgcg ccccaggccc cggccccggc cccggcccgg gcctcggctc cgggaggaag     180
aggagcccgc ctaggcgccg aggagagcgg gccgccccgc agcccgagcg ggagagggag     240
cgcgagccgc gccggccccg gccgggcctc gaaaacc atg aac ttt ctg ctc tcc     295
                                        Met Asn Phe Leu Leu Ser
                                          1               5 tgg gtg cat tgg agc ctt gcc ttg ctg ctc tac ctc cac cat gcc aag     343
Trp Val His Trp Ser Leu Ala Leu Leu Leu Tyr Leu His His Ala Lys
         10                  15                  20 tgg tcc cag gct gcg cct atg gca gga gga gag cac aaa ccc cac gaa     391
Trp Ser Gln Ala Ala Pro Met Ala Gly Gly Glu His Lys Pro His Glu
     25                  30                  35 gtg gtg aag ttc atg gac gtc tac cag cgc agc tac tgc cgt ccc att     439
Val Val Lys Phe Met Asp Val Tyr Gln Arg Ser Tyr Cys Arg Pro Ile
 40                  45                  50
```

```
            40                  45                  50
gag acc ctg gtg gac atc ttc cag gag tac cct gac gag atc gag tac      487
Glu Thr Leu Val Asp Ile Phe Gln Glu Tyr Pro Asp Glu Ile Glu Tyr
 55                  60                  65                  70 atc ttc aag cca tcc tgc gtg ccc ctg atg cgg tgt ggg ggc tgc tgt      535
Ile Phe Lys Pro Ser Cys Val Pro Leu Met Arg Cys Gly Gly Cys Cys
                 75                  80                  85 aat gat gag ggc cta gag tgc gtg ccc act gag gag ttc aac atc acc      583
Asn Asp Glu Gly Leu Glu Cys Val Pro Thr Glu Glu Phe Asn Ile Thr
             90                  95                 100 atg cag att atg cgg atc aaa cct cat caa ggc cag cac ata ggg gag      631
Met Gln Ile Met Arg Ile Lys Pro His Gln Gly Gln His Ile Gly Glu
            105                 110                 115 atg agt ttc ctg cag cat agc aaa tgt gaa tgc aga cca aag aaa gat      679
Met Ser Phe Leu Gln His Ser Lys Cys Glu Cys Arg Pro Lys Lys Asp
        120                 125                 130 aga gca agg caa gaa aaa aaa tca att cga gga aag ggg aag ggg caa      727
Arg Ala Arg Gln Glu Lys Lys Ser Ile Arg Gly Lys Gly Lys Gly Gln
135                 140                 145                 150 aaa aga aag cgc aag aaa tcc cgg tat aaa ccc tgg agc gtt ccc tgt      775
Lys Arg Lys Arg Lys Lys Ser Arg Tyr Lys Pro Trp Ser Val Pro Cys
                155                 160                 165 ggg cct tgc tca gag cgg aga aag cat ttg ttt gta caa gat ccg cag      823
Gly Pro Cys Ser Glu Arg Arg Lys His Leu Phe Val Gln Asp Pro Gln
            170                 175                 180 acg tgt aaa tgt tcc tgc aaa aac aca gac tcg cgt tgc aag gcg agg      871
Thr Cys Lys Cys Ser Cys Lys Asn Thr Asp Ser Arg Cys Lys Ala Arg
        185                 190                 195 cag ctt gag tta aac gaa cgt act tgc aga tgt gac aag ccc agg cgg      919
Gln Leu Glu Leu Asn Glu Arg Thr Cys Arg Cys Asp Lys Pro Arg Arg
    200                 205                 210 tga gccgggctgg aagaaggagc ctccctcagg gtttcgggaa ccagacctct            972
caccaggaaa gcctgattca gaatgaccgc tacagaaacc acgccgccgc caccaccacc     1032
acaccaccat caccagaaca atccttaatc agaaacctg aaatgaagga agaggagact      1092
ctgcgcagag cactttgggt ccggagggcg caactccggc agaagcattc ccgggcaggt     1152
gaccaagcac ggtccctctt ggaattggat cgccattgta ttttttcttgc tgctaaatca    1212 ccgagcccgg aagattagag agttttattt ctgggattcc tgtagacaca cccacccaca    1272
tacatacttt tatatatata tataaaatat atatataaaa ataaatatat atattttata    1332
tatacgtaaa atatatatat tcttttttttt taaattaaca ttgctaatgt tattggtgtc   1392
ttcactggat atatttgact gctgtggact taagttggga ggaggctgtc cccacccaga    1452
tcccaacagg gaagaggatg ggaggggaga ctctggcatg atcttttggt ccctcgtagg    1512
aaggccaggg tcccttccc tgcccaggaa cgtgcttggc cagggcacgg gggcaaattt     1572
ggcctgcttt tggggacact gacaaaccca gccctggccc caagcctcta ccccgagtca    1632
aatgaacaga cgacaggtac agggacgagg acactggctc tgactaggag ttcggggagc    1692
ctcaggacac tgctgtactt tgaggatcct ctccacatgc tgcacggacg ggcatcttgc    1752 ccccagggggc actgcctgga agattcagga gactgggcag ccttcaccta ctcttcactt   1812
gctcctgaca agcccagggt gccgccaaca gaggtcttgg cgaaaagaag agagacattg    1872
gtggaggaag gccgcctggg tggcagcttg tcctccgagg gaagggcccc ctgccttggc   1932
catctcccag ctctccttcc ctggtgcagc ccaggagggc ctgacgtcct cagaccattg    1992
aaaccactag ttctgtcccc ccaggagacc tggctgcgtg tgtgtgagtg gttcaccctc    2052
```

```
ctctgtcccc agacccgacc cttcccgcgg cacagagaga cagggcagga tccacgtgcc    2112
caccatggag gcagagaaag tgttttatat acgataatta tttaatatcc cttttaatt     2172 agaaattaaa acagttaatt taattaaaga gtagggtttt tttcagtatt cttggttaat    2232
atttaatttc aactatttat gagatgtatc tctctattgc tctctcttgc gctcttatat    2292
gtaccggtct ttgtgtttaa gattcatgtt tccaatctct ctctccctga tcggtgacag    2352
tcactagctt gtcctgagca gatatttaat tttgctaaca ctcagctctg ccctccccctt   2412 gcccccggct ccccaccaca cattcctttg aaataaggtt tcaatataca tctacagact    2472
atatatatat ttggcaactt gcgtttgtgt gtatatatat atatatatat atatatatat    2532
atgtttatgt atatatgtga ttctgataaa atagacattg ctattctgtt ttttatatgt    2592
aaaaacaaaa caagaaaaaa tagagaattc tacatactaa atctctctcc ttttttaatt    2652
ttaatatttg ttatcattta tttattggtg ctactgttta tccgtaataa ttgtggggga    2712
aaaagatatt aacatcacat ctttgtctct agtacagttt ttcgagatat tccgtagtac    2772
atatttattt ttaaacaaca acaaagaaat acagatatat cttaaaaaaa aaaaaa        2828
```

<210> SEQ ID NO 6
<211> LENGTH: 214
<212> TYPE: PRT
<213> ORGANISM: Canis lupus familiaris

<400> SEQUENCE: 6

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Gly Gly
            20                  25                  30

Glu His Lys Pro His Glu Val Val Lys Phe Met Asp Val Tyr Gln Arg
        35                  40                  45

Ser Tyr Cys Arg Pro Ile Glu Thr Leu Val Asp Ile Phe Gln Glu Tyr
    50                  55                  60

Pro Asp Glu Ile Glu Tyr Ile Phe Lys Pro Ser Cys Val Pro Leu Met
65                  70                  75                  80

Arg Cys Gly Gly Cys Cys Asn Asp Glu Gly Leu Glu Cys Val Pro Thr
                85                  90                  95

Glu Glu Phe Asn Ile Thr Met Gln Ile Met Arg Ile Lys Pro His Gln
            100                 105                 110

Gly Gln His Ile Gly Glu Met Ser Phe Leu Gln His Ser Lys Cys Glu
        115                 120                 125

Cys Arg Pro Lys Lys Asp Arg Ala Arg Gln Glu Lys Lys Ser Ile Arg
    130                 135                 140

Gly Lys Gly Lys Gly Gln Lys Arg Lys Arg Lys Lys Ser Arg Tyr Lys
145                 150                 155                 160

Pro Trp Ser Val Pro Cys Gly Pro Cys Ser Glu Arg Arg Lys His Leu
                165                 170                 175

Phe Val Gln Asp Pro Gln Thr Cys Lys Cys Ser Cys Lys Asn Thr Asp
            180                 185                 190

Ser Arg Cys Lys Ala Arg Gln Leu Glu Leu Asn Glu Arg Thr Cys Arg
        195                 200                 205

Cys Asp Lys Pro Arg Arg
    210
```

<210> SEQ ID NO 7

```
<211> LENGTH: 3677
<212> TYPE: DNA
<213> ORGANISM: Homo sapiens

<400> SEQUENCE: 7
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180 cattttttt  taaaactgta ttgtttctcg ttttaattta ttttgcttg  ccattcccca     240 cttgaatcgg gccgacggct tggggagatt gctctacttc cccaaatcac tgtggatttt     300
ggaaaccagc agaaagagga aagaggtagc aagagctcca gagagaagtc gaggaagaga     360 gagacgggt  cagagagagc gcgcgggcgt gcgagcagcg aaagcgacag ggcaaagtg      420 agtgacctgc ttttgggggt gaccgccgga gcgcggcgtg agccctcccc cttgggatcc     480
cgcagctgac cagtcgcgct gacggacaga cagacagaca ccgccccag  ccccagctac     540 cacctcctcc ccggccggcg gcggacagtg gacgcggcgg cgagccgcgg gcaggggccg     600
gagcccgcgc ccggaggcgg ggtggagggg gtcgggctc  gcggcgtcgc actgaaactt     660
ttcgtccaac ttctgggctg ttctcgcttc ggaggagccg tggtccgcgc gggggaagcc     720
gagccgagcg gagccgcgag aagtgctagc tcgggccggg aggagccgca gccggaggag     780
ggggaggagg aagaagagaa ggaagaggag aggggccgc  agtggcgact cggcgctcgg     840
aagccgggct catggacggg tgaggcggcg gtgtgcgcag acagtgctcc agccgcgcgc     900
gctccccagg ccctggcccg ggcctcgggc cggggaggaa gagtagctcg ccgaggcgcc     960
gaggagagcg ggccgccca  cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag agagatgag  cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gtgtacgttg gtgcccgctg ctgtctaatg    1560
ccctggagcc tccctggccc ccatccctgt gggccttgct cagagcggag aaagcatttg    1620
tttgtacaag atccgcagac gtgtaaatgt tcctgcaaaa acacagactc gcgttgcaag    1680
gcgaggcagc ttgagttaaa cgaacgtact tgcagatgtg acaagccgag gcggtgagcc    1740
gggcaggagg aaggagcctc cctcagggtt tcgggaacca gatctctcac caggaaagac    1800
tgatacagaa cgatcgatac agaaaccacg ctgccgccac cacaccatca ccatcgacag    1860
aacagtcctt aatccagaaa cctgaaatga aggaagagga gactctgcgc agagcacttt    1920
gggtccggag ggcgagactc cggcggaagc attcccgggc gggtgaccca gcacggtccc    1980
tcttggaatt ggattcgcca ttttattttt cttgctgcta aatcaccgag cccggaagat    2040
tagagagttt tatttctggg attcctgtag acacacccac ccacatacat acatttatat    2100
atatatatat tatatatata taaaaataaa tatctctatt ttatatatat aaaatatata    2160
tattcttttt ttaaattaac agtgctaatg ttattggtgt cttcactgga tgtatttgac    2220
```

```
tgctgtggac ttgagttggg aggggaatgt tcccactcag atcctgacag ggaagaggag    2280
gagatgagag actctggcat gatctttttt ttgtcccact tggtggggcc agggtcctct    2340
cccctgccca ggaatgtgca aggccagggc atggggcaa atatgaccca gttttgggaa     2400
caccgacaaa cccagccctg cgctgagcc tctctacccc aggtcagacg gacagaaaga    2460
cagatcacag gtacagggat gaggacaccg gctctgacca ggagtttggg gagcttcagg    2520
acattgctgt gctttgggga ttccctccac atgctgcacg cgcatctcgc ccccaggggc    2580
actgcctgga agattcagga gcctgggcgg ccttcgctta ctctcacctg cttctgagtt    2640
gcccaggaga ccactggcag atgtcccggc gaagagaaga gacacattgt tggaagaagc    2700
agcccatgac agctccccct cctgggactc gccctcatcc tcttcctgct cccttcctg    2760 gggtgcagcc taaaaggacc tatgtcctca ccaccattgaa accactagtt ctgtcccccc    2820
aggagacctg gttgtgtgtg tgtgagtggt tgaccttcct ccatccctg gtccttccct    2880 tcccttcccg aggcacagag agacagggca ggatccacgt gcccattgtg gaggcagaga    2940
aaagagaaag tgttttatat acggtactta tttaatatcc cttttttaatt agaaattaaa    3000 acagttaatt taattaaaga gtagggtttt ttttcagtat tcttggttaa tatttaattt    3060
caactattta tgagatgtat cttttgctct ctcttgctct cttatttgta ccggttttg    3120 tatataaaat tcatgtttcc aatctctctc tccctgatcg gtgacagtca ctagcttatc    3180
ttgaacagat atttaatttt gctaacactc agctctgccc tccccgatcc cctggctccc    3240
cagcacacat tcctttgaaa taaggtttca atatacatct acatactata tatatatttg    3300
gcaacttgta tttgtgtgta tatatatata tatgttta tgtatatatg tgattctgat      3360
aaaatagaca ttgctattct gttttttata tgtaaaaaca aacaagaaa aaatagagaa      3420 ttctacatac taaatctctc tccttttta attttaatat ttgttatcat ttatttattg    3480
gtgctactgt ttatccgtaa taattgtggg gaaaagatat taacatcacg tctttgtctc    3540
tagtgcagtt tttcgagata ttccgtagta catatttatt tttaaacaac gacaaagaaa    3600
tacagatata tcttaaaaaa aaaaaagcat tttgtattaa agaatttaat tctgatctca    3660
aaaaaaaaaa aaaaaaa                                                    3677
```

<210> SEQ ID NO 8
<211> LENGTH: 412
<212> TYPE: PRT
<213> ORGANISM: Homo sapiens

<400> SEQUENCE: 8

```
Met Thr Asp Arg Gln Thr Asp Thr Ala Pro Ser Pro Ser Tyr His Leu
1               5                   10                  15

Leu Pro Gly Arg Arg Thr Val Asp Ala Ala Ser Arg Gly Gln
            20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
            85                  90                  95

Glu Glu Glu Glu Lys Glu Glu Glu Arg Gly Pro Gln Trp Arg Leu Gly
            100                 105                 110
```

```
Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140

Arg Gly Gly Arg Val Ala Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
    370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410
```

<210> SEQ ID NO 9
<211> LENGTH: 366
<212> TYPE: DNA
<213> ORGANISM: Artificial
<220> FEATURE:
<223> OTHER INFORMATION: Synthetic DNA

<400> SEQUENCE: 9

| | | | | | |
|---|---|---|---|---|---|
| gccccgatgg | cggaaggtgg | tggtcaaaac | catcacgagg | tagtcaaatt | tatggacgtt | 60 |
| taccagcgct | cttattgcca | cccaatcgaa | acgctggttg | atattttcca | ggaatatccg | 120 |
| gatgaaatcg | aatacatttt | caaaccgtct | tgtgtcccac | tgatgcgctg | tggtggctgc | 180 |
| tgcaatgacg | agggcctgga | gtgcgttcca | accgaagaat | ccaatattac | gatgcaaatt | 240 |
| atgcgtatta | aaccgcacca | aggccaacac | atcggtgaaa | tgtctttcct | gcagcacaac | 300 |
| aaatgtgaat | gtcgcccgaa | gaaagaccgt | gcacgccagg | aaaagtgtga | caagccgcgt | 360 |

-continued cgttaa                                                                    366

<210> SEQ ID NO 10
<211> LENGTH: 120
<212> TYPE: PRT
<213> ORGANISM: Artificial
<220> FEATURE:
<223> OTHER INFORMATION: Synthetic peptide

<400> SEQUENCE: 10

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Cys Asp Lys Pro Arg
        115                 120

<210> SEQ ID NO 11
<211> LENGTH: 576
<212> TYPE: DNA
<213> ORGANISM: Artificial
<220> FEATURE:
<223> OTHER INFORMATION: Synthetic DNA

<400> SEQUENCE: 11
atgaactttc tgctgtcttg ggtgcattgg agccttgcct tgctgctcta cctccaccat    60
gccaagtggt cccaggctgc acccatggca gaaggaggag gcagaatca tcacgaagtg    120 gtgaagttca tggatgtcta tcagcgcagc tactgccatc caatcgagac cctggtggac    180
atcttccagg agtaccctga tgagatcgag tacatcttca gccatcctg tgtgcccctg    240 atgcgatgcg ggggctgctg caatgacgag ggcctggagt gtgtgccac tgaggagtcc    300 aacatcacca tgcagattat gcggatcaaa cctcaccaag gccagcacat aggagagatg    360
agcttcctac agcacaacaa atgtgaatgc agaccaaaga agatagagc aagacaagaa    420 aatccctgtg gccttgctc agagcggaga aagcatttgt ttgtacaaga tccgcagacg    480
tgtaaatgtt cctgcaaaaa cacagactcg cgttgcaagg cgaggcagct tgagttaaac    540
gaacgtactt gcagatgtga caagccgagg cggtga                              576

<210> SEQ ID NO 12
<211> LENGTH: 191
<212> TYPE: PRT
<213> ORGANISM: Artificial
<220> FEATURE:
<223> OTHER INFORMATION: Synthetic peptide

<400> SEQUENCE: 12

Met Asn Phe Leu Leu Ser Trp Val His Trp Ser Leu Ala Leu Leu Leu
1               5                   10                  15

```
Tyr Leu His His Ala Lys Trp Ser Gln Ala Ala Pro Met Ala Glu Gly
         20                  25                  30

Gly Gly Gln Asn His His Glu Val Val Lys Phe Met Asp Val Tyr Gln
             35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
             100                 105                 110

Gln Gly Gln His Ile Gly Glu Met Ser Phe Leu Gln His Asn Lys Cys
         115                 120                 125

Glu Cys Arg Pro Lys Lys Asp Arg Ala Arg Gln Glu Asn Pro Cys Gly
130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 13
<211> LENGTH: 24
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(24)

<400> SEQUENCE: 13 gga tac aca ttc act agc tat gtt                                        24
Gly Tyr Thr Phe Thr Ser Tyr Val
 1               5

<210> SEQ ID NO 14
<211> LENGTH: 8
<212> TYPE: PRT
<213> ORGANISM: Artificial
<220> FEATURE:
<223> OTHER INFORMATION: Synthetic Construct

<400> SEQUENCE: 14

Gly Tyr Thr Phe Thr Ser Tyr Val
 1               5

<210> SEQ ID NO 15
<211> LENGTH: 24
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(24)

<400> SEQUENCE: 15 att aat cct tac aat gat ggt gct                                        24
Ile Asn Pro Tyr Asn Asp Gly Ala
```

```
<210> SEQ ID NO 16
<211> LENGTH: 8
<212> TYPE: PRT
<213> ORGANISM: Artificial
<220> FEATURE:
<223> OTHER INFORMATION: Synthetic Construct

<400> SEQUENCE: 16

Ile Asn Pro Tyr Asn Asp Gly Ala
1               5

<210> SEQ ID NO 17
<211> LENGTH: 42
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(42)

<400> SEQUENCE: 17 gca acc ttt tac ttc ggt agt agc gac aga gct atg gac tac          42
Ala Thr Phe Tyr Phe Gly Ser Ser Asp Arg Ala Met Asp Tyr
1               5                   10

<210> SEQ ID NO 18
<211> LENGTH: 14
<212> TYPE: PRT
<213> ORGANISM: Artificial
<220> FEATURE:
<223> OTHER INFORMATION: Synthetic Construct

<400> SEQUENCE: 18

Ala Thr Phe Tyr Phe Gly Ser Ser Asp Arg Ala Met Asp Tyr
1               5                   10

<210> SEQ ID NO 19
<211> LENGTH: 18
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(18)

<400> SEQUENCE: 19 act gat att gat gat gat                                          18
Thr Asp Ile Asp Asp Asp
1               5

<210> SEQ ID NO 20
<211> LENGTH: 6
<212> TYPE: PRT
<213> ORGANISM: Artificial
<220> FEATURE:
<223> OTHER INFORMATION: Synthetic Construct

<400> SEQUENCE: 20

Thr Asp Ile Asp Asp Asp
1               5

<210> SEQ ID NO 21
<211> LENGTH: 27
<212> TYPE: DNA
```

```
<213> ORGANISM: Artificial
<220> FEATURE:
<223> OTHER INFORMATION: Synthetic DNA
<220> FEATURE:
<221> NAME/KEY: CDS
<222> LOCATION: (1)..(27)

<400> SEQUENCE: 21 ttg caa agt gat aac ttg ccg tac acg                                27
Leu Gln Ser Asp Asn Leu Pro Tyr Thr
1               5

<210> SEQ ID NO 22
<211> LENGTH: 9
<212> TYPE: PRT
<213> ORGANISM: Artificial
<220> FEATURE:
<223> OTHER INFORMATION: Synthetic Construct

<400> SEQUENCE: 22

Leu Gln Ser Asp Asn Leu Pro Tyr Thr
1               5

<210> SEQ ID NO 23
<211> LENGTH: 364
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(291)

<400> SEQUENCE: 23 gag gtc cag ctg cag cag tct gga cct gag ctg gca aag cct ggg gct    48
Glu Val Gln Leu Gln Gln Ser Gly Pro Glu Leu Ala Lys Pro Gly Ala
1               5                   10                  15 tca gtg aag atg tcc tgc aag gct tct gga tac aca ttc act agc tat    96
Ser Val Lys Met Ser Cys Lys Ala Ser Gly Tyr Thr Phe Thr Ser Tyr
            20                  25                  30 gtt atg cac tgg gtg aag cag aag cct ggg cag ggc ctt gag tgg att   144
Val Met His Trp Val Lys Gln Lys Pro Gly Gln Gly Leu Glu Trp Ile
        35                  40                  45 gga tat att aat cct tac aat gat ggt gct aag tac aat gag aag ttc   192
Gly Tyr Ile Asn Pro Tyr Asn Asp Gly Ala Lys Tyr Asn Glu Lys Phe
    50                  55                  60 aaa ggc aag gcc aca ctg act tca gac aaa tcc tcc agc aca gcc tac   240
Lys Gly Lys Ala Thr Leu Thr Ser Asp Lys Ser Ser Ser Thr Ala Tyr
65                  70                  75                  80 atg gag ctc agc agc ctg acc tct gag gac tct gcg gtc tat tac tgt   288
Met Glu Leu Ser Ser Leu Thr Ser Glu Asp Ser Ala Val Tyr Tyr Cys
                85                  90                  95 gca  accttttact tcggtagtag cgacagagct atggactact ggggtcaagg       341
Ala aacctcagtc accgtctcct cag                                          364

<210> SEQ ID NO 24
<211> LENGTH: 97
<212> TYPE: PRT
<213> ORGANISM: Artificial
<220> FEATURE:
<223> OTHER INFORMATION: Synthetic Construct

<400> SEQUENCE: 24

Glu Val Gln Leu Gln Gln Ser Gly Pro Glu Leu Ala Lys Pro Gly Ala
```

```
               1               5                  10                  15
            Ser Val Lys Met Ser Cys Lys Ala Ser Gly Tyr Thr Phe Thr Ser Tyr
                            20                  25                  30

Val Met His Trp Val Lys Gln Lys Pro Gly Gln Gly Leu Glu Trp Ile
                            35                  40                  45

Gly Tyr Ile Asn Pro Tyr Asn Asp Gly Ala Lys Tyr Asn Glu Lys Phe
                        50                  55                  60

Lys Gly Lys Ala Thr Leu Thr Ser Asp Lys Ser Ser Thr Ala Tyr
            65                  70                  75                  80

Met Glu Leu Ser Ser Leu Thr Ser Glu Asp Ser Ala Val Tyr Tyr Cys
                            85                  90                  95

Ala

<210> SEQ ID NO 25
<211> LENGTH: 322
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(321)

<400> SEQUENCE: 25 gaa aca act gtg acc cag tct cca gca tcc ctg tcc atg gct ata gga        48
Glu Thr Thr Val Thr Gln Ser Pro Ala Ser Leu Ser Met Ala Ile Gly
1               5                   10                  15 gaa aaa gtc acc atc aga tgc ata att agc act gat att gat gat gat        96
Glu Lys Val Thr Ile Arg Cys Ile Ile Ser Thr Asp Ile Asp Asp Asp
                20                  25                  30 atg aac tgg tac cag cag aag cca ggg gaa cct cct aag ctc ctt att       144
Met Asn Trp Tyr Gln Gln Lys Pro Gly Glu Pro Pro Lys Leu Leu Ile
            35                  40                  45 tca gaa ggc aat act ctt cgt cct gga gtc cca tcc cga ttc tcc agc       192
Ser Glu Gly Asn Thr Leu Arg Pro Gly Val Pro Ser Arg Phe Ser Ser
        50                  55                  60 agt ggc tat ggt aca gat ttt gtt ttt aca att gaa aac atg ctc tca       240
Ser Gly Tyr Gly Thr Asp Phe Val Phe Thr Ile Glu Asn Met Leu Ser
65                  70                  75                  80 gaa gat gtt gca gat tac tac tgt ttg caa agt gat aac ttg ccg tac       288
Glu Asp Val Ala Asp Tyr Tyr Cys Leu Gln Ser Asp Asn Leu Pro Tyr
                85                  90                  95 acg ttc gga ggg ggg acc aag ctg gaa ata aaa c                         322
Thr Phe Gly Gly Gly Thr Lys Leu Glu Ile Lys
                100                 105

<210> SEQ ID NO 26
<211> LENGTH: 107
<212> TYPE: PRT
<213> ORGANISM: Artificial
<220> FEATURE:
<223> OTHER INFORMATION: Synthetic Construct

<400> SEQUENCE: 26

Glu Thr Thr Val Thr Gln Ser Pro Ala Ser Leu Ser Met Ala Ile Gly
1               5                   10                  15

Glu Lys Val Thr Ile Arg Cys Ile Ile Ser Thr Asp Ile Asp Asp Asp
                20                  25                  30

Met Asn Trp Tyr Gln Gln Lys Pro Gly Glu Pro Pro Lys Leu Leu Ile
            35                  40                  45
```

```
Ser Glu Gly Asn Thr Leu Arg Pro Gly Val Pro Ser Arg Phe Ser Ser
 50                  55                  60

Ser Gly Tyr Gly Thr Asp Phe Val Phe Thr Ile Glu Asn Met Leu Ser
 65                  70                  75                  80

Glu Asp Val Ala Asp Tyr Tyr Cys Leu Gln Ser Asp Asn Leu Pro Tyr
                 85                  90                  95

Thr Phe Gly Gly Gly Thr Lys Leu Glu Ile Lys
            100                 105

<210> SEQ ID NO 27
<211> LENGTH: 45
<212> TYPE: DNA
<213> ORGANISM: Artificial
<220> FEATURE:
<223> OTHER INFORMATION: Synthetic DNA

<400> SEQUENCE: 27
ctaatacgac tcactatagg gcaagcagtg gtatcaacgc agagt            45

<210> SEQ ID NO 28
<211> LENGTH: 34
<212> TYPE: DNA
<213> ORGANISM: Artificial
<220> FEATURE:
<223> OTHER INFORMATION: Synthetic DNA

<400> SEQUENCE: 28
ccaggggcca gtggatagac cgatggggct gttg                        34

<210> SEQ ID NO 29
<211> LENGTH: 22
<212> TYPE: DNA
<213> ORGANISM: Artificial
<220> FEATURE:
<223> OTHER INFORMATION: Synthetic DNA

<400> SEQUENCE: 29
ctaatacgac tcactatagg gc                                     22

<210> SEQ ID NO 30
<211> LENGTH: 34
<212> TYPE: DNA
<213> ORGANISM: Artificial
<220> FEATURE:
<223> OTHER INFORMATION: Synthetic DNA

<400> SEQUENCE: 30
ccaggggcca gtggatagac cgatggggct gttg                        34

<210> SEQ ID NO 31
<211> LENGTH: 45
<212> TYPE: DNA
<213> ORGANISM: Artificial
<220> FEATURE:
<223> OTHER INFORMATION: Synthetic DNA

<400> SEQUENCE: 31
ctaatacgac tcactatagg gcaagcagtg gtatcaacgc agagt            45

<210> SEQ ID NO 32
<211> LENGTH: 26
<212> TYPE: DNA
<213> ORGANISM: Artificial
<220> FEATURE:
<223> OTHER INFORMATION: Synthetic DNA
```

<210> SEQ ID NO 33
<211> LENGTH: 22
<212> TYPE: DNA
<213> ORGANISM: Artificial
<220> FEATURE:
<223> OTHER INFORMATION: Synthetic DNA

<400> SEQUENCE: 33
ctaatacgac tcactatagg gc                                          22

<210> SEQ ID NO 34
<211> LENGTH: 26
<212> TYPE: DNA
<213> ORGANISM: Artificial
<220> FEATURE:
<223> OTHER INFORMATION: Synthetic DNA

<400> SEQUENCE: 34
gcacctccag atgttaactg ctcact                                      26

<210> SEQ ID NO 35
<211> LENGTH: 1004
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(990)

<400> SEQUENCE: 35

```
gct agc acc aag ggc cca tcg gtc ttc ccc ctg gca ccc tcc tcc aag      48
Ala Ser Thr Lys Gly Pro Ser Val Phe Pro Leu Ala Pro Ser Ser Lys
1               5                   10                  15 agc acc tct ggg ggc aca gcg gcc ctg ggc tgc ctg gtc aag gac tac      96
Ser Thr Ser Gly Gly Thr Ala Ala Leu Gly Cys Leu Val Lys Asp Tyr
            20                  25                  30 ttc ccc gaa ccg gtg acg gtg tcg tgg aac tca ggc gcc ctg acc agc      144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc      192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acc cag acc      240
Leu Ser Ser Val Val Thr Val Pro Ser Ser Ser Leu Gly Thr Gln Thr
65                  70                  75                  80 tac atc tgc aac gtg aat cac aag ccc agc aac acc aag gtg gac aag      288
Tyr Ile Cys Asn Val Asn His Lys Pro Ser Asn Thr Lys Val Asp Lys
                85                  90                  95 aaa gtt gag ccc aaa tct tgt gac aaa act cac aca tgc cca ccg tgc      336
Lys Val Glu Pro Lys Ser Cys Asp Lys Thr His Thr Cys Pro Pro Cys
            100                 105                 110 cca gca cct gaa ctc ctg ggg gga ccg tca gtc ttc ctc ttc ccc cca      384
Pro Ala Pro Glu Leu Leu Gly Gly Pro Ser Val Phe Leu Phe Pro Pro
        115                 120                 125 aaa ccc aag gac acc ctc atg atc tcc cgg acc cct gag gtc aca tgc      432
Lys Pro Lys Asp Thr Leu Met Ile Ser Arg Thr Pro Glu Val Thr Cys
    130                 135                 140 gtg gtg gtg gac gtg agc cac gaa gac cct gag gtc aag ttc aac tgg      480
```

```
                Val Val Val Asp Val Ser His Glu Asp Pro Glu Val Lys Phe Asn Trp
                145                 150                 155                 160 tac gtg gac ggc gtg gag gtg cat aat gcc aag aca aag ccg cgg gag         528
Tyr Val Asp Gly Val Glu Val His Asn Ala Lys Thr Lys Pro Arg Glu
                165                 170                 175 gag cag tac aac agc acg tac cgt gtg gtc agc gtc ctc acc gtc ctg         576
Glu Gln Tyr Asn Ser Thr Tyr Arg Val Val Ser Val Leu Thr Val Leu
                180                 185                 190 cac cag gac tgg ctg aat ggc aag gag tac aag tgc aag gtc tcc aac         624
His Gln Asp Trp Leu Asn Gly Lys Glu Tyr Lys Cys Lys Val Ser Asn
                195                 200                 205 aaa gcc ctc cca gcc ccc atc gag aaa acc atc tcc aaa gcc aaa ggg         672
Lys Ala Leu Pro Ala Pro Ile Glu Lys Thr Ile Ser Lys Ala Lys Gly
    210                 215                 220 cag ccc cga gaa cca cag gtg tac acc ctg ccc cca tcc cgg gag gag         720
Gln Pro Arg Glu Pro Gln Val Tyr Thr Leu Pro Pro Ser Arg Glu Glu
225                 230                 235                 240 atg acc aag aac cag gtc agc ctg acc tgc ctg gtc aaa ggc ttc tat         768
Met Thr Lys Asn Gln Val Ser Leu Thr Cys Leu Val Lys Gly Phe Tyr
                245                 250                 255 ccc agc gac atc gcc gtg gag tgg gag agc aat ggg cag ccg gag aac         816
Pro Ser Asp Ile Ala Val Glu Trp Glu Ser Asn Gly Gln Pro Glu Asn
                260                 265                 270 aac tac aag acc acg cct ccc gtg ctg gac tcc gac ggc tcc ttc ttc         864
Asn Tyr Lys Thr Thr Pro Pro Val Leu Asp Ser Asp Gly Ser Phe Phe
                275                 280                 285 ctc tac agc aag ctc acc gtg gac aag agc agg tgg cag cag ggg aac         912
Leu Tyr Ser Lys Leu Thr Val Asp Lys Ser Arg Trp Gln Gln Gly Asn
                290                 295                 300 gtc ttc tca tgc tcc gtg atg cat gag gct ctg cac aac cac tac acg         960
Val Phe Ser Cys Ser Val Met His Glu Ala Leu His Asn His Tyr Thr
305                 310                 315                 320 cag aag agc ctc tcc ctg tct ccg ggt aaa tgagtcctag ctgg               1004
Gln Lys Ser Leu Ser Leu Ser Pro Gly Lys
                325                 330

<210> SEQ ID NO 36
<211> LENGTH: 330
<212> TYPE: PRT
<213> ORGANISM: Artificial
<220> FEATURE:
<223> OTHER INFORMATION: Synthetic Construct

<400> SEQUENCE: 36

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
            115                 120                 125
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 37
<211> LENGTH: 321
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(318)

<400> SEQUENCE: 37 acg gtg gct gca cca tct gtc ttc atc ttc ccg cca tct gat gag cag      48
Thr Val Ala Ala Pro Ser Val Phe Ile Phe Pro Pro Ser Asp Glu Gln
1               5                   10                  15 ttg aaa tct gga act gcc tct gtt gtg tgc ctg ctg aat aac ttc tat      96
Leu Lys Ser Gly Thr Ala Ser Val Val Cys Leu Leu Asn Asn Phe Tyr
            20                  25                  30 ccc aga gag gcc aaa gta cag tgg aag gtg gat aac gcc ctc caa tcg     144
Pro Arg Glu Ala Lys Val Gln Trp Lys Val Asp Asn Ala Leu Gln Ser
        35                  40                  45 ggt aac tcc cag gag agt gtc aca gag cag gac agc aag gac agc acc     192
Gly Asn Ser Gln Glu Ser Val Thr Glu Gln Asp Ser Lys Asp Ser Thr
    50                  55                  60 tac agc ctc agc agc acc ctg acg ctg agc aaa gca gac tac gag aaa     240
Tyr Ser Leu Ser Ser Thr Leu Thr Leu Ser Lys Ala Asp Tyr Glu Lys
65                  70                  75                  80 cac aaa gtc tac gcc tgc gaa gtc acc cat cag ggc ctg agc tcg ccc     288
His Lys Val Tyr Ala Cys Glu Val Thr His Gln Gly Leu Ser Ser Pro
                85                  90                  95 gtc aca aag agc ttc aac agg gga gag tgt tag                          321
```

Val Thr Lys Ser Phe Asn Arg Gly Glu Cys
            100                 105

<210> SEQ ID NO 38
<211> LENGTH: 106
<212> TYPE: PRT
<213> ORGANISM: Artificial
<220> FEATURE:
<223> OTHER INFORMATION: Synthetic Construct

<400> SEQUENCE: 38

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 39
<211> LENGTH: 1008
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(1008)

<400> SEQUENCE: 39 gcc tcc acc acg gcc ccc tcg gtt ttc cca ctg gcc ccc agc tgc ggg      48
Ala Ser Thr Thr Ala Pro Ser Val Phe Pro Leu Ala Pro Ser Cys Gly
1               5                   10                  15 tcc act tcc ggc tcc acg gtg gcc ctg gcc tgc ctg gtg tca ggc tac      96
Ser Thr Ser Gly Ser Thr Val Ala Leu Ala Cys Leu Val Ser Gly Tyr
            20                  25                  30 ttc ccc gag cct gta act gtg tcc tgg aat tcc ggc tcc ttg acc agc     144
Phe Pro Glu Pro Val Thr Val Ser Trp Asn Ser Gly Ser Leu Thr Ser
        35                  40                  45 ggt gtg cac acc ttc ccg tcc gtc ctg cag tcc tca ggg ctc tac tcc     192
Gly Val His Thr Phe Pro Ser Val Leu Gln Ser Ser Gly Leu Tyr Ser
    50                  55                  60 ctc agc agc atg gtg aca gtg ccc tcc agc agg tgg ccc agc gag acc     240
Leu Ser Ser Met Val Thr Val Pro Ser Ser Arg Trp Pro Ser Glu Thr
65                  70                  75                  80 ttc acc tgc aac gtg gcc cac ccg gcc agc aaa act aaa gta gac aag     288
Phe Thr Cys Asn Val Ala His Pro Ala Ser Lys Thr Lys Val Asp Lys
                85                  90                  95 cca gtg ccc aaa aga gaa aat gga aga gtt cct cgc cca cct gat tgt     336
Pro Val Pro Lys Arg Glu Asn Gly Arg Val Pro Arg Pro Pro Asp Cys
            100                 105                 110 ccc aaa tgc cca gcc cct gaa atg ctg gga ggg cct tcg gtc ttc atc     384
Pro Lys Cys Pro Ala Pro Glu Met Leu Gly Gly Pro Ser Val Phe Ile
        115                 120                 125

| | | | |
|---|---|---|---|
| ttt ccc ccg aaa ccc aag gac acc ctc ttg att gcc cga aca cct gag<br>Phe Pro Pro Lys Pro Lys Asp Thr Leu Leu Ile Ala Arg Thr Pro Glu<br>130                 135                 140 | | | 432 |
| gtc aca tgt gtg gtg gtg gat ctg gac cca gaa gac cct gag gtc cag<br>Val Thr Cys Val Val Val Asp Leu Asp Pro Glu Asp Pro Glu Val Gln<br>145                 150                 155                 160 | | | 480 |
| atc agc tgg ttc gtg gac ggt aag cag atg caa aca gcc aag act cag<br>Ile Ser Trp Phe Val Asp Gly Lys Gln Met Gln Thr Ala Lys Thr Gln<br>                 165                 170                 175 | | | 528 |
| cct cgt gag gag cag ttc aat ggc acc tac cgt gtg gtc agt gtc ctc<br>Pro Arg Glu Glu Gln Phe Asn Gly Thr Tyr Arg Val Val Ser Val Leu<br>            180                 185                 190 | | | 576 |
| ccc att ggg cac cag gac tgg ctc aag ggg aag cag ttc acg tgc aaa<br>Pro Ile Gly His Gln Asp Trp Leu Lys Gly Lys Gln Phe Thr Cys Lys<br>                 195                 200                 205 | | | 624 |
| gtc aac aac aaa gcc ctc cca tcc ccg atc gag agg acc atc tcc aag<br>Val Asn Asn Lys Ala Leu Pro Ser Pro Ile Glu Arg Thr Ile Ser Lys<br>210                 215                 220 | | | 672 |
| gcc aga ggg caa gcc cat cag ccc agt gtg tat gtc ctg cca cca tcc<br>Ala Arg Gly Gln Ala His Gln Pro Ser Val Tyr Val Leu Pro Pro Ser<br>225                 230                 235                 240 | | | 720 |
| cgg gag gag ttg agc aag aac aca gtc agc ttg aca tgc ctg atc aaa<br>Arg Glu Glu Leu Ser Lys Asn Thr Val Ser Leu Thr Cys Leu Ile Lys<br>                 245                 250                 255 | | | 768 |
| gac ttc ttc cca cct gac att gat gtg gag tgg cag agc aat gga cag<br>Asp Phe Phe Pro Pro Asp Ile Asp Val Glu Trp Gln Ser Asn Gly Gln<br>            260                 265                 270 | | | 816 |
| cag gag cct gag agc aag tac cgc acg acc ccg ccc cag ctg gac gag<br>Gln Glu Pro Glu Ser Lys Tyr Arg Thr Thr Pro Pro Gln Leu Asp Glu<br>                 275                 280                 285 | | | 864 |
| gac ggg tcc tac ttc ctg tac agc aag ctc tct gtg gac aag agc cgc<br>Asp Gly Ser Tyr Phe Leu Tyr Ser Lys Leu Ser Val Asp Lys Ser Arg<br>            290                 295                 300 | | | 912 |
| tgg cag cgg gga gac acc ttc ata tgt gcg gtg atg cat gaa gct cta<br>Trp Gln Arg Gly Asp Thr Phe Ile Cys Ala Val Met His Glu Ala Leu<br>305                 310                 315                 320 | | | 960 |
| cac aac cac tac aca cag gaa tcc ctc tcc cat tct ccg ggt aaa tga<br>His Asn His Tyr Thr Gln Glu Ser Leu Ser His Ser Pro Gly Lys<br>                 325                 330                 335 | | | 1008 |

<210> SEQ ID NO 40
<211> LENGTH: 335
<212> TYPE: PRT
<213> ORGANISM: Artificial
<220> FEATURE:
<223> OTHER INFORMATION: Synthetic Construct

<400> SEQUENCE: 40

Ala Ser Thr Thr Ala Pro Ser Val Phe Pro Leu Ala Pro Ser Cys Gly
1               5                   10                  15

Ser Thr Ser Gly Ser Thr Val Ala Leu Ala Cys Leu Val Ser Gly Tyr
                20                  25                  30

Phe Pro Glu Pro Val Thr Val Ser Trp Asn Ser Gly Ser Leu Thr Ser
            35                  40                  45

Gly Val His Thr Phe Pro Ser Val Leu Gln Ser Ser Gly Leu Tyr Ser
        50                  55                  60

Leu Ser Ser Met Val Thr Val Pro Ser Ser Arg Trp Pro Ser Glu Thr
65                  70                  75                  80

Phe Thr Cys Asn Val Ala His Pro Ala Ser Lys Thr Lys Val Asp Lys
                85                  90                  95

```
Pro Val Pro Lys Arg Glu Asn Gly Arg Val Pro Arg Pro Pro Asp Cys
            100                 105                 110

Pro Lys Cys Pro Ala Pro Glu Met Leu Gly Gly Pro Ser Val Phe Ile
        115                 120                 125

Phe Pro Pro Lys Pro Lys Asp Thr Leu Leu Ile Ala Arg Thr Pro Glu
    130                 135                 140

Val Thr Cys Val Val Val Asp Leu Asp Pro Glu Asp Pro Glu Val Gln
145                 150                 155                 160

Ile Ser Trp Phe Val Asp Gly Lys Gln Met Gln Thr Ala Lys Thr Gln
                165                 170                 175

Pro Arg Glu Glu Gln Phe Asn Gly Thr Tyr Arg Val Val Ser Val Leu
            180                 185                 190

Pro Ile Gly His Gln Asp Trp Leu Lys Gly Lys Gln Phe Thr Cys Lys
        195                 200                 205

Val Asn Asn Lys Ala Leu Pro Ser Pro Ile Glu Arg Thr Ile Ser Lys
    210                 215                 220

Ala Arg Gly Gln Ala His Gln Pro Ser Val Tyr Val Leu Pro Pro Ser
225                 230                 235                 240

Arg Glu Glu Leu Ser Lys Asn Thr Val Ser Leu Thr Cys Leu Ile Lys
                245                 250                 255

Asp Phe Phe Pro Pro Asp Ile Asp Val Glu Trp Gln Ser Asn Gly Gln
            260                 265                 270

Gln Glu Pro Glu Ser Lys Tyr Arg Thr Thr Pro Pro Gln Leu Asp Glu
        275                 280                 285

Asp Gly Ser Tyr Phe Leu Tyr Ser Lys Leu Ser Val Asp Lys Ser Arg
    290                 295                 300

Trp Gln Arg Gly Asp Thr Phe Ile Cys Ala Val Met His Glu Ala Leu
305                 310                 315                 320

His Asn His Tyr Thr Gln Glu Ser Leu Ser His Ser Pro Gly Lys
                325                 330                 335

<210> SEQ ID NO 41
<211> LENGTH: 342
<212> TYPE: DNA
<213> ORGANISM: Artificial
<220> FEATURE:
<223> OTHER INFORMATION: Synthetic DNA
<220> FEATURE:
<221> NAME/KEY: CDS
<222> LOCATION: (1)..(342)

<400> SEQUENCE: 41 ctc gag ata aaa aat gat gcc cag cca gcc gtc tat ttg ttc caa cca      48
Leu Glu Ile Lys Asn Asp Ala Gln Pro Ala Val Tyr Leu Phe Gln Pro
1               5                   10                  15 tct cca gac cag tta cac aca gga agt gcc tct gtt gtg tgt ttg ctg      96
Ser Pro Asp Gln Leu His Thr Gly Ser Ala Ser Val Val Cys Leu Leu
            20                  25                  30 aat agc ttc tac ccc aaa gac atc aat gtc aag tgg aaa gtg gat ggt     144
Asn Ser Phe Tyr Pro Lys Asp Ile Asn Val Lys Trp Lys Val Asp Gly
        35                  40                  45 gtc atc caa gac aca ggc atc cag gaa agt gtc aca gag cag gac aag     192
Val Ile Gln Asp Thr Gly Ile Gln Glu Ser Val Thr Glu Gln Asp Lys
    50                  55                  60 gac agt acc tac agc ctc agc agc acc ctg acg atg tcc agt act gag     240
Asp Ser Thr Tyr Ser Leu Ser Ser Thr Leu Thr Met Ser Ser Thr Glu
65                  70                  75                  80
```

```
tac cta agt cat gag ttg tac tcc tgt gag atc act cac aag agc ctg      288
Tyr Leu Ser His Glu Leu Tyr Ser Cys Glu Ile Thr His Lys Ser Leu
             85                  90                  95 ccc tcc acc ctc atc aag agc ttc caa agg agc gag tgt cag aga gtg      336
Pro Ser Thr Leu Ile Lys Ser Phe Gln Arg Ser Glu Cys Gln Arg Val
            100                 105                 110 gac tag                                                              342
Asp
```

<210> SEQ ID NO 42
<211> LENGTH: 113
<212> TYPE: PRT
<213> ORGANISM: Artificial
<220> FEATURE:
<223> OTHER INFORMATION: Synthetic Construct

<400> SEQUENCE: 42

```
Leu Glu Ile Lys Asn Asp Ala Gln Pro Ala Val Tyr Leu Phe Gln Pro
1               5                   10                  15

Ser Pro Asp Gln Leu His Thr Gly Ser Ala Ser Val Val Cys Leu Leu
            20                  25                  30

Asn Ser Phe Tyr Pro Lys Asp Ile Asn Val Lys Trp Lys Val Asp Gly
        35                  40                  45

Val Ile Gln Asp Thr Gly Ile Gln Glu Ser Val Thr Glu Gln Asp Lys
    50                  55                  60

Asp Ser Thr Tyr Ser Leu Ser Ser Thr Leu Thr Met Ser Ser Thr Glu
65                  70                  75                  80

Tyr Leu Ser His Glu Leu Tyr Ser Cys Glu Ile Thr His Lys Ser Leu
                85                  90                  95

Pro Ser Thr Leu Ile Lys Ser Phe Gln Arg Ser Glu Cys Gln Arg Val
            100                 105                 110

Asp
```

<210> SEQ ID NO 43
<211> LENGTH: 114
<212> TYPE: PRT
<213> ORGANISM: Artificial
<220> FEATURE:
<223> OTHER INFORMATION: Synthetic peptide

<400> SEQUENCE: 43

```
Ala Pro Thr Thr Glu Gly Glu Gln Lys Ser His Glu Val Ile Lys Phe
1               5                   10                  15

Met Asp Val Tyr Gln Arg Ser Tyr Cys Arg Pro Ile Glu Thr Leu Val
            20                  25                  30

Asp Ile Phe Gln Glu Tyr Pro Asp Glu Ile Glu Tyr Ile Phe Lys Pro
        35                  40                  45

Ser Cys Val Pro Leu Met Arg Cys Ala Gly Cys Cys Asn Asp Glu Ala
    50                  55                  60

Leu Glu Cys Val Pro Thr Ser Glu Ser Asn Ile Thr Met Gln Ile Met
65                  70                  75                  80

Arg Ile Lys Pro His Gln Ser Gln His Ile Gly Glu Met Ser Phe Leu
                85                  90                  95

Gln His Ser Arg Cys Glu Cys Arg Pro Lys Lys Asp Arg Thr Lys Pro
            100                 105                 110

Glu Asn
```

<210> SEQ ID NO 44

<211> LENGTH: 114
<212> TYPE: PRT
<213> ORGANISM: Artificial
<220> FEATURE:
<223> OTHER INFORMATION: Synthetic peptide

<400> SEQUENCE: 44

Ala Pro Thr Thr Glu Gly Glu Gln Lys Ala His Glu Val Val Lys Phe
1               5                   10                  15

Met Asp Val Tyr Gln Arg Ser Tyr Cys Arg Pro Ile Glu Thr Leu Val
                20                  25                  30

Asp Ile Phe Gln Glu Tyr Pro Asp Glu Ile Glu Tyr Ile Phe Lys Pro
            35                  40                  45

Ser Cys Val Pro Leu Met Arg Cys Ala Gly Cys Cys Asn Asp Glu Ala
    50                  55                  60

Leu Glu Cys Val Pro Thr Ser Glu Ser Asn Val Thr Met Gln Ile Met
65                  70                  75                  80

Arg Ile Lys Pro His Gln Ser Gln His Ile Gly Glu Met Ser Phe Leu
                85                  90                  95

Gln His Ser Arg Cys Glu Cys Arg Pro Lys Lys Asp Arg Thr Lys Pro
            100                 105                 110

Glu Asn

<210> SEQ ID NO 45
<211> LENGTH: 114
<212> TYPE: PRT
<213> ORGANISM: Artificial
<220> FEATURE:
<223> OTHER INFORMATION: Synthetic peptide

<400> SEQUENCE: 45

Ala Pro Met Ala Gly Gly Glu His Lys Pro His Glu Val Val Lys Phe
1               5                   10                  15

Met Asp Val Tyr Gln Arg Ser Tyr Cys Arg Pro Ile Glu Thr Leu Val
                20                  25                  30

Asp Ile Phe Gln Glu Tyr Pro Asp Glu Ile Glu Tyr Ile Phe Lys Pro
            35                  40                  45

Ser Cys Val Pro Leu Met Arg Cys Gly Gly Cys Cys Asn Asp Glu Gly
    50                  55                  60

Leu Glu Cys Val Pro Thr Glu Glu Phe Asn Ile Thr Met Gln Ile Met
65                  70                  75                  80

Arg Ile Lys Pro His Gln Gly Gln His Ile Gly Glu Met Ser Phe Leu
                85                  90                  95

Gln His Ser Lys Cys Glu Cys Arg Pro Lys Lys Asp Arg Ala Arg Gln
            100                 105                 110

Glu Asn

<210> SEQ ID NO 46
<211> LENGTH: 115
<212> TYPE: PRT
<213> ORGANISM: Artificial
<220> FEATURE:
<223> OTHER INFORMATION: Synthetic peptide

<400> SEQUENCE: 46

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

```
Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
                100                 105                 110

Gln Glu Asn
        115
```